(12) United States Patent
Westerhoff et al.

(10) Patent No.: US 11,666,298 B2
(45) Date of Patent: *Jun. 6, 2023

(54) APPARATUS AND SYSTEM FOR RULE BASED VISUALIZATION OF DIGITAL BREAST TOMOSYNTHESIS AND OTHER VOLUMETRIC IMAGES

(71) Applicant: PME IP PTY LTD, Richmond (AU)

(72) Inventors: Malte Westerhoff, Berlin (DE); Detlev Stalling, Berlin (DE)

(73) Assignee: PME IP PTY LTD, Richmond (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/478,797

(22) Filed: Sep. 17, 2021

(65) Prior Publication Data
US 2022/0022833 A1 Jan. 27, 2022

Related U.S. Application Data

(63) Continuation of application No. 16/985,986, filed on Aug. 5, 2020, now Pat. No. 11,129,583, which is a
(Continued)

(51) Int. Cl.
*G06T 1/00* (2006.01)
*G06T 11/00* (2006.01)
(Continued)

(52) U.S. Cl.
CPC ............ *A61B 6/5223* (2013.01); *A61B 6/025* (2013.01); *A61B 6/027* (2013.01); *A61B 6/032* (2013.01);
(Continued)

(58) Field of Classification Search
CPC ....... A61B 6/5223; A61B 6/025; A61B 6/027; A61B 6/032; A61B 6/463; A61B 6/465;
(Continued)

(56) References Cited

U.S. PATENT DOCUMENTS 2,658,310 A 11/1953 Cook
3,431,200 A 3/1969 Davis et al.
(Continued)

FOREIGN PATENT DOCUMENTS

DE 10317384 4/2004
EP 0492897 7/1992
(Continued)

OTHER PUBLICATIONS

ATI Website Index, http://www.ati.com/developer/index.html, Dec. 20, 2002, 2 pages.
(Continued)

*Primary Examiner* — Wesner Sajous
(74) *Attorney, Agent, or Firm* — Sci-Law Strategies, PC

(57) ABSTRACT

The invention provides, in some aspects, a system for implementing a rule derived basis to display volumetric image sets. In various embodiments of the invention, the selection of the images to be displayed, the generation of the 3-D volumetric image from measured 2-D images including the rendering parameters and styles, the choice of viewing directions and 2-D projection images based on the viewing directions, the layout of the projection images, and the formation of a video can be determined using a rule derived basis. In an embodiment of the present invention, the user is presented with sequential images making up a video displayed based on their preferences without having to first manually adjust parameters. The present invention allows for novel ways of viewing such images to detect microcalcifications and obstructions when reviewing Digital Breast Tomosynthesis and other volumetric mammography images.

20 Claims, 21 Drawing Sheets

Related U.S. Application Data continuation of application No. 16/531,413, filed on Aug. 5, 2019, now Pat. No. 10,820,877, which is a continuation of application No. 16/049,801, filed on Jul. 30, 2018, now Pat. No. 10,631,812, which is a continuation of application No. 15/220,325, filed on Jul. 26, 2016, now Pat. No. 10,070,839, which is a continuation-in-part of application No. 14/611,163, filed on Jan. 30, 2015, now Pat. No. 9,524,577, which is a continuation of application No. 13/831,975, filed on Mar. 15, 2013, now Pat. No. 8,976,190.

(60) Provisional application No. 62/197,956, filed on Jul. 28, 2015.

(51) Int. Cl.
| | | |
|---|---|---|
| *G06T 15/08* | (2011.01) | |
| *G06T 19/20* | (2011.01) | |
| *G09G 5/36* | (2006.01) | |
| *G06F 3/048* | (2013.01) | |
| *A61B 6/02* | (2006.01) | |
| *A61B 6/00* | (2006.01) | |
| *A61B 6/03* | (2006.01) | |
| *G16H 30/40* | (2018.01) | |
| *G16H 40/67* | (2018.01) | |
| *G16Z 99/00* | (2019.01) | |
| *G16H 30/20* | (2018.01) | |

(52) U.S. Cl.
CPC .............. *A61B 6/463* (2013.01); *A61B 6/465* (2013.01); *A61B 6/502* (2013.01); *A61B 6/563* (2013.01); *G06T 11/003* (2013.01); *G06T 11/008* (2013.01); *G06T 15/08* (2013.01); *G06T 19/20* (2013.01); *G16H 30/20* (2018.01); *G16H 30/40* (2018.01); *G16H 40/67* (2018.01); *G16Z 99/00* (2019.02); *G06T 2211/412* (2013.01); *G06T 2211/436* (2013.01); *G06T 2219/028* (2013.01)

(58) Field of Classification Search
CPC ......... A61B 6/502; A61B 6/563; A61B 5/742; A61B 5/743; A61B 5/748; G06T 1/003; G06T 11/008; G06T 2211/412; G06T 7/0012; G06T 15/08; G06T 2210/41; G06T 19/20; G06F 19/321; G06F 3/0481; G06F 19/00; G09G 5/363; G16H 50/00; G16H 50/20; G16H 50/50; G16H 40/67; Y10S 128/92; Y10S 128/922; Y10S 128/923; Y10S 128/915; Y10S 128/916
USPC ........................................................ 600/425
See application file for complete search history.

(56) References Cited

U.S. PATENT DOCUMENTS

| | | |
|---|---|---|
| 3,645,040 A | 2/1972 | Ort |
| 4,137,868 A | 2/1979 | Pryor |
| 4,235,043 A | 11/1980 | Harasawa et al. |
| 4,258,661 A | 3/1981 | Margen |
| 4,267,038 A | 5/1981 | Thompson |
| 4,320,594 A | 3/1982 | Raymond |
| 4,746,795 A | 5/1988 | Stewart et al. |
| 4,905,148 A | 2/1990 | Crawford |
| 4,910,912 A | 3/1990 | Lowrey, III |
| 4,928,250 A | 5/1990 | Greenberg et al. |
| 4,958,460 A | 9/1990 | Nielson et al. |
| 4,984,160 A | 1/1991 | Saint Felix et al. |
| 5,031,117 A | 7/1991 | Minor et al. |
| 5,091,960 A | 2/1992 | Butler |
| 5,121,708 A | 6/1992 | Nuttle |
| 5,128,864 A | 7/1992 | Waggener et al. |
| 5,218,534 A | 6/1993 | Trousset et al. |
| 5,235,510 A | 8/1993 | Yamada |
| 5,241,471 A | 8/1993 | Trousset et al. |
| 5,253,171 A | 10/1993 | Hsiao et al. |
| 5,274,759 A | 12/1993 | Yoshioka |
| 5,280,428 A | 1/1994 | Wu et al. |
| 5,287,274 A | 2/1994 | Saint Felix et al. |
| 5,293,313 A | 3/1994 | Cecil |
| 5,307,264 A | 4/1994 | Waggener et al. |
| 5,355,453 A | 10/1994 | Row et al. |
| 5,368,033 A | 11/1994 | Moshfeghi |
| 5,375,156 A | 12/1994 | Kuo-Petravic et al. |
| 5,412,703 A | 5/1995 | Goodenough et al. |
| 5,412,764 A | 5/1995 | Tanaka |
| 5,442,672 A | 8/1995 | Bjorkholm et al. |
| 5,452,416 A | 9/1995 | Hilton |
| 5,488,700 A | 1/1996 | Glassner |
| 5,560,360 A | 10/1996 | Filler |
| 5,594,842 A | 1/1997 | Kaufman et al. |
| 5,602,892 A | 2/1997 | Llacer |
| 5,633,951 A | 5/1997 | Moshfeghi |
| 5,633,999 A | 5/1997 | Clowes et al. |
| 5,640,436 A | 6/1997 | Kawai et al. |
| 5,671,265 A | 9/1997 | Andress |
| 5,744,802 A | 4/1998 | Muehllehner et al. |
| 5,774,519 A | 6/1998 | Lindstrom et al. |
| 5,790,787 A | 8/1998 | Scott et al. |
| 5,793,374 A | 8/1998 | Guenter et al. |
| 5,793,879 A | 8/1998 | Benn et al. |
| 5,813,988 A | 9/1998 | Alfano et al. |
| 5,821,541 A | 10/1998 | Tumer |
| 5,825,842 A | 10/1998 | Taguchi |
| 5,838,756 A | 11/1998 | Taguchi et al. |
| 5,841,140 A | 11/1998 | McCroskey et al. |
| 5,909,476 A | 6/1999 | Cheng et al. |
| 5,930,384 A | 7/1999 | Guillemaud et al. |
| 5,931,789 A | 8/1999 | Alfano et al. |
| 5,950,203 A | 9/1999 | Stakuis |
| 5,960,056 A | 9/1999 | Lai |
| 5,963,612 A | 10/1999 | Navab |
| 5,963,613 A | 10/1999 | Navab |
| 5,963,658 A | 10/1999 | Klibanov et al. |
| 6,002,739 A | 12/1999 | Heumann |
| 6,018,562 A | 1/2000 | Willson |
| 6,032,264 A | 2/2000 | Beffa et al. |
| 6,044,132 A | 3/2000 | Navab |
| 6,049,390 A | 4/2000 | Notredame |
| 6,049,582 A | 4/2000 | Navab |
| 6,072,177 A | 6/2000 | Mccroskey et al. |
| 6,088,423 A | 7/2000 | Krug et al. |
| 6,091,422 A | 7/2000 | Ouaknine et al. |
| 6,104,827 A | 8/2000 | Benn et al. |
| 6,105,029 A | 8/2000 | Maddalozzo, Jr. et al. |
| 6,108,007 A | 8/2000 | Shochet |
| 6,108,576 A | 8/2000 | Alfano et al. |
| 6,123,733 A | 9/2000 | Dalton |
| 6,175,655 B1 | 1/2001 | George |
| 6,205,120 B1 | 3/2001 | Packer et al. |
| 6,219,061 B1 | 4/2001 | Lauer et al. |
| 6,226,005 B1 | 5/2001 | Laferriere |
| 6,236,704 B1 | 5/2001 | Navab et al. |
| 6,243,098 B1 | 6/2001 | Lauer et al. |
| 6,249,594 B1 | 6/2001 | Hibbard |
| 6,255,655 B1 | 7/2001 | McCroskey et al. |
| 6,264,610 B1 | 7/2001 | Zhu |
| 6,268,846 B1 | 7/2001 | Georgiev |
| 6,278,460 B1 | 8/2001 | Myers et al. |
| 6,282,256 B1 | 8/2001 | Grass et al. |
| 6,289,235 B1 | 9/2001 | Webber et al. |
| 6,304,771 B1 | 10/2001 | Yodh et al. |
| 6,320,928 B1 | 11/2001 | Vaillant et al. |
| 6,324,241 B1 | 11/2001 | Besson |
| 6,377,257 B1 | 4/2002 | Borrel |
| 6,377,266 B1 | 4/2002 | Baldwin |
| 6,384,821 B1 | 5/2002 | Borrel |
| 6,404,843 B1 | 6/2002 | Vaillant |
| 6,415,013 B1 | 7/2002 | Hsieh et al. |

(56) References Cited

U.S. PATENT DOCUMENTS

| | | | |
|---|---|---|---|
| 6,470,067 B1 | 10/2002 | Harding | |
| 6,470,070 B2 | 10/2002 | Menhardt | |
| 6,473,793 B1 | 10/2002 | Dillon et al. | |
| 6,475,150 B2 | 11/2002 | Haddad | |
| 6,507,633 B1 | 1/2003 | Elbakri et al. | |
| 6,510,241 B1 | 1/2003 | Vaillant et al. | |
| 6,519,355 B2 | 2/2003 | Nelson | |
| 6,526,305 B1 | 2/2003 | Mori | |
| 6,557,102 B1 | 4/2003 | Wong et al. | |
| 6,559,958 B2 | 5/2003 | Motamed | |
| 6,591,004 B1 | 7/2003 | Vanessen et al. | |
| 6,615,063 B1 | 9/2003 | Ntziachristos et al. | |
| 6,633,688 B1 | 10/2003 | Nixon | |
| 6,636,623 B2 | 10/2003 | Nelson et al. | |
| 6,654,012 B1 | 11/2003 | Lauer et al. | |
| 6,658,142 B1 | 12/2003 | Kam et al. | |
| 6,664,963 B1 | 12/2003 | Zatz | |
| 6,674,430 B1 | 1/2004 | Kaufman et al. | |
| 6,697,508 B2 | 2/2004 | Nelson | |
| 6,707,878 B2 | 3/2004 | Claus et al. | |
| 6,718,195 B2 | 4/2004 | Van Der Mark et al. | |
| 6,731,283 B1 | 5/2004 | Navab | |
| 6,740,232 B1 | 5/2004 | Beaulieu | |
| 6,741,730 B2 | 5/2004 | Rahn et al. | |
| 6,744,253 B2 | 6/2004 | Stolarczyk | |
| 6,744,845 B2 | 6/2004 | Harding et al. | |
| 6,745,070 B2 | 6/2004 | Wexler et al. | |
| 6,747,654 B1 | 6/2004 | Laksono et al. | |
| 6,754,299 B2 | 6/2004 | Patch | |
| 6,765,981 B2 | 7/2004 | Heumann | |
| 6,768,782 B1 | 7/2004 | Hsieh et al. | |
| 6,770,893 B2 | 8/2004 | Nelson | |
| 6,771,733 B2 | 8/2004 | Katsevich | |
| 6,778,127 B2 | 8/2004 | Stolarczyk et al. | |
| 6,785,409 B1 | 8/2004 | Suri | |
| 6,798,417 B1 | 9/2004 | Taylor | |
| 6,807,581 B1 | 10/2004 | Starr et al. | |
| 6,825,840 B2 | 11/2004 | Gritz | |
| 6,825,843 B2 | 11/2004 | Allen et al. | |
| 6,923,906 B2 | 8/2005 | Oswald et al. | |
| 6,947,047 B1 | 9/2005 | Moy et al. | |
| 6,978,206 B1 | 12/2005 | Pu | |
| 7,003,547 B1 | 2/2006 | Hubbard | |
| 7,006,101 B1 | 2/2006 | Brown et al. | |
| 7,031,022 B1 | 4/2006 | Komori et al. | |
| 7,034,828 B1 | 4/2006 | Drebin et al. | |
| 7,039,723 B2 | 5/2006 | Hu | |
| 7,050,953 B2 | 5/2006 | Chiang et al. | |
| 7,054,852 B1 | 5/2006 | Cohen | |
| 7,058,644 B2 | 6/2006 | Patchet et al. | |
| 7,076,735 B2 | 7/2006 | Callegari | |
| 7,098,907 B2 | 8/2006 | Houston et al. | |
| 7,120,283 B2 | 10/2006 | Thieret | |
| 7,133,041 B2 | 11/2006 | Kaufman et al. | |
| 7,154,985 B2 | 12/2006 | Dobbs | |
| 7,167,176 B2 | 1/2007 | Sloan et al. | |
| 7,184,041 B2 | 2/2007 | Heng et al. | |
| 7,185,003 B2 | 2/2007 | Bayliss et al. | |
| 7,219,085 B2 | 5/2007 | Buck et al. | |
| 7,242,401 B2 | 7/2007 | Yang et al. | |
| 7,262,770 B2 | 8/2007 | Sloan et al. | |
| 7,274,368 B1 | 9/2007 | Keslin | |
| 7,299,232 B2 | 11/2007 | Stakutis et al. | |
| 7,315,926 B2 | 1/2008 | Fridella et al. | |
| 7,324,116 B2 | 1/2008 | Boyd et al. | |
| 7,339,585 B2 | 3/2008 | Verstraelen et al. | |
| 7,472,156 B2 | 12/2008 | Philbrick et al. | |
| 7,502,869 B2 | 3/2009 | Boucher et al. | |
| 7,506,375 B2 | 3/2009 | Kanda et al. | |
| 7,552,192 B2 | 6/2009 | Carmichael | |
| 7,609,884 B1 | 10/2009 | Stalling | |
| 7,693,318 B1 | 4/2010 | Stalling | |
| 7,701,210 B2 | 4/2010 | Ichinose | |
| 7,778,392 B1 | 8/2010 | Bergman | |
| 7,876,944 B2 | 1/2011 | Stalling | |
| 7,889,895 B2 | 2/2011 | Nowinski | |
| 7,899,516 B2 | 3/2011 | Chen et al. | |
| 7,907,759 B2 | 3/2011 | Hundley | |
| 7,956,612 B2 | 6/2011 | Sorensen | |
| 7,983,300 B2 | 7/2011 | Vaughan et al. | |
| 7,991,837 B1* | 8/2011 | Tahan | G06F 3/0481 348/240.3 |
| 7,992,100 B2* | 8/2011 | Lundstrom | G16H 40/63 715/810 |
| 7,995,824 B2 | 8/2011 | Yim | |
| 8,107,592 B2 | 1/2012 | Bergman | |
| 8,189,002 B1 | 5/2012 | Westerhoff | |
| 8,319,781 B2 | 11/2012 | Westerhoff | |
| 8,369,600 B2 | 2/2013 | Can et al. | |
| 8,386,560 B2 | 2/2013 | Ma | |
| 8,392,529 B2 | 3/2013 | Westerhoff | |
| 8,508,539 B2 | 8/2013 | Vlietinck | |
| 8,538,108 B2 | 9/2013 | Shekhar | |
| 8,542,136 B1 | 9/2013 | Owsley et al. | |
| 8,548,215 B2 | 10/2013 | Westerhoff | |
| 8,745,413 B2 | 6/2014 | Hahn | |
| 8,775,510 B2 | 7/2014 | Westerhoff | |
| 8,976,190 B1 | 3/2015 | Westerhoff | |
| 9,019,287 B2 | 4/2015 | Westerhoff | |
| 9,167,027 B2 | 10/2015 | Westerhoff | |
| 9,299,156 B2 | 3/2016 | Zalis | |
| 9,355,616 B2 | 5/2016 | Westerhoff | |
| 9,454,813 B2 | 9/2016 | Westerhoff | |
| 9,509,802 B1 | 11/2016 | Westerhoff | |
| 9,524,577 B1 | 12/2016 | Westerhoff | |
| 9,531,789 B2 | 12/2016 | Westerhoff | |
| 9,595,242 B1 | 3/2017 | Westerhoff | |
| 9,728,165 B1 | 8/2017 | Westerhoff | |
| 9,749,245 B2 | 8/2017 | Stalling | |
| 9,860,300 B2 | 1/2018 | Westerhoff | |
| 9,898,855 B2 | 2/2018 | Westerhoff | |
| 9,904,969 B1 | 2/2018 | Westerhoff | |
| 9,984,460 B2 | 5/2018 | Westerhoff | |
| 9,984,478 B2 | 5/2018 | Westerhoff | |
| 10,038,739 B2 | 7/2018 | Westerhoff | |
| 10,043,482 B2 | 8/2018 | Westerhoff | |
| 10,070,839 B2* | 9/2018 | Westerhoff | G16H 40/67 |
| 10,311,541 B2 | 6/2019 | Westerhoff | |
| 10,320,684 B2 | 6/2019 | Stalling | |
| 10,373,368 B2 | 8/2019 | Westerhoff | |
| 10,380,970 B2 | 8/2019 | Westerhoff | |
| 10,395,398 B2 | 8/2019 | Westerhoff | |
| 10,430,914 B2 | 10/2019 | Westerhoff | |
| 10,448,911 B2 | 10/2019 | Erhard | |
| 10,540,803 B2 | 1/2020 | Westerhoff | |
| 10,614,543 B2 | 4/2020 | Westerhoff | |
| 10,631,812 B2* | 4/2020 | Westerhoff | G16H 40/67 |
| 10,686,868 B2 | 6/2020 | Westerhoff | |
| 10,706,538 B2 | 7/2020 | Westerhoff | |
| 10,820,877 B2* | 11/2020 | Westerhoff | G16H 40/67 |
| 11,075,978 B2 | 7/2021 | Westerhoff | |
| 11,129,583 B2* | 9/2021 | Westerhoff | G16Z 99/00 |
| 2001/0026848 A1 | 10/2001 | Van Der Mark | |
| 2002/0016813 A1 | 2/2002 | Woods et al. | |
| 2002/0034817 A1 | 3/2002 | Henry et al. | |
| 2002/0049825 A1 | 4/2002 | Jewett et al. | |
| 2002/0080143 A1 | 6/2002 | Morgan et al. | |
| 2002/0089587 A1 | 7/2002 | White et al. | |
| 2002/0099290 A1 | 7/2002 | Haddad | |
| 2002/0099844 A1 | 7/2002 | Baumann et al. | |
| 2002/0120727 A1 | 8/2002 | Curley et al. | |
| 2002/0123680 A1 | 9/2002 | Vailant | |
| 2002/0138019 A1 | 9/2002 | Wexler | |
| 2002/0150202 A1 | 10/2002 | Harding | |
| 2002/0150285 A1 | 10/2002 | Nelson | |
| 2002/0180747 A1 | 12/2002 | Lavelle et al. | |
| 2002/0184238 A1 | 12/2002 | Chylla | |
| 2002/0184349 A1 | 12/2002 | Manukyan | |
| 2003/0001842 A1 | 1/2003 | Munshi | |
| 2003/0031352 A1 | 2/2003 | Nelson et al. | |
| 2003/0059110 A1 | 3/2003 | Wilt | |
| 2003/0065268 A1 | 4/2003 | Chen et al. | |
| 2003/0086599 A1 | 5/2003 | Armato | |
| 2003/0103666 A1 | 6/2003 | Edie et al. | |

(56) References Cited

U.S. PATENT DOCUMENTS

| | | |
|---|---|---|
| 2003/0120743 A1 | 6/2003 | Coatney et al. |
| 2003/0123720 A1 | 7/2003 | Launay et al. |
| 2003/0149812 A1 | 8/2003 | Schoenthal et al. |
| 2003/0158786 A1 | 8/2003 | Yaron |
| 2003/0176780 A1 | 9/2003 | Arnold |
| 2003/0179197 A1 | 9/2003 | Sloan et al. |
| 2003/0194049 A1 | 10/2003 | Claus et al. |
| 2003/0220569 A1 | 11/2003 | Dione |
| 2003/0220772 A1 | 11/2003 | Chiang et al. |
| 2003/0227456 A1 | 12/2003 | Gritz |
| 2003/0234791 A1 | 12/2003 | Boyd et al. |
| 2004/0010397 A1 | 1/2004 | Barbour et al. |
| 2004/0012596 A1 | 1/2004 | Allen et al. |
| 2004/0015062 A1 | 1/2004 | Ntziachristos et al. |
| 2004/0022348 A1 | 2/2004 | Heumann |
| 2004/0059822 A1 | 3/2004 | Jiang |
| 2004/0066384 A1 | 4/2004 | Ohba |
| 2004/0066385 A1 | 4/2004 | Kilgard |
| 2004/0066891 A1 | 4/2004 | Freytag |
| 2004/0078238 A1 | 4/2004 | Thomas et al. |
| 2004/0102688 A1 | 5/2004 | Walker |
| 2004/0125103 A1 | 7/2004 | Kaufman |
| 2004/0133652 A1 | 7/2004 | Miloushev et al. |
| 2004/0147039 A1 | 7/2004 | Van Der Mark |
| 2004/0162677 A1 | 8/2004 | Bednar |
| 2004/0170302 A1 | 9/2004 | Museth et al. |
| 2004/0210584 A1 | 10/2004 | Nir et al. |
| 2004/0215858 A1 | 10/2004 | Armstrong et al. |
| 2004/0215868 A1 | 10/2004 | Solomon et al. |
| 2004/0239672 A1 | 12/2004 | Schmidt |
| 2004/0240753 A1 | 12/2004 | Hu |
| 2005/0012753 A1 | 1/2005 | Karlov |
| 2005/0017972 A1 | 1/2005 | Poole et al. |
| 2005/0066095 A1 | 3/2005 | Mullick et al. |
| 2005/0088440 A1 | 4/2005 | Sloan et al. |
| 2005/0128195 A1 | 6/2005 | Houston et al. |
| 2005/0152590 A1 | 7/2005 | Thieret |
| 2005/0165623 A1 | 7/2005 | Landi et al. |
| 2005/0225554 A1 | 10/2005 | Bastos et al. |
| 2005/0231503 A1 | 10/2005 | Heng et al. |
| 2005/0239182 A1 | 10/2005 | Berzin |
| 2005/0240628 A1 | 10/2005 | Jiang et al. |
| 2005/0256742 A1 | 11/2005 | Kohan et al. |
| 2005/0259103 A1 | 11/2005 | Kilgard et al. |
| 2005/0270298 A1 | 12/2005 | Thieret |
| 2005/0271302 A1 | 12/2005 | Khamene et al. |
| 2006/0010438 A1 | 1/2006 | Brady et al. |
| 2006/0010454 A1 | 1/2006 | Napoli et al. |
| 2006/0028479 A1 | 2/2006 | Chun |
| 2006/0034511 A1 | 2/2006 | Verstraelen |
| 2006/0066609 A1 | 3/2006 | Iodice |
| 2006/0197780 A1 | 9/2006 | Watkins et al. |
| 2006/0214949 A1 | 9/2006 | Zhang |
| 2006/0239540 A1 | 10/2006 | Serra |
| 2006/0239589 A1 | 10/2006 | Omernick |
| 2006/0282253 A1 | 12/2006 | Buswell et al. |
| 2007/0005798 A1 | 1/2007 | Gropper et al. |
| 2007/0038939 A1 | 2/2007 | Challen |
| 2007/0046966 A1 | 3/2007 | Mussack |
| 2007/0067497 A1 | 3/2007 | Craft et al. |
| 2007/0092864 A1 | 4/2007 | Reinhardt |
| 2007/0097133 A1 | 5/2007 | Stauffer et al. |
| 2007/0116332 A1 | 5/2007 | Cai et al. |
| 2007/0127802 A1 | 6/2007 | Odry |
| 2007/0156955 A1 | 7/2007 | Royer, Jr. |
| 2007/0165917 A1 | 7/2007 | Cao et al. |
| 2007/0185879 A1 | 8/2007 | Roublev et al. |
| 2007/0188488 A1 | 8/2007 | Choi |
| 2007/0226314 A1* | 9/2007 | Eick ............... G06F 16/986 709/217 |
| 2007/0255704 A1 | 11/2007 | Baek et al. |
| 2007/0280518 A1 | 12/2007 | Nowinski |
| 2008/0009055 A1 | 1/2008 | Lewnard |
| 2008/0042923 A1 | 2/2008 | De Laet |
| 2008/0086557 A1 | 4/2008 | Roach |
| 2008/0115139 A1 | 5/2008 | Inglett et al. |
| 2008/0137929 A1 | 6/2008 | Chen et al. |
| 2008/0147554 A1 | 6/2008 | Stevens et al. |
| 2008/0155890 A1 | 7/2008 | Oyler |
| 2008/0166070 A1* | 7/2008 | Kariathungal ......... G16H 30/40 382/305 |
| 2008/0174593 A1 | 7/2008 | Ham |
| 2008/0208961 A1 | 8/2008 | Kim et al. |
| 2008/0224700 A1 | 9/2008 | Sorensen |
| 2008/0281908 A1 | 11/2008 | McCanne et al. |
| 2008/0317317 A1 | 12/2008 | Shekhar |
| 2009/0005693 A1 | 1/2009 | Brauner et al. |
| 2009/0043988 A1 | 2/2009 | Archer et al. |
| 2009/0077097 A1 | 3/2009 | Lacapra et al. |
| 2009/0147793 A1 | 6/2009 | Hayakawa et al. |
| 2009/0208082 A1 | 8/2009 | Westerhoff et al. |
| 2009/0210487 A1 | 8/2009 | Westerhoff et al. |
| 2009/0225076 A1 | 9/2009 | Vlietinck |
| 2009/0245610 A1 | 10/2009 | Can et al. |
| 2009/0313170 A1 | 12/2009 | Goldner et al. |
| 2010/0054556 A1 | 3/2010 | Novatzky |
| 2010/0060652 A1 | 3/2010 | Karlsson |
| 2010/0123733 A1 | 5/2010 | Zaharia |
| 2010/0174823 A1 | 7/2010 | Huang |
| 2010/0272342 A1 | 10/2010 | Berman et al. |
| 2010/0278405 A1 | 11/2010 | Kakadiaris et al. |
| 2011/0044524 A1 | 2/2011 | Wang et al. |
| 2011/0112862 A1 | 5/2011 | Yu |
| 2012/0078088 A1 | 3/2012 | Whitestone et al. |
| 2012/0150034 A1* | 6/2012 | DeFreitas ............... A61B 8/483 250/363.04 |
| 2012/0226916 A1 | 9/2012 | Hahn |
| 2012/0233153 A1 | 9/2012 | Roman et al. |
| 2013/0129198 A1* | 5/2013 | Sherman ............... G16H 30/20 382/159 |
| 2013/0176319 A1 | 7/2013 | Westerhoff |
| 2013/0195329 A1 | 8/2013 | Canda |
| 2015/0213288 A1 | 7/2015 | Bilodeau et al. |
| 2016/0012181 A1 | 1/2016 | Massey |
| 2017/0011514 A1 | 1/2017 | Westerhoff |
| 2017/0346883 A1 | 3/2017 | Westerhoff |
| 2017/0098329 A1 | 4/2017 | Westerhoff |
| 2017/0104811 A1 | 4/2017 | Westerhoff |
| 2017/0178593 A1 | 6/2017 | Westerhoff |
| 2017/0200064 A1* | 7/2017 | Reicher ................. G16H 30/40 |
| 2017/0200270 A1* | 7/2017 | Reicher ................. A61B 5/742 |
| 2019/0096062 A1 | 3/2019 | Westerhoff |
| 2019/0236782 A1* | 8/2019 | Amit ..................... G16H 50/20 |
| 2019/0318512 A1 | 10/2019 | Westerhoff |
| 2021/0133978 A1 | 5/2021 | Ma |

FOREIGN PATENT DOCUMENTS

| | | |
|---|---|---|
| EP | 0502187 | 9/1992 |
| EP | 0611181 | 8/1994 |
| EP | 0476070 | 8/1996 |
| EP | 0925556 | 6/1999 |
| EP | 0953943 | 11/1999 |
| EP | 0964 366 | 12/1999 |
| EP | 187340 | 3/2001 |
| EP | 2098895 | 9/2009 |
| EP | 2098994 | 9/2009 |
| EP | 2405344 | 1/2012 |
| WO | WO9016072 | 12/1990 |
| WO | WO9102320 | 2/1991 |
| WO | WO9205507 | 4/1992 |
| WO | WO9642022 | 12/1996 |
| WO | WO9810378 | 3/1998 |
| WO | WO9812667 | 3/1998 |
| WO | WO9833057 | 7/1998 |
| WO | WO0120546 | 3/2001 |
| WO | WO0134027 | 5/2001 |
| WO | WO0163561 | 8/2001 |
| WO | WO0174238 | 10/2001 |
| WO | WO0185022 | 11/2001 |
| WO | WO0241760 | 5/2002 |
| WO | WO02067201 | 8/2002 |
| WO | WO02082065 | 10/2002 |
| WO | WO03061454 | 7/2003 |

(56) References Cited

FOREIGN PATENT DOCUMENTS

| WO | WO03088133 | 10/2003 |
|----|------------|---------|
| WO | WO03090171 | 10/2003 |
| WO | WO03098539 | 11/2003 |
| WO | WO04019782 | 3/2004 |
| WO | WO04020996 | 3/2004 |
| WO | WO04020997 | 3/2004 |
| WO | WO04034087 | 4/2004 |
| WO | WO04044848 | 5/2004 |
| WO | WO04066215 | 8/2004 |
| WO | WO04072906 | 8/2004 |
| WO | WO05071601 | 8/2005 |
| WO | WO09029636 | 3/2009 |
| WO | WO09067675 | 5/2009 |
| WO | WO09067680 | 5/2009 |
| WO | WO11065929 | 6/2011 |
| WO | WO2015063188 | 5/2015 |

OTHER PUBLICATIONS

Boone et al., Recognition of Chest Radiograph Orientation for Picture Archiving and Communications Systems Display Using Neural Networks, J. Digital Imaging, 1992, 5(3), 190-193.

Boone et al., Automated Recognition of Lateral from PA Chest Radiographs: Saving Seconds in a PACS Environment, J. Digital Imaging, 2003, 16(4), 345-349.

Luo et al., Automatic Image Hanging Protocol for Chest Radiographs in a PACS, IEEE Transactions on Information Technology in Biomedicine, 2006, 10(2), 302-311.

Cabral et al., Accelerated Volume Rendering and Tomographic Reconstruction Using Texture Mapping Hardware•, Silicon Graphics Computer Systems, 1995 IEEE, DD. 91-97.

Carr, Nathan A., Jesse D. Hall, John C. Hart, The ray engine, Proceedings of the ACM SIGGRAPH/Eurographics conference on Graphics hardware, Sep. 1-2, 2002, pp. 37-46.

Chidlow, et al, Rapid Emission Tomography Reconstruction, Proceedings of the 2003 Eurographics/IEEE TVCG Workshop on Volume Graphics, Tokyo, Japan, Jul. 7-8, 2003, 13 pages.

Cohen, Michael, et al., A Progressive Refinement Approach to Fast Radiosity Image Generation, Computer Graphics, vol. 22, No. 4, Aug. 1988, pp. 75-84.

Corner, B., University of Nebraska-Lincoln, MatLab.txt, 2003, 1 page.

Dachille, et al., High-Quality Volume Rendering Using Texture Mapping Hardware, Siggraph/Eurographics Hardware Workshop (1998) (8 pages).

Dempster, et al., Maximum Likelihood From Incomplete Data via the EM Algorithm, Harvard University and Educational Testing Service, Dec. 8, 1976, pp. 1-38.

Dennis, C, et al.,, Overview of X-Ray Computed Tomography, http://www.howstuffworks.com/framed.htm?parent=c . . . tm&url=http://www.ctlab.geo.utexas.edu/overview/, Dec. 26, 2002, 5 pages.

Dobbins, et al., Digital X-Ray Tomosynthesis: Current State of the Art and Clinical Potential, Physics in Medicine and Biology, vol. 48, pp. R65-R106 (2003).

Doggett, Michael, ATI, Programmability Features of Graphics Hardware, (paper) Apr. 23, 2002, pp. C1-C22.

Doggett, Michael, ATI, Programmability Features of Graphics Hardware, (slideshow) slides 1-62 31 pages.

Du, H., Sanchez-Elez, M., Tabrizi, N., Bagherzadeh, N., Anido, M. L., and Fernandez, M. 2003. Interactive ray tracing on reconfigurable SIMD MorphoSys. In Proceedings of the 2003 Conference on Asia South Pacific Design Automation (Kitakyushu, Japan, Jan. 21-24, 2003). ASPDAC. ACM, New York, NY, 471-476.

Eldridge Matthew, Homan Igehy, Pat Hanrahan, Pomegranate: a fully scalable graphics architecture, Proceedings of the 27th annual conference on Computer graphics and interactive techniques, p. 443-454, Jul. 2000.

Fang, L., et al., Fast Maximum Intensity Projection Algorithm Using Shear Warp Factorization and Reduced Resampling, Mangetic Resonance in Medicine 47:696-700 (2002).

Filtered Backprojection Reconstruction, http://www.physics.ubd.ca/-mirg/home/tutorial/fbDrecon.html, 216/2003, 5 pages.

Goddard et al., High-speed cone-beam reconstruction: an embedded systems approach, 2002, SPIE vol. 4681, pp. 483-491.

Grass et al., Three-dimensional reconstruction of high contrast objects using C-arm image intensifier projection data, 1999, Computerized Medical Imaging and Graphics, 23, pp. 311-321.

Hadwiger, Markus, et al., Hardware-Accelerated High-Quality Reconstruction of Volumetric Data on PC Graphics Hardware, VRVis Research Center, Vienna, Austria, and Institute of Computer Graphics and Algorithms, Vienna University of Technology, Austria, 9 pages.

Hastreiter et al. (Integrated registration and visualization of medical image data, Proc. Computer Graphics International, Jun. 22-26, 1998, pp. 78-85).

Hopf, M., Ertl, T., Accelerating 3d Convolution Using Graphics Hardware, Proc. IEEE Visualization, 1999, 5 pages.

Hudson, et al., Accelerated Image Reconstruction Using Ordered Subsets of Projection Data, IEEE Transactions on Medical Imaging, vol. 13, No. 4, Dec. 1994, pp. 601-609.

Image Registration Slideshow, 105 pages.

Iterative definition, Merriam-Webster on-line dictionary, printed Aug. 26, 2010, 3 pages.

Jain, Anju, A Programmable Graphics Chip, pcquest.com, Jun. 18, 2001.

Jones et al., Positron Emission Tomographic Images and Expectation Maximization: A VLSI Architecture for Multiple Iterations per Second, Computer Technology and Imaging, Inc., 1988 IEEE, pp. 620-624.

Kajiya, J. T., Ray tracing volume densities, Proc. Siggraph, Jul. 1984, Computer Graphics, vol. 18, No. 3, pp. 165-174.

Karlsson, Filip; Ljungstedt, Carl Johan; Ray tracing fully implemented on programmable graphics hardware, Master's Thesis, Chalmers University of Technology, Dept. of Computer Engineering, Goteborg, Sweden, copyright © 2004, 29 pages.

Kruger J. and R. Westermann, Acceleration Techniques for GPU-based Volume Rendering, Proceedings of IEEE Visualization, 2003, 6 pages.

Lange et al., EM Reconstruction Algorithms for Emission and Transmission Tomography, J Computer Assisted Tomography 8, DD. 306, et seq. (1984).

Lange et al., Globally Convergent Algorithms for Maximum a Posteriori Transmission Tomography, IEEE Transactions on Image Processing, Vo. 4, No. 10, Oct. 1995, pp. 1430-1438.

Li et al., Tomographic Optical Breast Imaging Guided by Three-Dimensional Mammography, Applied Optics, Sep. 1, 2003, vol. 42, No. 25, pp. 5181-5190.

Li, et al., A Brick Caching Scheme for 30 Medical Imaging, Apr. 15-18, 2004, IEEE International Symposium on Biomedical Imaging: Macro to Nano 2004, vol. 1, pp. 563-566.

Maes, et al. Multimodality Image Registration by Maximization of Mutual Information, IEEE Tran. on Medical Imaging, vol. 16, No. 2, Apr. 1997. pp. 187-198).

Max, N., Optical Models for Direct Volume Rendering, IEEE Transactions on Visualization and Computer Graphics, Jun. 1995, 1(2): pp. 99-108.

McCool, M. et al., Shader Algebra, 2004, pp. 787-795.

McCool, Michael J., Smash: A Next-Generation API for Programmable Graphics Accelerators, Technical Report CS-200-14, Computer Graphics Lab Dept. of Computer Science, University of Waterloo, Aug. 1, 2000.

Microsoft, Architectural Overview Direct for 3D, http://msdn.microsoft.com/library/default.asp?url=/library/en-us/dx8_c/directx_cpp/Graphics/ProgrammersGuide/GettingStarted/Architecture, 12120/2002, 22 pages.

Mitchell, Jason L., RadeonTM 9700 Shading, Siggraph 2002—State of the Art in Hardware Shading Course Notes, DD.3.1-1-3.1-39, 39 pages.

Mitschke et al., Recovering the X-ray projection geometry for three-dimensional tomographic reconstruction with additional sensors: Attached camera versus external navigation system, 2003, Medical Image Analysis, vol. 7, pp. 65-78.

(56) References Cited

OTHER PUBLICATIONS

Mueller, K., and R. Yagel, Rapid 3-D Cone Beam Reconstruction With the Simultaneous Algebraic Reconstruction Technique (SART) Using 2-D Texture Mapping Hardware, IEEE Transactions on Medical Imaging, Dec. 2000, 19(12): pp. 1227-1237.
Navab, N., et al., 3D Reconstruction from Projection Matrices in a C-Arm Based 3D-Angiography System, W.M. Wells e al., eds., MICCAI'98, LNCS 1496, pp. 119-129, 1998.
Parker, S., et al., Interactive Ray Tracing for Isosurface rendering, IEEE, 1998, pp. 233-258.
PCT/US2008/084282, Preliminary and International Search Reports, dated May 11, 2011, 7 pages.
PCT/US2005/000837, Preliminary and International Search Reports, dated May 11, 2005, 7 pages.
PCT/US2008/74397, Preliminary and International Search Reports, dated Dec. 3, 2008, 7 pages.
PCT/US2008/84368, Preliminary and International Search Reports, dated Jan. 13, 2009, 7 pages.
PCT/EP2016/067886, Preliminary and International Search Reports, dated Jan. 17, 2017, 18 pages.
PCT/EP2018/075744, Preliminary and International Search Reports, dated Feb. 1, 2019, 17 pages.
PCT/US2008/84376, Preliminary and International Search Reports, dated Jan. 12, 2009, 6 pages.
JP2018-524544, Office Action, dated Jun. 2, 2020, 4 pages (& English translation).
JP2018-524544, Office Action, dated Nov. 4, 2020, 4 pages (& English translation).
AU2016299367, Office Action, dated Nov. 12, 2020, 4 pages.
EP3329405, Office Action, dated Apr. 6, 2020, 5 pages.
Pfister, H., et. al., The VolumePro real-time ray-casting System, Computer Graphics Proceedings of SIGGRAPH), Aug. 1999, No. 251-260.
Phong, B. T. Illumination for Computer Generated Pictures, Communications of the ACM, 18(6), Jun. 1975, pp. 311-317.
Porter, D. H. 2002. Volume Visualization of High Resolution Data using PC-Clusters. Tech. rep., University of Minnesota. Available at http://www.lcse.umn.edu/hvr/pc_vol_rend_L.pdf.
Potmesil, M. and Hoffert, E. M. 1989. The pixel machine: a parallel image computer. In Proceedings of the 16th Annual Conference on Computer Graphics and interactive Techniques SIGGRAPH '89. ACM, New York, NY, 69-78.
Purcell, T., et al., Real-time Ray Tracing on Programmable Graphics Hardware, Department of Computer Science, Stanford University, Stanford, CA, Submitted for review to SIGGRAPH 2002, 2002. http://graphics.stanford.edu/papers/rtongfx/rtongfx_submit.pdf.
Purcell, T., et. al., Ray tracings on Programmable Graphics Hardware, Computer Graphics (Proceedings of SIGGRAPH), 1998, pp. 703-712.
Purcell, Timothy J., Craig Donner, Mike Cammarano, Henrik Wann Jensen, Pat Hanrahan, Photon mapping on programmable graphics hardware, Proceedings of the ACM SIGGRAPH/Eurographics conference on Graphics hardware, Jul. 26-27, 2003, 11 pages.
Ramirez et al. (Prototypes stability analysis in the design of a binning strategy for mutual information based medical image registration, IEEE Annual Meeting of the Fuzzy Information, Jun. 27-30, 2004, vol. 2, pp. 862-866.
Rib Cage Projection, downloaded from http://www.colorado.edu/physics/2000/tomography/final_rib_cage.html on Dec. 26, 2002, 3 pages.
Roettger, Stefan, et al., Smart Hardware-Accelerated Volume Rendering, Joint Eurographics—IEEE TCVG Symposium on Visualization, 2003, pp. 231-238, 301.
Sandborg, Michael, Computed Tomography: Physical principles and biohazards, Department of Radiation Physics, Faculty of Health Sciences, Linkoping University, Sweden, Report 81 ISSN 1102-1799, Sep. 1995 ISRN ULI-RAD-R--81--SE, 18 pages.
Sarrut et al. (Fast 30 Image Transformations for Registration Procedures, Proc. Int. Conf. on Image Analysis and Processing, Sep. 27-29, 1999, pp. 446-451.
Selldin, Hakan, Design and Implementation of an Application Programming Interface for Volume Rendering, Linkopings Universitet.
Shekhar, R.; Zagrodsky, V., Cine MPR: interactive multiplanar reformatting of four-dimensional cardiac data using hardware-accelerated texture mapping, IEEE Transactions on Information Technology in Biomedicine, vol. 7, No. 4, pp. 384-393, Dec. 2003.
Silver, et al., Determination and correction of the wobble of a C-arm gantry, Medical Imaging 2000: Image Processing, Kenneth M. Hanson, ed., Proceedings of SPIE vol. 3970 (2000).
Stevens, Grant, et al., Alignment of a Volumetric Tomography System, Med. Phys., 28 (7), Jul. 2001.
Tao, W., Tomographic mammography using a limited number of low dose cone beam projection images, Medical Physics, AIP, Melville, NY vol. 30, pp. 365-380, Mar. 2003, ISSN: 0094-2405.
Tasdizen, T., Ross Whitaker, Paul Burchard, Stanley Osher, Geometric surface processing via normal maps, ACM Transactions on Graphics (TOG), v.22 n.4, p. 1012-1033, Oct. 2003.
Tasdizen, T.; Whitaker, R.; Burchard, P.; Osher, S.; Geometric surface smoothing via anisotropic diffusion of normals, IEEE Visualization, VIS 2002, Nov. 2002, pp. 125-132.
Technical Brief: NVIDIA nfiniteFX Engine: Programmable Pixel Shaders, NVIDIA Corporation, 5 pages.
Technical Brief: NVIDIA nfiniteFX Engine: Programmable Vertex Shaders, NVIDIA Corporation, 12 pages.
Viola, I, et al., Hardware Based Nonlinear Filtering and Segmentation Using High Level Shading Languages, Technical Report TR-186-2-03-07, May 2003, 8 pages.
Viola, P., Alignment by Maximization of Mutual Information, PhD Thesis MIT (Also Referred to as—AI Technical report No. 1548), MIT Artificial Intelligence Lab, Jun. 1, 1995, pp. 1-29.
Weiler, M, M. Kraus and T. Ertl, Hardware-Based View-Independent Cell Projection, Proceedings IEEE Symposium on Volume Visualization 2002, pp. 13-22.
Weiler, M. et al., Hardware-based ray casting for tetrahedral meshes, IEEE Visualization, VIS 2003, Oct. 24-24, 2003, pp. 333-340.
Weiler, M. et al., Hardware-Based view-Independent Cell Projection, IEEE, 2002, pp. 13-22.
Weiskopf, D., T. Schathitzel, T. Ertl, GPU-Based Nonlinear Ray Tracing, Eurographics, vol. 23, No. 3, Aug. 2004.
Wen, Junhai; Zigang Wang; Bin Li; Zhengrong Liang; An investigation on the property and fast implementation of a ray-driven method for inversion of the attenuated Radon transform with variable focusing fan-beam collimators, 2003 IEEE Nuclear Science Symposium Conference Record, vol. 3, Oct. 19-25, 2003, pp. 2138-2142.
Wikipedia, Anonymous, 'Volume Rendering' May 30, 2015, retrieved Nov. 4, 2016, https://en.wikipedia.org/w/index.php?title=Volume_rendering&oldid=664765767.
Wikipedia, Anonymous, 'Tomographic Reconstruction' Dec. 6, 2014, retrieved Nov. 4, 2016, https://en.wikipedia.org/w/index.php?title=Tomographic_Reconstruction&oldid=636925688.
Wu et al., Tomographic Mammography Using a Limited Number of Low-dose Conebeam Projection Images, Med. Phys., pp. 365-380 (2003).
Xu et al., Toward a Unified Framework for Rapid 30 Computed Tomography on Commodity GPUs, Oct. 19-25, 2003, IEEE Nuclear Science Symposium Conference 2003, vol. 4, pp. 2757-2759.
Xu et al., Ultra-fast 30 Filtered Backprojection on Commodity Graphics Hardware, Apr. 1-18, 2004, IEEE International symposium on Biomedical Imaging: Macro to Nano, vol. 1, pp. 571-574 and corresponding power point presentation.

\* cited by examiner

APPARATUS AND SYSTEM FOR RULE BASED VISUALIZATION OF DIGITAL BREAST TOMOSYNTHESIS AND OTHER VOLUMETRIC IMAGES

PRIORITY CLAIM

This application is a continuation of (1) U.S. application Ser. No. 16/985,986 entitled Method and System for Rule Based Visualizing Digital Breast Tomosynthesis and Other Volumetric Images, filed Aug. 5, 2020, which claims priority to and is a continuation of (2) U.S. application Ser. No. 16/531,413 entitled Method and System for Rule Based Visualizing Digital Breast Tomosynthesis and Other Volumetric Images, filed Aug. 5, 2019, which issued as U.S. Pat. No. 10,820,877, which claims priority to and is a continuation of (3) U.S. application Ser. No. 16/049,801 entitled Method and System for Rule Based Visualizing Digital Breast Tomosynthesis and Other Volumetric Images, filed Jul. 30, 2018, which issued as U.S. Pat. No. 10,631,812, which claims priority to and is a continuation of (4) U.S. application Ser. No. 15/220,325 entitled Method and System for Rule Based Visualizing Digital Breast Tomosynthesis and Other Volumetric Images, filed Jul. 25, 2016, which issued as U.S. Pat. No. 10,070,839, which claims priority to and is a continuation in part of (5) U.S. application Ser. No. 14/611,163 filed Jan. 30, 2015, which issued as U.S. Pat. No. 9,524,577 which is a continuation of (6) U.S. application Ser. No. 13/831,975 filed Mar. 13, 2013, which issued as U.S. Pat. No. 8,976,190, where (4) also claims priority to (7) U.S. Provisional application No. 62/197,956 filed Jul. 28, 2015. The specification and drawings of (1)-(7) are herein expressly incorporated by reference in their entireties and for all purposes.

FIELD OF INVENTION

The invention pertains to rule based ways of viewing volumetric images used for medical diagnosis.

BACKGROUND OF THE INVENTION

In order to diagnose a traditional X-Ray examination, the images printed on films would be 'hung' in front of a light box. For multi-image examinations, as well as for comparison with priors, the 'hanging' would often follow a specific protocol. For example, a particular organization or doctor may choose for a two-view chest X-Ray with a two-view prior exam, that the films be hung from left to right as follows: Frontal view of current examination, lateral view of current examination, frontal view of prior examination, lateral view of prior examination. In contrast, the doctor may hang mammography exams with the corresponding views of current and prior next to each other, if that was more appropriate for the diagnostic workflow in that case. Thus, the organization or doctor developed a traditional 'Hanging Protocol'. Currently, the film and the light box are often being replaced by computer systems, called PACS (Picture Archiving and Communication System). PACS systems can mimic the Hanging Protocols.

Traditional X-Ray examinations typically produce one or a small number of single two dimensional (2D) images. In contrast, the more advanced imaging modalities such as Computer Tomography (CT), Magnetic Resonance Imaging (MRI) or Positron Emission Tomography (PET) can produce dozens of series, each consisting of a hundred or more images. It is possible and not uncommon to review images from these advanced modalities in the same manner as traditional X-Ray images, i.e., by hanging the individual images side-by-side, either on a light-box or using a PACS system.

Volumetric images play an increasingly important role in medical diagnosis including cancer treatments such as site directed chemotherapy and radiology. Volumetric images are being generated by a multitude of different devices, including Magnetic Resonance Imaging (MRI) scanners, see for example Nuclear magnetic resonance imaging apparatus, U.S. Pat. No. 4,534,358, or Computed Tomography (CT) scanners, see for example Patients' support installation for a tomographic X-ray apparatus, U.S. Pat. No. 3,974,388, or certain C-Arm devices, see for example C-Arm computerized tomography system, U.S. Patent Application Publication No. 2010/0284601.

A certain class of these modalities, such as the CT scanner computes the volumetric images from a series of 2D projections from different angles, see for example (i) Methods and Apparatus for Reconstruction of 3D Image Volumes From Projection Images, U.S. Pat. No. 7,876,944; (ii) Method of Reconstructing Computer Tomography (CT) Volumes Suitable for Execution on Commodity Central Processing Units (CPUS) and Graphics Processors, and Apparatus Operating in Accordance with those Methods, U.S. Pat. No. 7,778,392 and (iii) Method of Reconstructing Computer Tomography (CT) Volumes Suitable for Execution on Commodity Central Processing Units (CPUS) and Graphics Processors, and Apparatus Operating in Accordance with those Methods, U.S. Pat. No. 8,107,592, which references (i)-(iii) are herein expressly incorporated by reference in their entireties.

A recent advance in the field is the development of a Digital Breast Tomosynthesis (DBT) scanner which generates volumetric mammography images, see for example Integrated multi-mode mammography/tomosynthesis x-ray system and method, U.S. Pat. No. 7,869,563, which is herein expressly incorporated by reference in its entirety Similar to CT or C-Arm devices, the DBT devices acquire a number of 2D X-Ray images, or 2D projections, from different angles. From these projections a volumetric image is computed

SUMMARY OF THE INVENTION

The invention pertains to digital data processing and, more particularly, by way of example, to the visualization of image data. Three dimensional (3D) and four dimensional (4D) image data is routinely acquired with CT, MRI, PET, confocal microscopes, 3D ultrasound devices, and other imaging devices. The medical imaging market is just one example of a market that uses these devices. The visualization of image data market is growing rapidly, with new CT scanners collecting larger amounts of data more quickly than previous generation CT scanners. The invention has application to areas including medical imaging, atmospheric studies, astrophysics and geophysics.

With the rapid increase in the amounts and types of information that can be acquired using imaging technology, we have identified an advantage in presenting volumetric image-based information in a form that can be used by a physician or diagnostician. Namely, although there may be many different types of image data, the forms, formats, integration, and display of relevant information can be optimized for diagnosis.

In an embodiment of the present invention, a method for displaying volumetric images comprises computing a projection image using a viewing direction, displaying the projection image and then varying the projection image by varying the viewing direction. In an embodiment of the present invention, the viewing direction can be varied based on a periodic continuous mathematical function. In an embodiment of the present invention, a graphics processing unit (GPU) can be used to compute the projection image and bricking can be used to accelerate the computation of the projection images. In another embodiment of the present invention, a sequence of projections covering one period can be rendered, cached and then played back one or more times, where the rendering is carried out on a server and the caching and play back is carried out on a client computer. A render server program is described in U.S. application Ser. No. 13/831,967, entitled 'Multi-User Multi-GPU Render Server Apparatus and Methods', which was filed Mar. 15, 2013 is herein expressly incorporated by reference in its entirety. A rule based render server program is described in 'Method and System for Rule-Based Display of Sets of Images' which issued as U.S. Pat. No. 8,976,190 on Mar. 10, 2015, and is herein expressly incorporated by reference in its entirety. In an alternative embodiment of the present invention, the viewing direction can be varied based on user input. In a different embodiment of the present invention, a system that displays two or more volumetric images by computing a projection image of each of the volumetric images, using the same viewing direction v for each volumetric image, displaying each projection images, and varying the projection image by varying the viewing direction, where the varied viewing direction is changed in the same way for each of the projections. In an embodiment of the present invention, the volumetric images are computed from a number of 2D X-Ray images, or 2D projections, from different angles generated by a DBT device. In an embodiment of the present invention, volumetric mammography images are displayed. In an alternative embodiment of the present invention, volumetric images are computed from a number of 2D X-Ray images generated by angiography. In an embodiment of the present invention, the volumetric cerebral angiography images of the human brain are displayed. In another alternative embodiment of the present invention, volumetric images are computed from a confocal microscope using antibody staining. In an embodiment of the present invention, volumetric cell tissue generated by the confocal microscope is displayed.

These and other aspects of the invention are evident in the drawings and in the description that follows

BRIEF DESCRIPTION OF THE DRAWINGS

This invention is described with respect to specific embodiments thereof. Additional features can be appreciated from the Figures in which:

FIG. 12A shows an example of a user interface to specify rules including a dialog box to configure Study Selection rules applied to a prior chest CR, according to an embodiment of the invention;

FIG. 12B shows an example of a user interface to specify rules including a dialog box to configure Study Selection rules applied to a prior left breast mammogram, according to an embodiment of the invention;

DETAILED DESCRIPTION OF THE INVENTION

Definitions

Figure 1A:
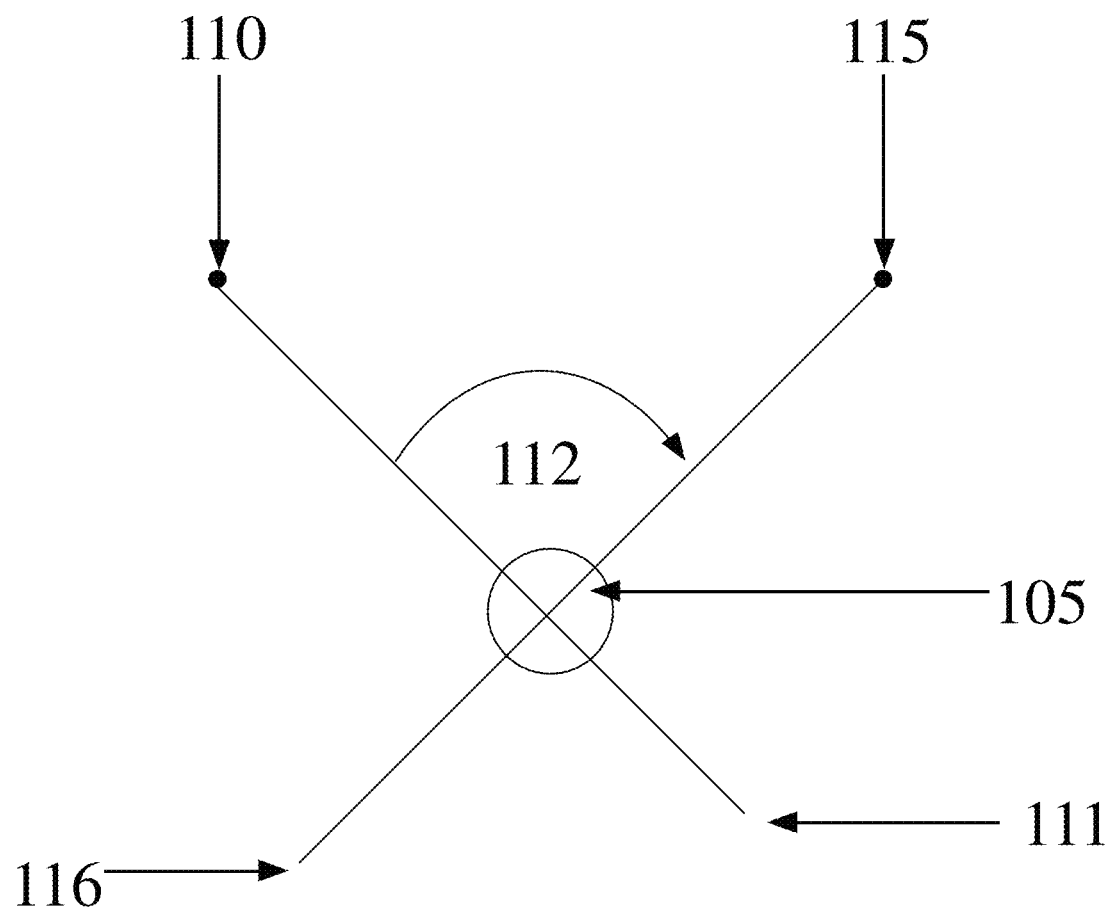
FIG. 1A shows the specimen imaged using an X-Ray source from two positions spanning an angular range.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term 'bandwidth' and 'send bandwidth' refer to various bit-rate measures, representing the available or consumed data communication resources expressed in bits per second or multiples of it.

The phrase 'adaptive bandwidth management' means methods that continuously adjust the amount of data that is sent into a network per time in order to avoid or reduce network congestion and transfer delay.

The term 'client-server' refers to a computer system that selectively shares its resources with 'clients'. A 'client' is a computer or computer program that initiates contact with a 'client-server' or 'server' in order to make use of the server resources. A client-server can be especially useful to undertake volume rendering tasks. Such a server can have one or more graphics processing units. Further, by sharing the server's computer resources, multiple clients can access and use the server resources at the same time. Because a computer does a limited amount of work at any moment, a time-sharing system must quickly prioritize its tasks to accommodate the clients. Clients and servers exchange messages in a request-response messaging pattern: The client sends a request, and the server returns one or multiple responses, synchronously or asynchronously.

The term 'video' means the display of three (3) or more 2-D projection images where there is a time delay between the first 2-D projection image and a second 2-D projection image and a time delay between the second 2-D projection image and a third 2-D projection image. A video may be displayed using a number of formats including avi, flv, H.262, H.263, H.264, m4v, mov, MPEG-1, MPEG-1 Part 2, MPEG-2, MPEG-4 Part 2, nsv, ogv, roq, vp6, vp8, vp9, webm, and wmv.

The phrase 'host computer' means a server or other processor with associated memory. In an embodiment of the invention, a host computer is enabled to provide measured 2-D projection images to a client.

The term 'caching' means storing in memory. A generated projection image from a volumetric image can be cached in one or both a client associated memory and a server associated memory, where the memory can be accessed rapidly by either the client processor or the server processor respectively.

The phrase 'measured 2-D projection image' means a two-dimensional (2-D) scan of biological tissue produced by forward-projection or back-projection of medical imaging equipment as described in U.S. Pat. No. 8,107,592 to A. Berman, and U.S. Pat. No. 7,876,944 to D Stalling et al.

The phrase 'volumetric image' refers to a three-dimensional (3-D) representation reconstructed from the data produced from a series of measured 2-D projection images or other 2-D representations of a tissue, an organ or an entity.

The term 'reconstruction' means generating a 3-D volumetric image based on a plurality of measured 2-D projection images. The phrase 'reconstruction of a volumetric image' means calculating a 3-D volumetric image based on a plurality of measured 2-D projection images.

The term 'generated' means constructing one or more generated 2-D projection images from a 3-D volumetric image. The phrase 'generating an image' or means 'generating a plurality of images' means constructing one or more generated 2-D projection images from a 3-D volumetric image. In an embodiment of the invention, the one or more generated 2-D projection images can be generated at different viewing directions.

The phrase 'viewing direction' means the line constructed passing through a viewing position to an object. As the designated position changes, the viewing direction changes. As shown in FIG. 1A a first viewing direction 111 is generated by the line between position 110 and the object 105. A second viewing direction 116 is generated by the line between position 115 and the object 105. The angle (θ) between the first viewing direction 111 and the second viewing direction 112 increases from 0 to θ. The smallest viewing direction is when the angle=0. The largest viewing direction is when the angle=θ.

The phrase 'equivalent viewing direction' means the same viewing direction in the absence of physiologic changes in the tissue or an equivalent viewing direction when physiologic changes have occurred or a comparable tissue is utilized, where the equivalent viewing direction can compensate for changes in the tissue in the body with time and/or can compensate for the symmetry and asymmetry of different tissue in the body. The equivalent viewing direction can be used to ascertain the presence or absence of physiologic changes in the tissue with time, or when physiologic changes have occurred based on the inspection of a comparable tissue. The equivalent viewing direction can compensate for changes in the tissue in the body with time and/or can compensate for the symmetry and asymmetry of viewing projection images of different tissues in the body.

The phrase 'improves the visual clarity of identification' means a process or technique that compares or changes one or more projection images to allow an obstruction including a micro calcification to be identified in the one or more projection images.

The term 'Study' will be used to refer to the set of images produced by an examination. A Study consists of one or more images. The images can be grouped into one or more image series. Each image, each series, and the whole Study can have different parameters attached. For medical images these can be defined by the Digital Imaging and Communication in Medicine (DICOM) standard.

The phrase 'Hanging Protocol' will be used to refer to specific conventions how X-Ray films are arranged (hung) at a light box.

The phrase 'Display Protocol' will be used to refer to the way images are displayed in a computer system, specifically the selection of the images to be displayed, the layout of the images, as well as the rendering parameters and styles.

The term 'Viewport' will be used to refer to the logical part of the screen on the client computer in which a particular View is displayed, for example the user interface on the client computer can contain four rectangular Viewports 1160 of which three show a frontal, left, and bottom view respectively of a particular data, while the fourth viewer might show a 2D cross section through the same or a different data set.

The phrase 'Sets of Images' or 'Image Set' will be used to refer to one or more images, selected based on the rules.

The phrase 'Study Selection Rules' will be used to refer to the rules used to select the studies to be displayed.

The phrase 'Protocol Selection Rules' will be used to refer to the rules used to select the layout of the images to be displayed.

The phrase 'Image Set Rules' will be used to refer to the rules used to form Image Sets 1165 from the images of one or more Study by applying selection, sorting, and breaking rules.

The phrase 'Style Rules' will be used to refer to the rules to determine which rendering type, rendering style, and rendering parameters are used for a particular Image Set 1165 in a particular viewer.

The phrase 'Volume Rendering' will be used to refer to Volume Rendering techniques including shaded Volume Rendering techniques, maximum intensity projection (MIP), oblique slicing or multi-planar reformats (MPR), axial/sagittal and coronal slice display, and thick slices (also called slabs). In medical imaging, for example, Volume Rendering is used to display 3D images from 3D image data sets, where a typical 3D image data set is a large number of 2D slice images acquired by a CT or MRI scanner and stored in a data structure.

The terms 'brick' or 'bricking' mean partitioning a 3D image or a portion of the 3D image. Bricking is an iterative process involving determining the intensity of pixels in the 2D image based on the rule that all points in the 3D image data that are required for evaluating the intensities of the sample points along a ray passing through a brick are located within that brick. That is in an imaging apparatus having a CPU and a GPU with a plurality of programmable vertex shaders coupled to a plurality of programmable pixel shaders, the CPU partitions the 3D image into a plurality 'bricks' based on the vertex shaders and pixel shaders determining the intensities of one or more pixels in the 2D image as an iterative function of intensities of sample points in one or more bricks in the 3D image through which viewing rays associated with those pixels are passed, and where any two adjacent bricks preferably have a sufficient overlap such that all points in the 3D image data that are required for evaluating the intensities of the sample points along a ray passing through a brick are located within that brick.

The term 'display' means in the context of aspects and embodiments disclosed herein and refers in the usual and customary sense to physical representation of data e.g. a printed page or an electronic representation on a visual display monitor, a cathode ray oscilloscope, a liquid crystal display, a nixie tube, a light emitting diode display, a plasma display and the like. The display of sensitive information can be anonymized as described in U.S. patent application Ser. No. 15/218,993 titled 'Method and Apparatus for Anonymized Display and Data Export' filed Jul. 25, 2016 inventors D. Stalling et al., the specification and drawings of which are herein expressly incorporated by reference in their entirety.

The terms 'view' or 'viewing' mean a display of a 3D or 2D image.

The phrases 'viewing position' or 'viewing ray' refer to a display of a 3D or 2D image as observed from the viewing position or along a line defined by the viewing ray.

The term 'identifies' refers to a 3D or 2D image corresponding to a view that is displayed and/or compared with other views that reveals or more clearly elucidates a microcalcification or obstruction through one or more processes selected from the group consisting of: observation by the human eye, identification by a segmentation algorithm, identification by a bricking algorithm.

The term 'microcalcification' refers to small deposits of calcium typically seen in a breast mammogram which depending on shape, number, pattern and/or relative position can be used as an early sign of breast cancer and/or presenting sign of breast cancer.

The term 'obstruction' means a filling defect or other ductal abnormality, such as ductal ectasia, fibrocystic changes or a ductal irregularity such as can be observed with ductography of the breast including galactography and ductogalactography.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes. Furthermore, it will also be apparent that the present invention is not limited to any particular software programming language or programming paradigm.

Receiving a Volumetric Image.

A computed tomography (CT) scan can generate many 2-D images taken from different angles around a scanned object to produce cross-sectional (tomographic) images ('virtual slices') of the scanned object. Alternatively, positron emission tomography (PET), single photon emission computed tomography (SPECT), computer assisted tomography (CAT) scanners or tomosynthesis systems can produce 'measured projection images'. These measured 2-D projection images can be used to reconstruct a 'volumetric image', where the virtual slices form a volumetric image or 3-D image of the scanned object. The phrase 'volumetric image' refers to a 3-D representation reconstructed from the data produced by forward-projecting or back-projecting medical imaging equipment. Measured projection images can be measured by medical technologists, and can be used to reconstruct a volumetric image and then the volumetric image can be received by a physician in order to diagnose a patient.

In an embodiment of the invention, using the reconstructed 3-D image it is possible to form a generated 2-D projection image, that is, a representation can be generated from a volumetric image by identifying a point source at a distinct focus and thereby a 'projection direction' through the volume to a plane at which the respective generated 2-D projection image can be formed, as described in U.S. patent application Ser. No. 15/218,972 titled 'Apparatus and Method for Visualizing Digital Breast Tomosynthesis and Other Volumetric Images' inventors M. Westerhoff et al., filed Jul. 25, 2016, the specification and drawings of which are herein expressly incorporated by reference in their entirety.

Computing a Plurality of Projection Images

One or more generated 2-D projection images can be generated from a volumetric image. Computing a plurality of generated 2-D projection images of the volumetric image using a plurality of viewing directions between a first viewing direction and a second viewing direction can be used to produce generated 2-D projection images required by a physician but otherwise not revealed by a measured 2-D projection image. Alternatively, by generating a plurality of generated 2-D projection images, a dynamic view of the volumetric image can be generated, which allows for better diagnosis than a single or static measured 2-D projection image or a single or static generated 2-D projection image.

Comparing a First Projection Image a Second Projection Image

The phrase 'time comparison' means comparing a projection image obtained at a specific viewing direction with an earlier in time projection image of a tissue obtained at an equivalent viewing direction of the same tissue. In an embodiment of the invention, a time comparison compares one or more projection images of a right breast with one or more projection images of the same right breast measured at an earlier time point, where the projection images are generated at equivalent viewing directions. In an embodiment of the invention, a time comparison compares one or more measured 2-D projection images of a right breast with one or more generated 2-D projection images of the same right breast generated from a volumetric image reconstructed from a plurality of measured 2-D projection images from an earlier time point, where the projection images are generated at equivalent viewing directions. In an alternative embodiment of the invention, a time comparison compares one or more generated 2-D projection images of a right breast with one or more measured 2-D projection images of the same right breast measured at an earlier time point, where the projection images are generated at equivalent viewing directions.

The phrase 'structural comparison' means comparing a projection image obtained at a specific viewing direction with a projection image of a tissue obtained at an equivalent viewing direction of a different but comparable tissue. In an embodiment of the invention, a structural comparison compares one or more projection images of a right breast with one or more projection images of a left breast both viewed at equivalent viewing directions. In an embodiment of the invention, a structural comparison compares one or more generated 2-D projection images of a right breast with one or more generated 2-D projection images of a left breast, where each of the generated 2-D projection images are viewed at equivalent viewing directions. In an alternative embodiment of the invention, a structural comparison compares one or more measured 2-D projection images of a right breast with one or more generated 2-D projection images of a left breast, where each of the measured and generated 2-D projection images are viewed at equivalent viewing directions. In another embodiment of the invention, a structural comparison compares one or more generated 2-D projection images of a right breast with one or more measured 2-D projection images of a left breast, where each of the measured and generated 2-D projection images are viewed at equivalent viewing directions.

The phrase 'dynamic comparison' means comparing a series of projection images obtained at a variety of viewing directions. In an embodiment of the invention, a dynamic comparison compares one or more DBT projection images of a right breast that change in time as the viewing direction is scanned as a video. In an embodiment of the invention, the change in viewing direction can adjust for the type of tissue being scanned.

The phrase 'visual comparison' means time comparing, structurally comparing, and/or dynamically comparing one or more projection images with the naked eye.

The phrase 'direct comparison' means one or more of time comparing, structurally comparing, and dynamically comparing one or more projection images using a computer to analyze changes in the intensity density of a voxel matrix represented by the projection images. In an embodiment of the invention, one or more generated 2-D projection images are compared with one or more measured 2-D projection images using one or more of time comparing, structurally comparing, and dynamically comparing, wherein a computer is used to analyze changes in the intensity density of a voxel matrix represented by the one or more generated 2-D projection images and the one or more measured 2-D projection images.

A first viewing direction 111 corresponds with the line between position 110 and the object 105. A second viewing direction 116 corresponds with line between position 115 and the object 105 (see FIG. 1A). The increment 112 is the angle between the first viewing direction 111 and the second viewing direction 112 (see FIG. 1A). By selecting a first viewing direction, a first generated 2-D projection image can be formed. Similarly, selecting a second viewing direction allows a second generated 2-D projection image at the second viewing direction to be formed. In an embodiment of the invention a first generated 2-D projection image can be dynamically compared with one or more second generated 2-D projection images. In an alternative embodiment of the invention a measured 2-D projection image can be dynamically compared with one or more generated 2-D projection images. In an alternative embodiment of the invention, a first projection image can be time compared with a second projection image measured at an earlier time. In another embodiment of the invention, a generated 2-D projection image can be time compared with a measured 2-D projection image measured at an earlier time. In another embodiment of the invention, a first projection image can be structurally compared with a second projection image of a control tissue. In another embodiment of the invention, a generated 2-D projection image can be structurally compared with a measured 2-D projection image of a control tissue. In an embodiment of the invention, a density map for the first projection image is visually compared with a density map of the second projection image. In an embodiment of the invention, a density map for a generated 2-D projection image is visually compared with a density map of a measured 2-D projection image. In an alternative embodiment of the invention, a computer program is used to directly compare the density map for the first projection image with a density map of the second projection image. In another alternative embodiment of the invention, a computer program is used to directly compare the density map for a generated 2-D projection image with a density map of a measured 2-D projection image.

Volume Rendering

Volume rendering, or reconstructing a volume, includes a variety of standard visualization methods including volume rendering techniques (VRT), shaded volume rendering techniques (sVRT), maximum intensity projection (MIP), oblique slicing or multiplanar reformats (MPR), axial/sagittal and coronal slice display, and thick slices (also called slabs). Within the scope of the invention, other methods and apparatus of forward-projection and back-projection can be used for generating a series of measured 2-D projection images with which to reconstruct 3-D volumetric image representations, as described in 'Client-Server Visualization System with Hybrid Data Processing' which issued as U.S. Pat. No. 9,019,287 Apr. 28, 2015, and which is herein expressly incorporated by reference in its entirety.

In an embodiment of the invention, a computer chip, chip set, computer board and/or computer processor can be configured as a 'graphics processing unit' (GPU) to perform volume rendering and or to generate one or more reconstructed 2-D projection views from a volumetric image. In an embodiment of the invention, volume rendering includes initializing to arbitrary values the volume density distribution in a voxel matrix, iteratively estimating and comparing with a measured projection, and then correcting each pixel based on the comparison as described in U.S. Pat. No. 7,876,944.

Intensity Values.

Image segmentation is an automated technique that facilitates distinguishing objects and other features in digital images. The technique can be used, for example, to simplify digitized images so that they can be more readily interpreted by computers (e.g., image analysis software) and/or by their users. An image can be made up of pixels containing a wide range of undifferentiated intensity values that although, possibly recognizable to the human eye as skeletal bones and digestive tract are largely uninterpretable by a computer. In an embodiment of the invention, a comparison between a first projection image with a second projection image that reveals an area of increased intensity values in the second projection image can indicate that the second viewing direction which generated the second projection image reveals an unobstructed projection image. In an alternative embodiment of the invention, a comparison between a generated 2-D projection image with a measured 2-D projection image that reveals an area of increased differentiated intensity values in the measured 2-D projection image can indicate that the viewing direction which formed the generated 2-D projection image reveals an unobstructed viewing direction. In an alternative embodiment of the invention, a comparison between a first projection image with a second projection image that reveals an area of increased differentiated intensity values in the second projection image can indicate that the second viewing direction which generated the second projection image reveals an increased clarity projection image, as described in U.S. Pat. No. 8,548,215, 'Automatic Image Segmentation of a Volume by Comparing and Correlating Slice Histograms with an Anatomic Atlas of Average Histograms' Oct. 1, 2013 and which is herein expressly incorporated by reference in its entirety. In an alternative embodiment of the invention, a comparison between a generated 2-D projection image with a measured 2-D projection image that reveals an area of increased differentiated intensity values in the measured 2-D projection image can indicate that the viewing direction which formed the generated 2-D projection image reveals an advantageous viewing direction.

Primary Study Versus Secondary Study

A primary study is a study carried out at a specified time point. A secondary study is a study carried out at a subsequent time point. In an embodiment of the invention, a computer chip, chip set, computer board and/or computer processor can be configured as a 'digital data processor' to perform volume rendering, to generate one or more projection views from a volume and or to compare two or more projection views. The digital data is generated by forward-projecting or back-projecting medical imaging equipment used to generate measured projection images or other 2-D representations. In an embodiment of the invention, a comparison between a generated 2-D projection image from a secondary study with a generated 2-D projection image from a primary study that reveals an area of increased differentiated intensity values can be used to assess the development or changes occurring over time. In an embodiment of the invention, a comparison between a generated 2-D projection image from a secondary study with a measured 2-D projection image from a primary study that reveals an area of increased differentiated intensity values in the measured 2-D projection image can indicate that the viewing direction which formed the generated 2-D projection image reveals an unobstructed viewing direction.

Overview

Due to the physical constraints of the acquisition setup, the possible angular range of the acquisition is often limited. Typically the angular range 112 is less than 180° in digital breast tomosynthesis (DBT) (see FIG. 1A). For mathematical reasons, this results in volumetric images with a non-isotropic resolution. More precisely, the resolution in the plane perpendicular to the average projection direction is much higher, than the reconstructed resolution in the average direction of the X-Ray beam.

This aspect has to be taken into account when designing viewing methods for such images. Given the reconstructed volumetric image, in the following the direction of the lowest resolution will be referred to as the z-direction, or z. The vectors defining the average detector orientation, i.e. the plane with the highest resolution are denoted as x, and y. The x, y, and z directions are mutually perpendicular to each other.

In order to display a volumetric image on a standard computer screen, which is two dimensional, a transformation has to be applied in order to compute a 2-D representation of the volumetric image.

For DBT viewing, a slicing transformation can be used, where a single slice perpendicular to the z-direction is shown on the screen. Typically a user interface, such as a slider or text input field, allows the user to select which slice can be shown. In the following this will be referred to as 'xy-slicing' or 'slicing'. While xy-slicing is an important viewing tool, it has some limitations. In particular it only takes into account a small subset of the information present in the volumetric data set.

The present invention overcomes the limitation of using only a small subset of the information by using a projection method to incorporate the entirety of the volumetric information. In an embodiment of the present invention, time is used as a third dimension to resolve ambiguities in a comprehensible and intuitive way.

From the volumetric image a projection can be computed. Let

I: $R^3 \rightarrow R$ be the volumetric image.

Let $\underline{v}$ e $R^3$ be a three dimensional vector defining a first viewing direction.

Let $\underline{i}_x$ and $\underline{i}_y$ be two vectors spanning a projection plane perpendicular to $\underline{v}$ and perpendicular to each other.

Then a projection $P(\underline{v},.)$ can be defined as follows:

$P(\underline{v},.): R^2 \rightarrow R$ $P(\underline{v},p) = \max(I(\underline{r})) | \underline{r}$ e $R^3$ where v dot $\underline{i}_x = p_1$, v dot $\underline{v}_y = p_2$ and $P(\underline{v},.)$ is a 2D image that can be displayed on a computer screen using standard methods.

Displaying $P(\underline{v},.)$ as defined above provides the user with additional diagnostic information as it takes into account the whole data set. For example if there was a lesion in the examined specimen and the volumetric image was viewed using xy-slicing then that lesion would only be visible in a subset of the slices at or around the z-position of the lesion. If the wrong z-position was chosen, the lesion can be missed. Therefore the user would have to examine each slice to be certain there was no lesion present, or alternatively risk overlooking a lesion. In an unexpected result, viewing a dynamic comparison in the form of a video can allow the information to be quickly and efficiently compared.

Figure 1B:
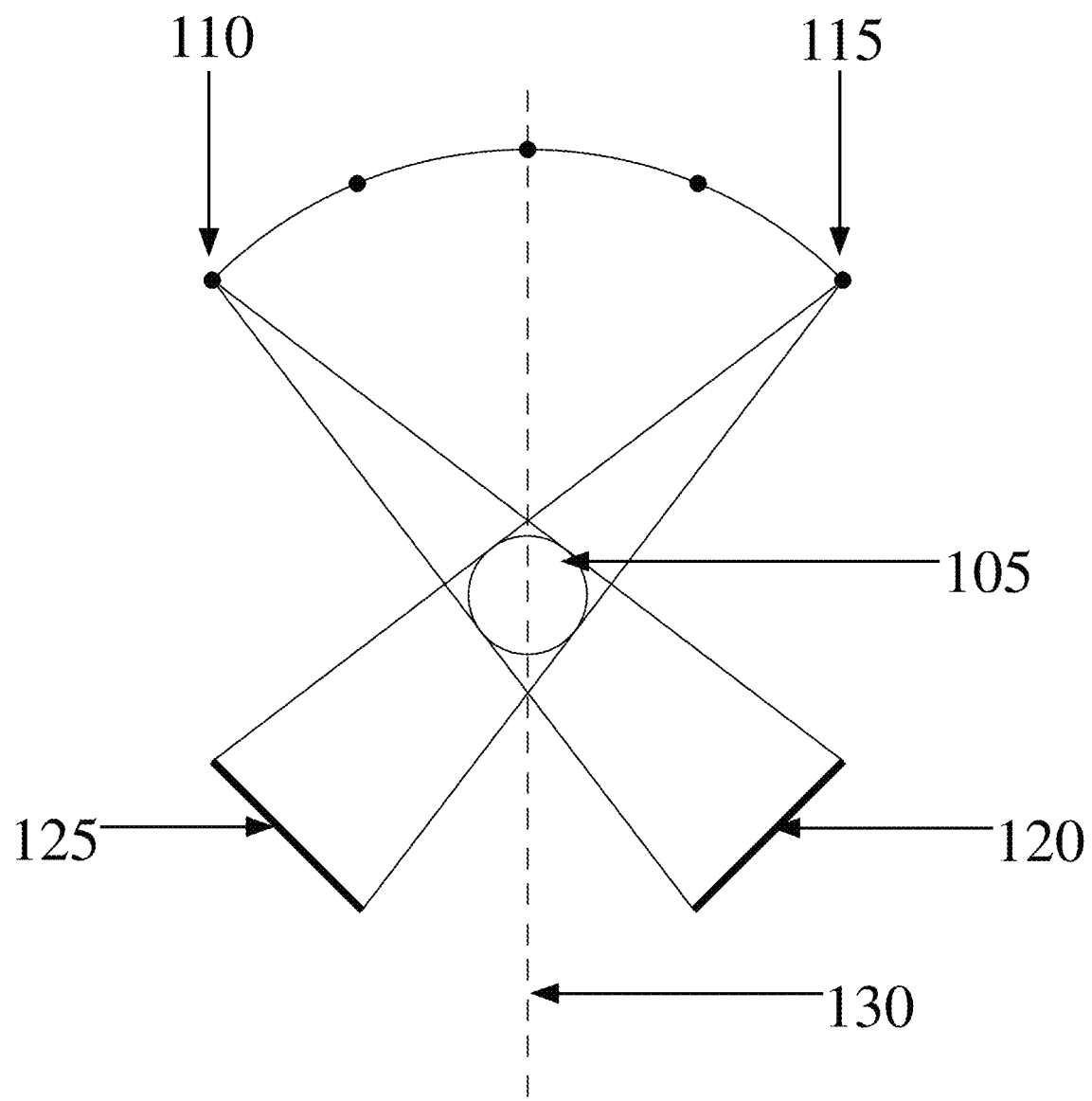
FIG. 1B shows the specimen imaged using an X-Ray source and an X-Ray detector from a multitude of positions. The positions span a certain angular range that is defined by the physical constraints of the machine and the patient's position.
Figure 2:
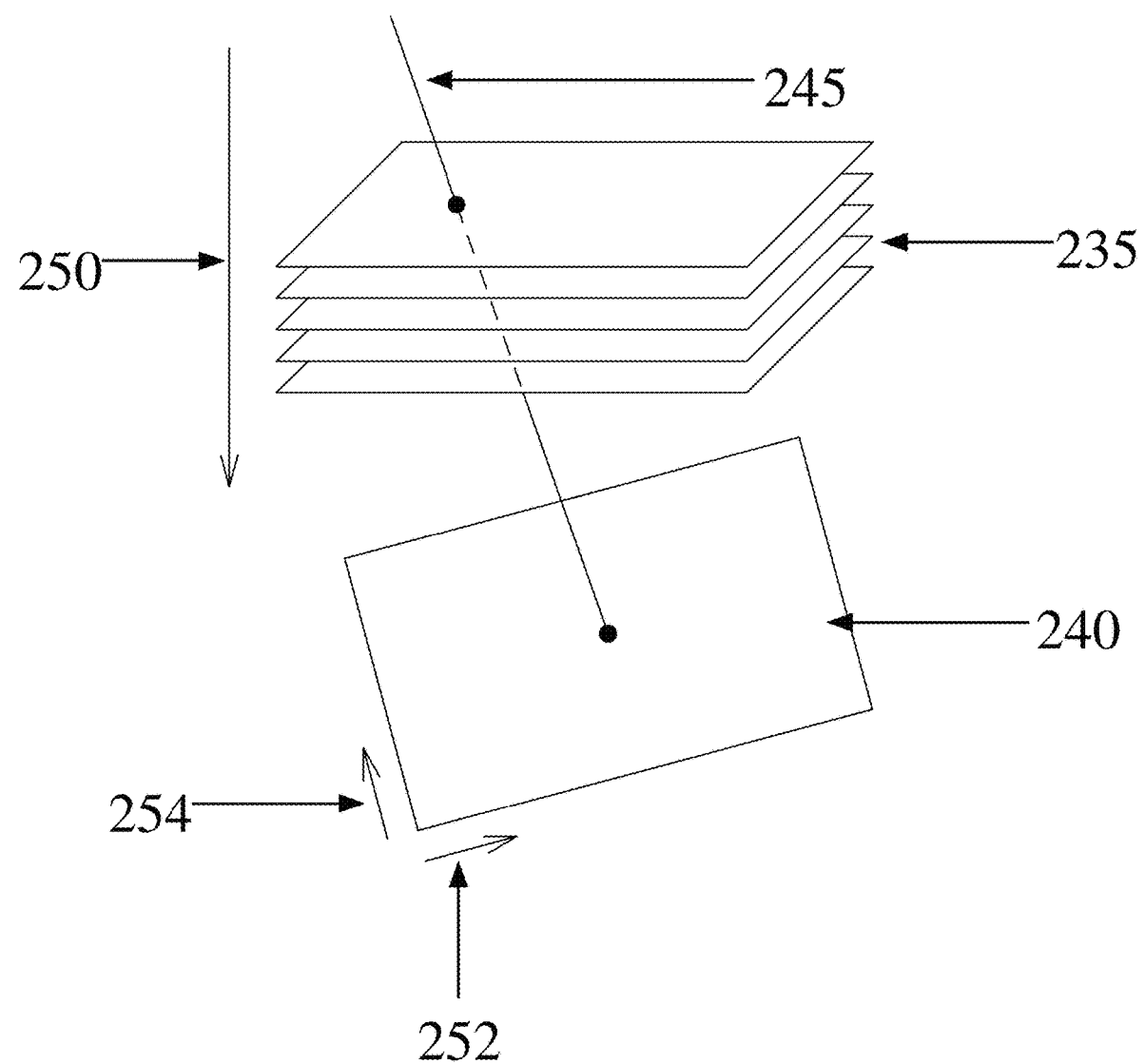
FIG. 2 illustrates the calculation of a projection P from the volumetric image I, where the projection is defined by the viewing direction v, which defines the Projection plane, according to an embodiment of the invention.

FIG. 1A shows a specimen 105 imaged from two positions 110, 115 spanning an angular range 112 which generate viewing directions 111, 116 respectively. FIG. 1B shows the principle of DBT. In FIG. 1B, the specimen 105 (e.g. a human breast) can be imaged using an X-Ray source and an X-Ray detector from a multitude of positions that lie on the arc beginning at position 110 and ending at position 115 and which are detected at detector positions 120 and 125, respectively. The average acquisition direction is indicated by the dotted line 130. The positions span a certain angular range that is defined by the physical constraints of the machine and the patient's position. The z vector ($\underline{z}$) 130 denotes the middle projection direction in that angular range. FIG. 2 illustrates the calculation of a projection P from the volumetric image I, 235. The projection is defined by the viewing direction $\underline{v}$ 245, which defines the projection plane 240. In general $\underline{v}$ 245 is not necessarily identical to the average acquisition direction $\underline{z}$ 250. The two vectors $\underline{i}_x$ 252 and $\underline{i}_y$ 254 are the x-direction and y-direction of the projection image P, respectively. The vectors $\underline{i}_x$ 252 and $\underline{i}_y$ 254 are perpendicular to the viewing direction $\underline{v}$ 245. The vector $\underline{i}_x$ 252 is perpendicular to the vector $\underline{i}_y$ 254, and can be chosen according to the users viewing preferences or automatically specified according to automated rules, as described in more detail in 'Method and System for Rule-Based Display of Sets of Images' issued as U.S. Pat. No. 8,976,190. Digital Imaging and Communication in Medicine (DICOM) parameters for making rule based decisions include the time of generation of the measured projection images, the type of tissue measured and whether the tissue has an equivalent control that can be used as a control. For example for mediolateral acquisition directions, the y-axis will typically be chosen such that it aligns with the projection of the patient's head-foot axis.

Figure 7A:
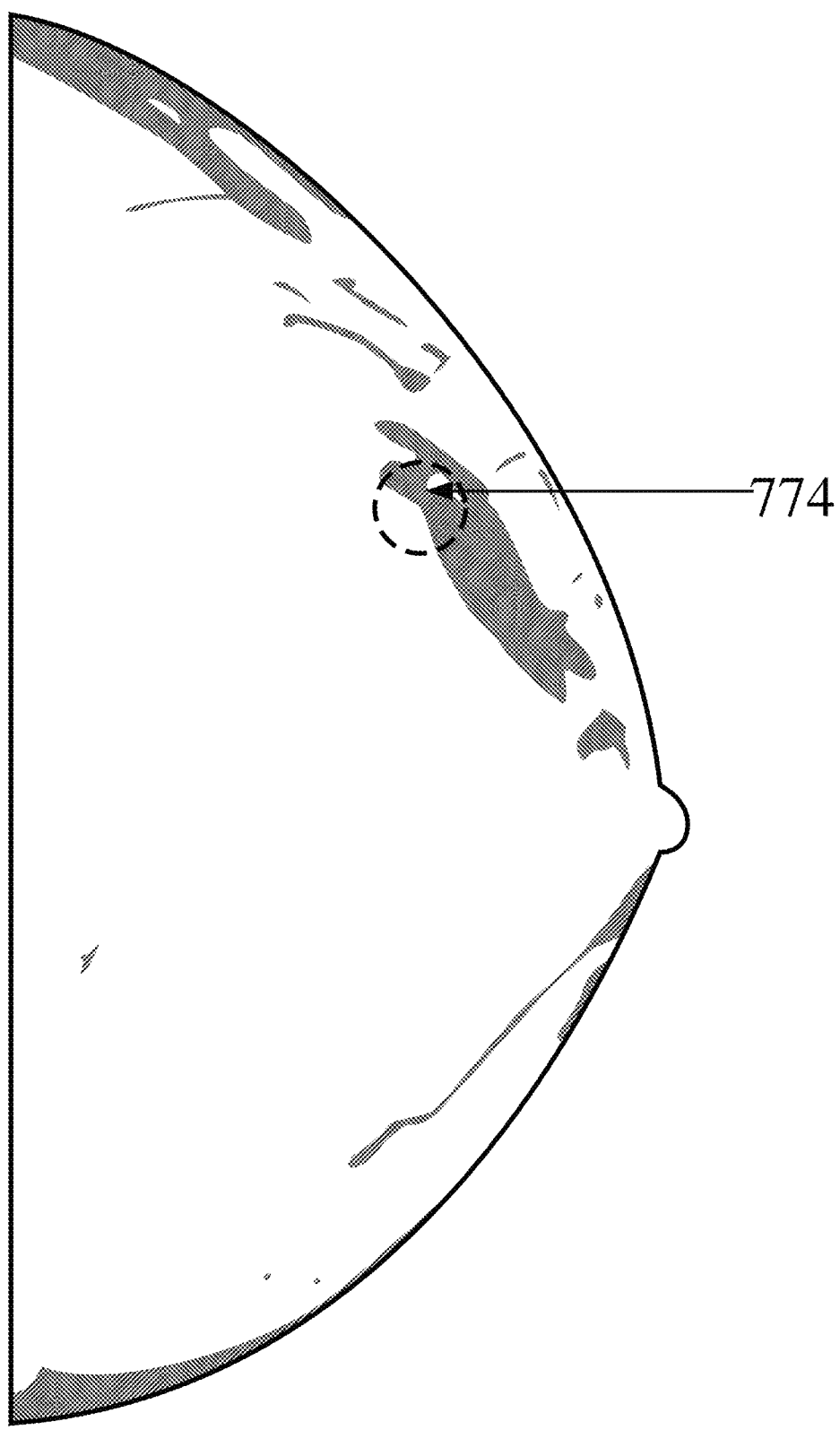
FIG. 7A shows an artists impression of an image of a human breast computed from a number of images recreated from a specific angle where a micro calcification is occluded by denser breast tissue, according to an embodiment of the invention.
Figure 7B:
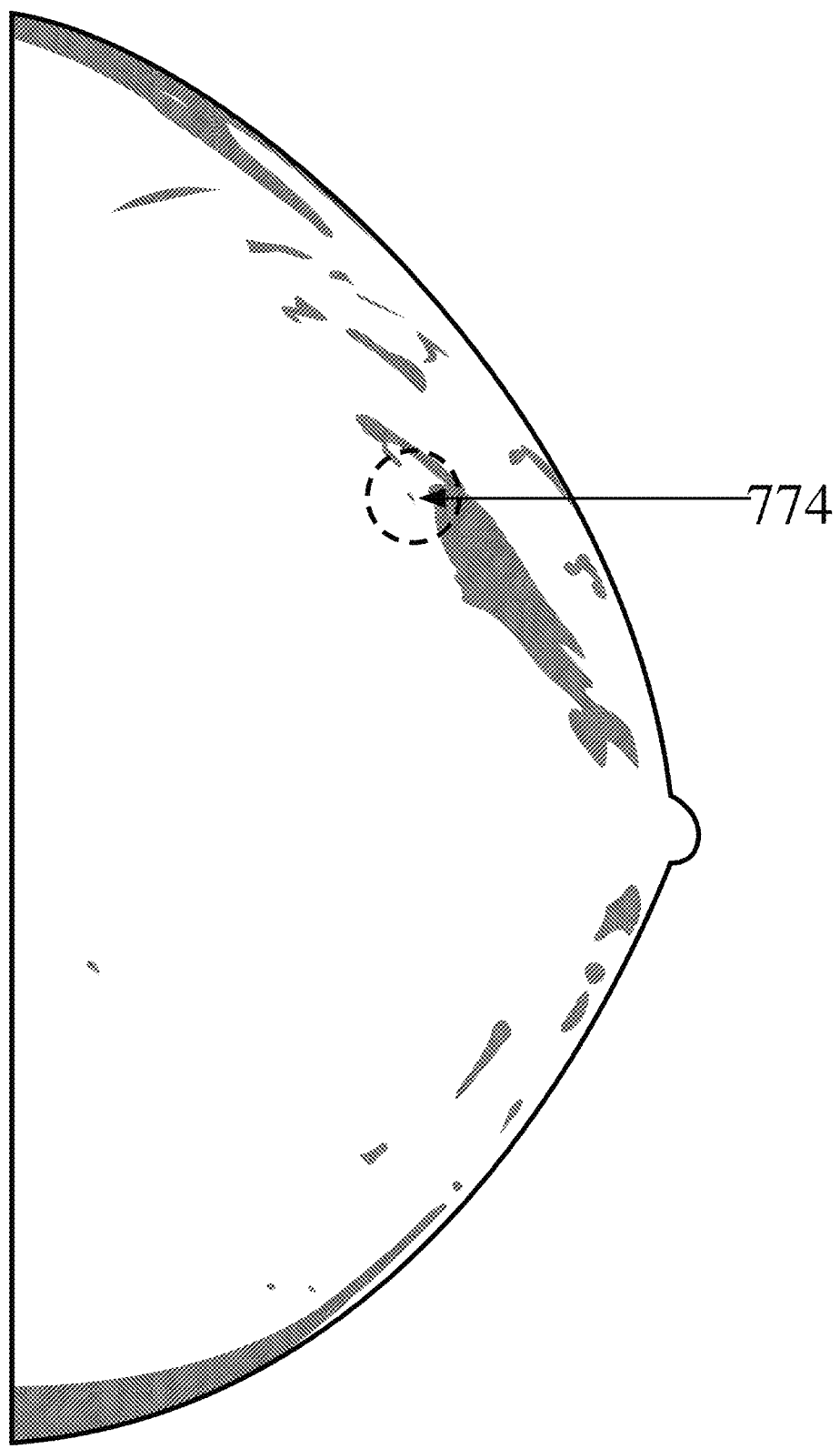
FIG. 7B shows an artists impression of an image of a human breast taken from a different angle to that shown in FIG. 7A, where the micro calcification is visible and not occluded by the denser breast tissue, according to an embodiment of the invention.

Instead, when looking at the projection image $P(\underline{v},.)$, an area of increased density, such as a lesion or calcification will appear as a brighter spot, irrespective of its z-position, making it possible to detect in many cases. FIG. 7A shows an artists impression of an image of a human breast computed from a number of 2D X-Ray images produced by a DBT device taken from a specific angle where a micro calcification is occluded by denser breast tissue. In FIG. 7A a region 774 is identified. FIG. 7B shows an artists impression of an image of a human breast taken from a different angle to that shown in FIG. 7A. Comparison of FIG. 7A and FIG. 7B show a micro calcification is visible in FIG. 7B when the tissue is not occluded by denser breast tissue. Unexpectedly, in FIG. 7B the region 774 which was identified in FIG. 7A shows a micro calcification is visible and not occluded by the denser breast tissue.

Figure 8A:
FIG. 8A shows an artists impression of a screen dump of a video image at approximately the two (2) second time point, where the video shows a dynamic comparison of a human breast computed from a number of images recreated as the viewing direction is changed, where micro calcification occluded by denser breast tissue can be revealed, according to an embodiment of the invention.
Figure 8B:
FIG. 8B shows an artists impression of a screen dump of a video image at approximately the five (5) second time point, where the video shows a dynamic comparison of a human breast computed from a number of images recreated as the viewing direction is changed, where micro calcification occluded by denser breast tissue can be revealed, according to an embodiment of the invention.
Figure 8C:
FIG. 8C shows an artists impression of a screen dump of a video image at approximately the nine (9) second time point, where the video shows a dynamic comparison of a human breast computed from a number of images recreated as the viewing direction is changed, where micro calcification occluded by denser breast tissue can be revealed, according to an embodiment of the invention.
Figure 8D:
FIG. 8D shows an artists impression of a screen dump of a video image at approximately the twelve (12) second time point, where the video shows a dynamic comparison of a human breast computed from a number of images recreated as the viewing direction is changed, where micro calcification occluded by denser breast tissue can be revealed, according to an embodiment of the invention.
Figure 9A:
FIG. 9A shows the artists impression of a screen dump of a video image at approximately the five (5) second time point shown in FIG. 8B, according to an embodiment of the invention.
Figure 9B:
FIG. 9B shows the artists impression of a screen dump of a video image at approximately nine (9) second time point shown in FIG. 8C, according to an embodiment of the invention.

FIGS. 8A-8D show an artists impression of four (4) images which make up time points in a mp3 video of a dynamic comparison of DBT of a right breast while the viewing direction changes, according to an embodiment of the invention. The mp3 video used to generate FIGS. 8A-8D had a duration of approximately 13 seconds. Unexpectedly, the mp3 video is an excellent means of inspecting DBTs to identify micro calcifications. FIG. 8A shows the artists impression of a screen dump from the mp3 video at approximately the two (2) second time point. FIG. 8B shows the artists impression of a screen dump from the mp3 video at approximately the five (5) second time point. FIG. 8C shows the artists impression of a screen dump from the mp3 video at approximately the nine (9) second time point. FIG. 8D shows the artists impression of a screen dump from the mp3 video at approximately the twelve (12) second time point. The dynamic comparison illustrates the differences between the intensity of the voxel matrix from which the projection image is calculated. Unexpectedly, when viewing the video a spot becomes apparent, which is shown in FIG. 8B and FIG. 8C but is not present in FIG. 8A or FIG. 8D. FIG. 9A shows an enlarged version of FIG. 8B, the artists impression of the screen dump from the mp3 video at approximately the five (5) second time point where the region 774 is identified. FIG. 9B shows an enlarged version of FIG. 8C, the artists impression of the screen dump from the mp3 video at approximately the nine (9) second time point where the region 774 is again identified. The spot seen in FIG. 8B (FIG. 9A) and FIG. 8C (FIG. 9B) reduces in intensity between the observation in FIG. 8B (FIG. 9A) and the observation in FIG. 8C (FIG. 9B). Unexpectedly, the emergence and dimunition of a relatively bright spot in the same position when viewing a video, can also be used to confirm a microcalcification rather than an artifact of the imaging system. Thus, based on the mp3 video a microcalcification 774 jumps to the viewer's attention by way of the nature of the dynamic comparison, as shown in the difference between FIG. 8A where no microcalcification is present and FIG. 8B (FIG. 9A) where the microcalcification, 774 is present. Viewing the mp3 video improves the visual clarity of identification of a micro calcification.

Figure 13A:
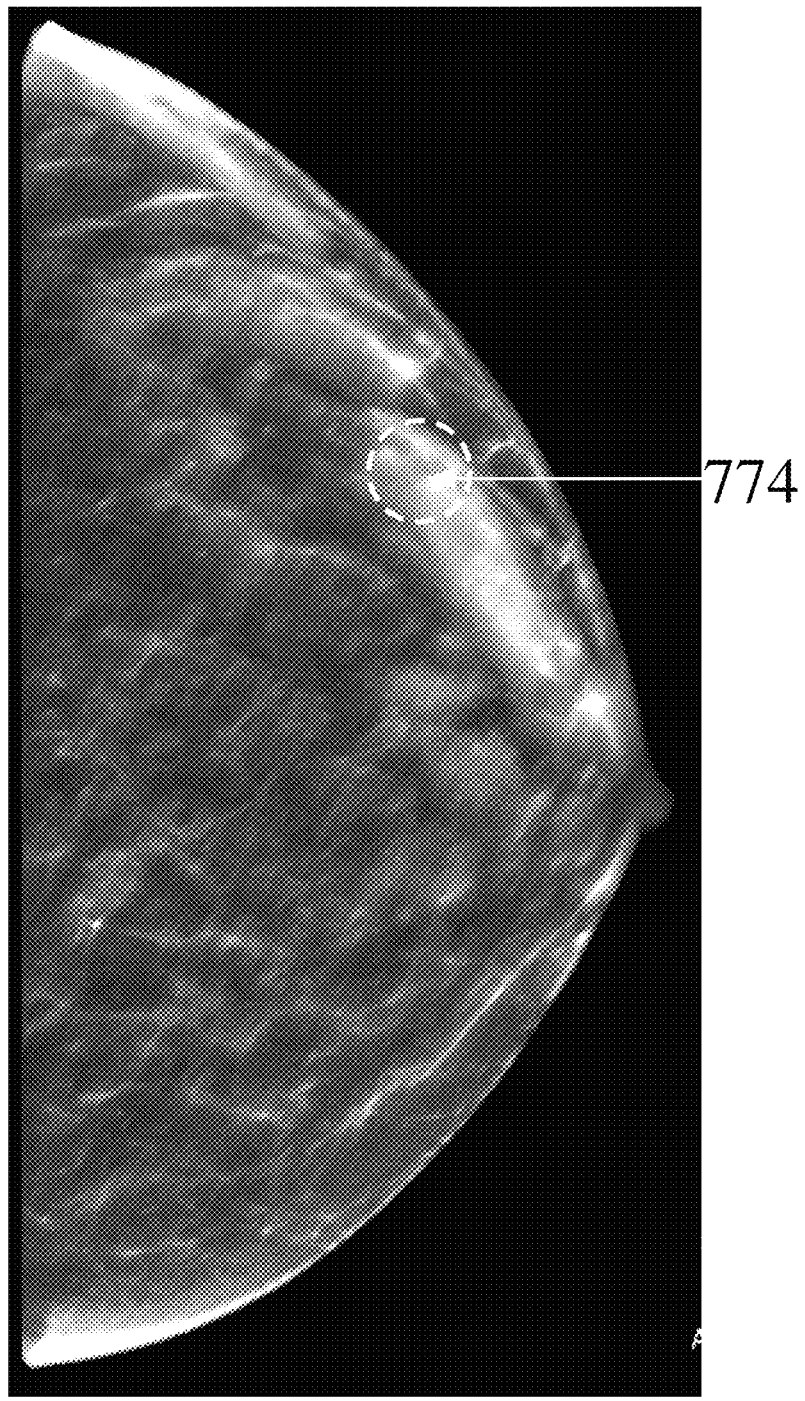
FIG. 13A shows the image of a human breast represented in FIG. 7A, according to an embodiment of the invention.
Figure 13B:
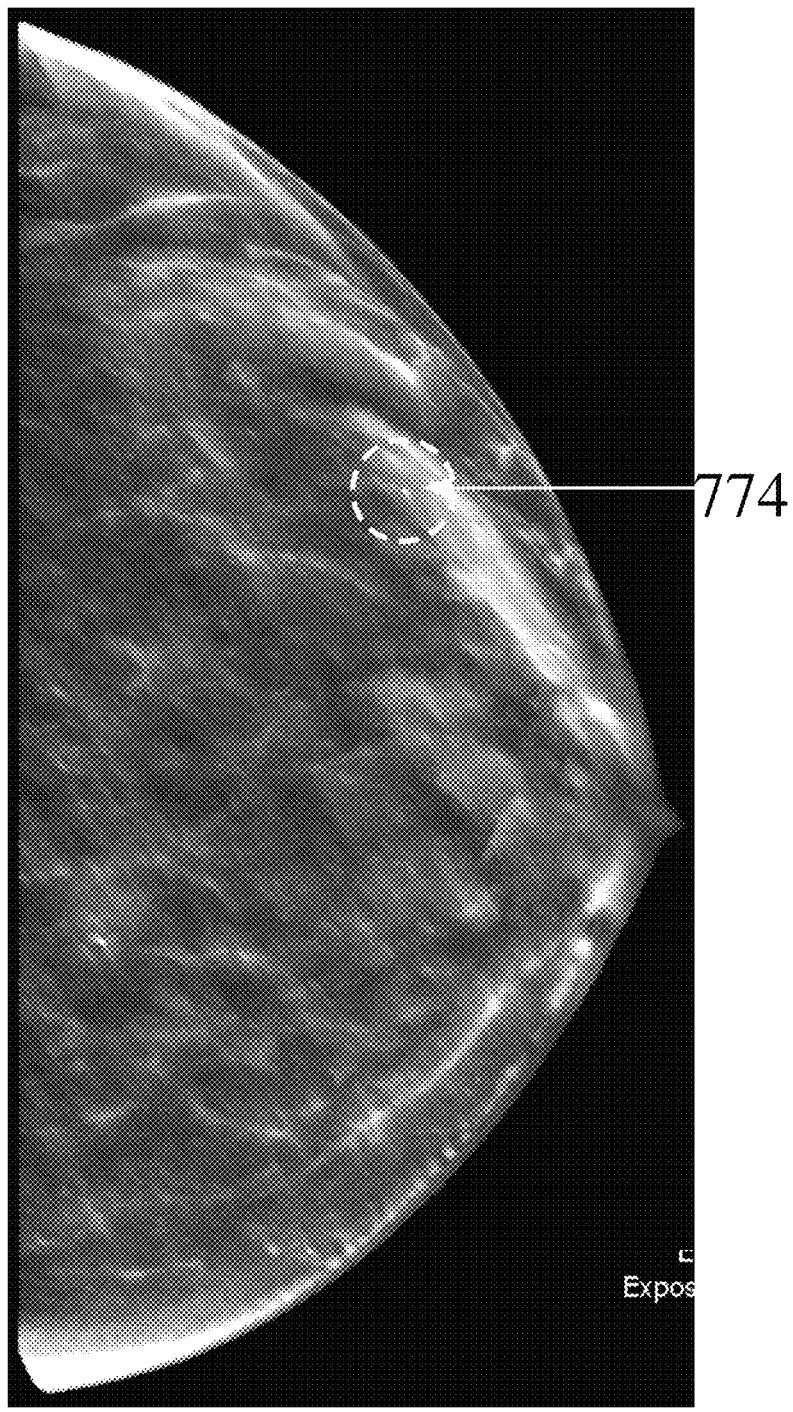
FIG. 13B shows the image of the human breast taken from a different angle to that shown in FIG. 13A, represented in FIG. 7B, according to an embodiment of the invention.
Figure 14A:
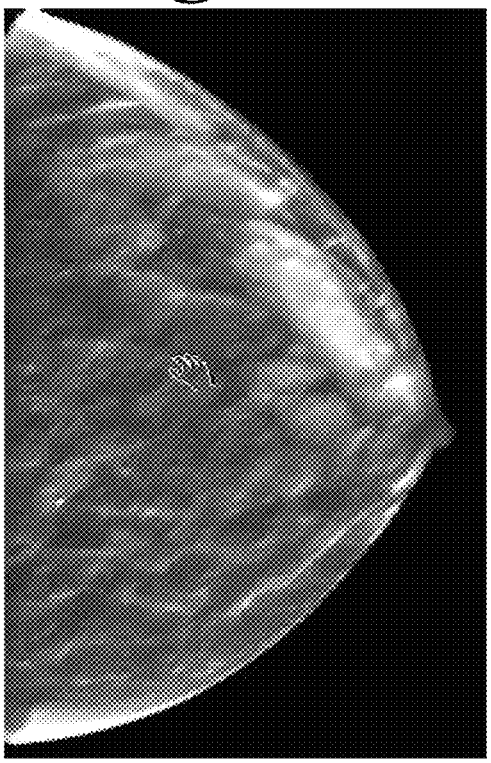
FIG. 14A shows a screen dump from the mp3 video at approximately the two (2) second time point, represented in FIG. 8A, according to an embodiment of the invention.
Figure 14B:
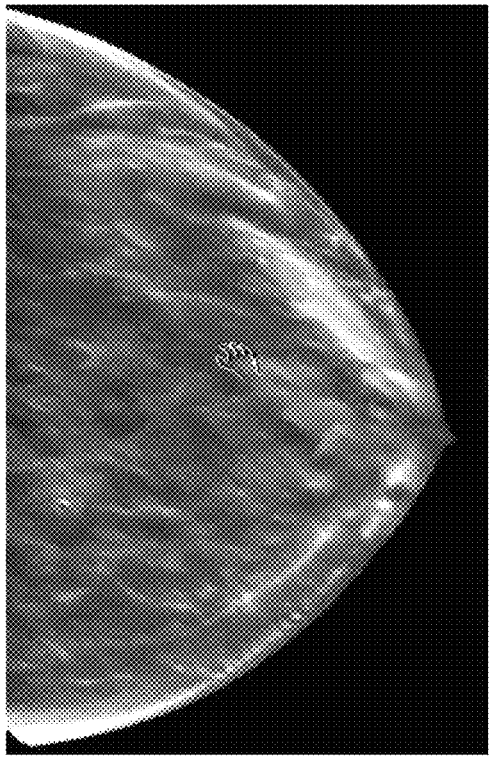
FIG. 14B shows a screen dump from the mp3 video at approximately the five (5) second time point, represented in FIG. 8B, according to an embodiment of the invention.
Figure 14C:
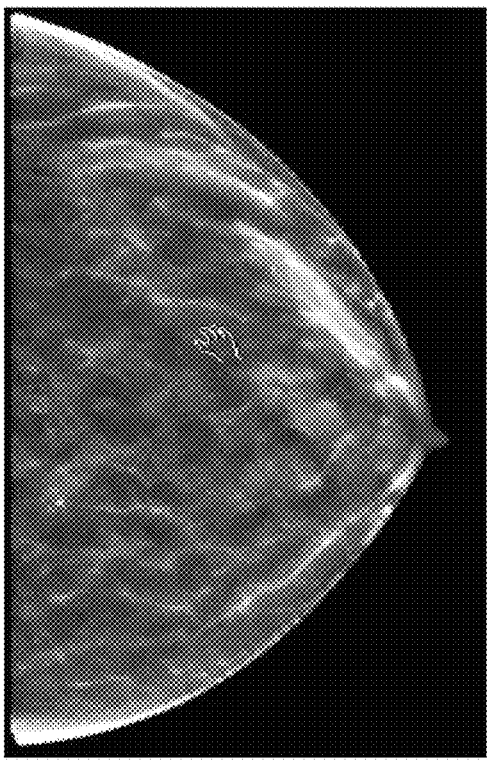
FIG. 14C shows a screen dump from the mp3 video at approximately the nine (9) second time point, represented in FIG. 8C, according to an embodiment of the invention.
Figure 14D:
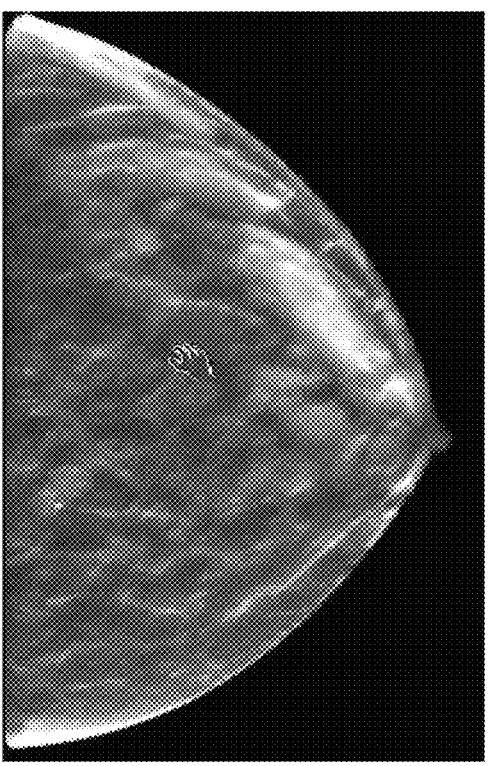
FIG. 14D shows a screen dump from the mp3 video at approximately the twelve (12) second time point, represented in FIG. 8D, according to an embodiment of the invention.
Figure 15A:
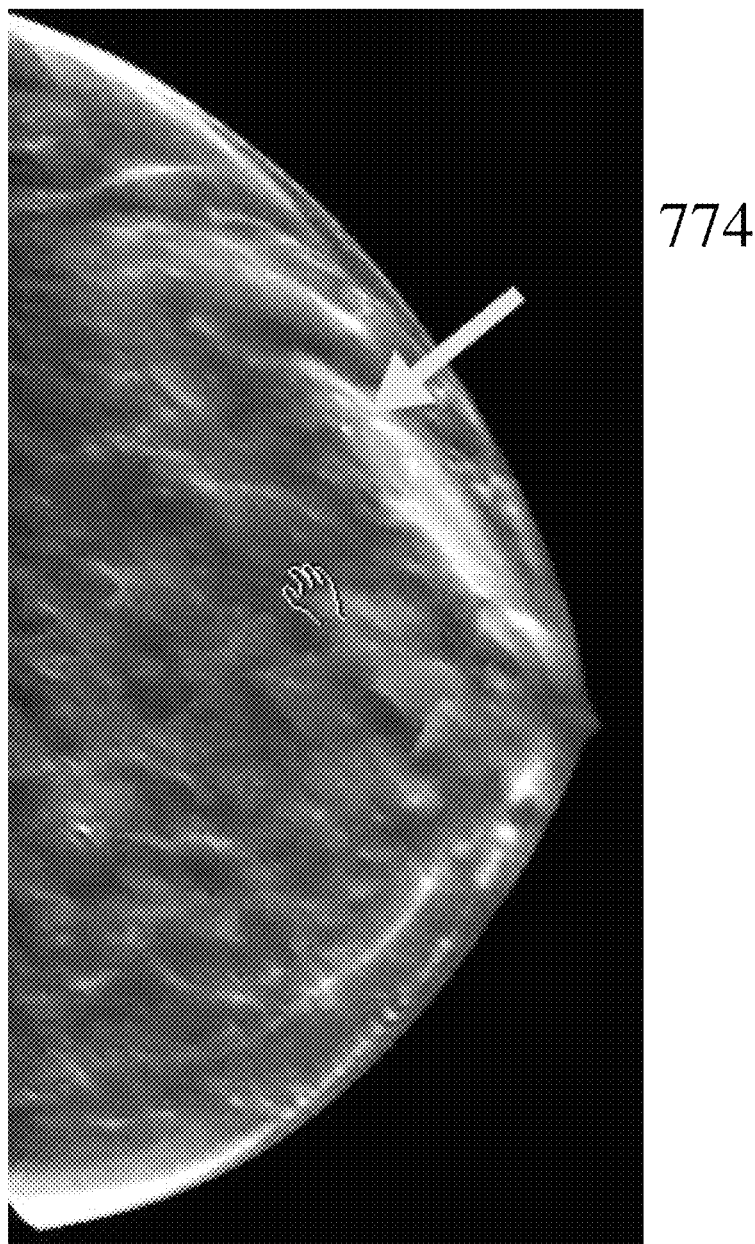
FIG. 15A shows the screen dump from the mp3 video at approximately the five (5) second time point, as represented in FIG. 9A, according to an embodiment of the invention.
Figure 15B:
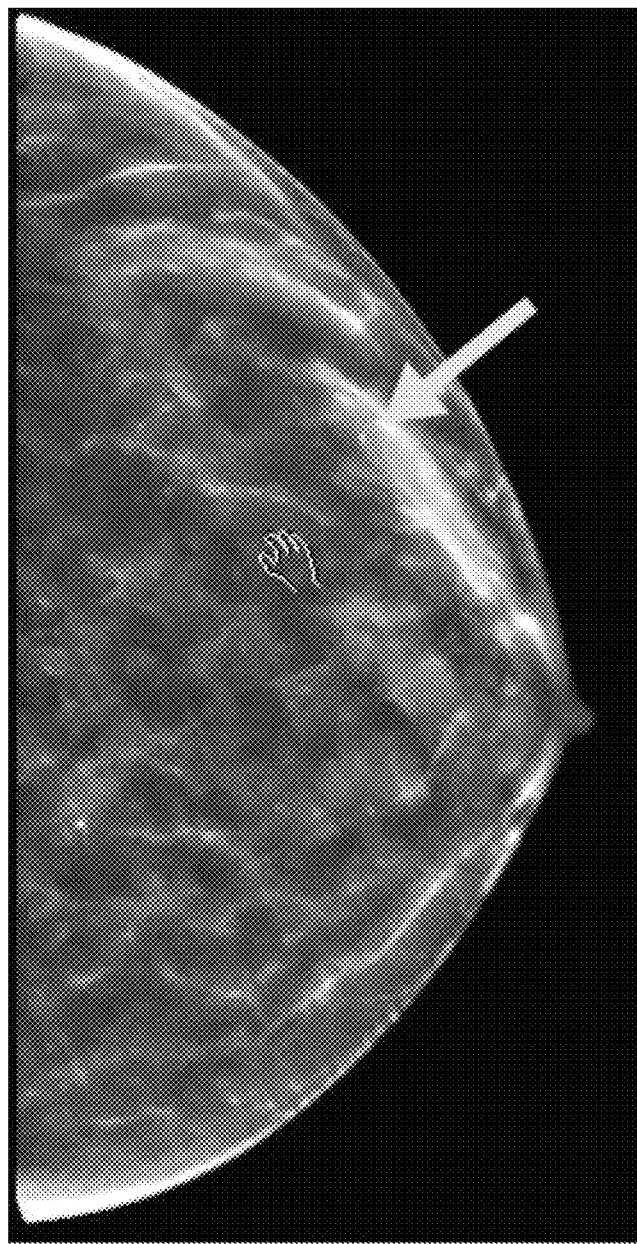
FIG. 15B shows the screen dump from the mp3 video at approximately the nine (9) second time point, as represented in FIG. 9B, according to an embodiment of the invention

FIG. 13A shows the image of a human breast generated from a volumetric image reconstructed from a number of 2D X-Ray images produced by a DBT device, where the generated 2-D projection image was formed at a specific angle, where a micro calcification is occluded by denser breast tissue, as represented in FIG. 7A. FIG. 13B shows the generated 2-D projection image of the human breast formed from a different angle to that shown in FIG. 13A, where the micro calcification is visible and not occluded by the denser breast tissue, as represented in FIG. 7B. FIGS. 14A-14D show four (4) images which make up time points in the mp3 video of the dynamic comparison of the DBT of the right breast. FIG. 14A shows a screen dump from the mp3 video at a two (2) second time point, as represented in FIG. 8A. FIG. 14B shows a screen dump from the mp3 video at the five (5) second time point, as represented in FIG. 8B. FIG. 14C shows a screen dump from the mp3 video at the nine (9) second time point, as represented in FIG. 8C. FIG. 14D shows a screen dump from the mp3 video at the twelve (12) second time point, as represented in FIG. 8D. FIG. 15A shows an enlarged version of FIG. 14B, the screen dump from the mp3 video at the five (5) second time point where the region 774 is identified, as represented in FIG. 9A. FIG. 15B shows an enlarged version of FIG. 14C, the screen dump from the mp3 video at the nine (9) second time point where the region 774 is identified, as represented in FIG. 9B.

Figure 3A:
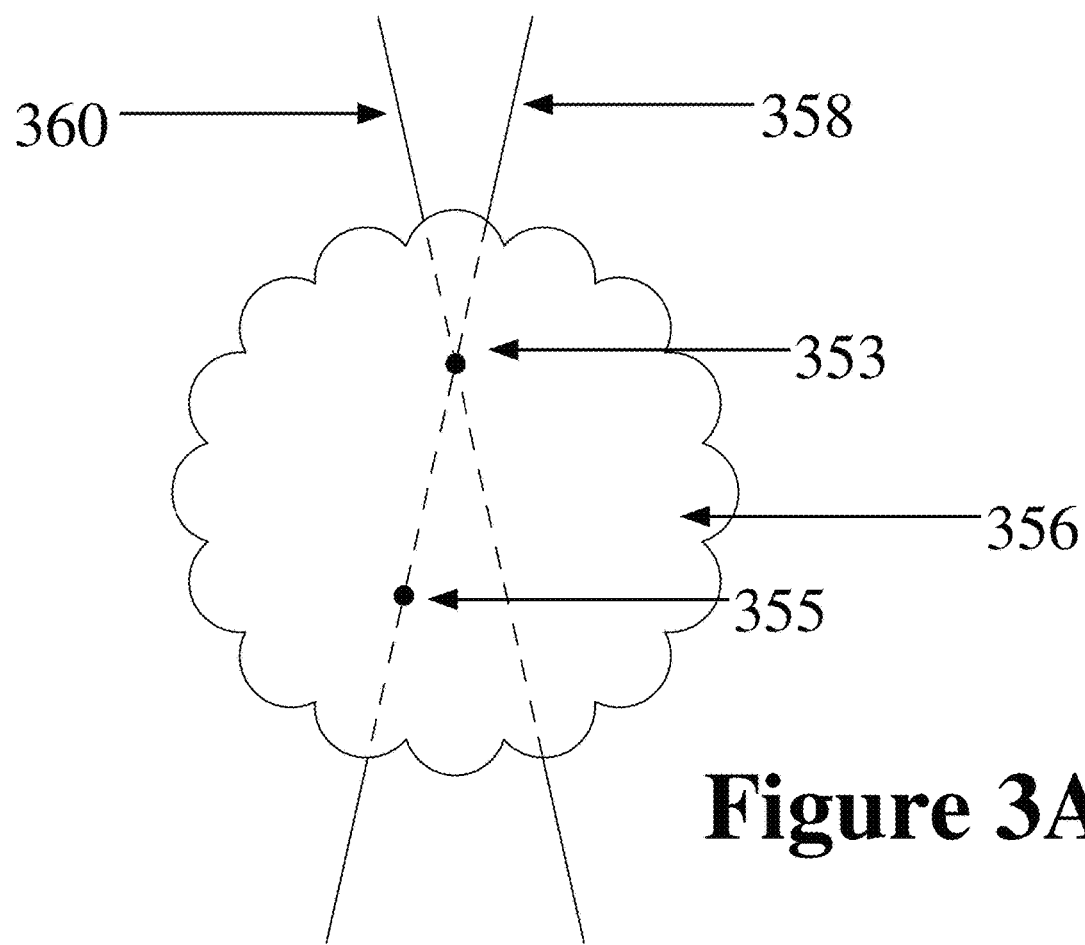
FIG. 3A shows a specimen with two areas of increased density, according to an embodiment of the invention.
Figure 3B:
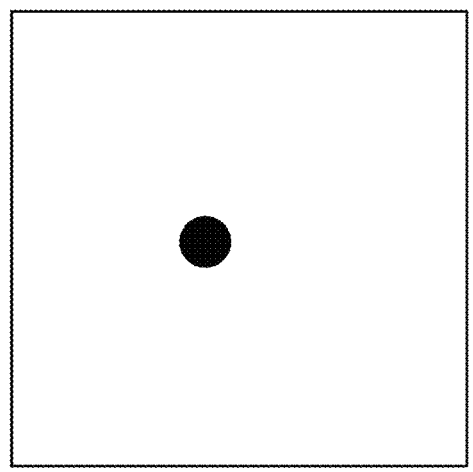
FIG. 3B shows the two areas in FIG. 3A projected to the same spot in the projection Image, according to an embodiment of the invention.

A draw-back of any projection method, is that there can be an occlusion or overlay effect. In the case of a maximum intensity projection as defined above, consider the case where two (2) separate areas of increased density are at different z positions on approximately the same viewing ray $\underline{v}$. FIG. 3A shows a specimen 356 with two separate areas 353 and 355 of increased density. In the projection they will appear as one, potentially larger spot. That is, for one viewing direction (v1) 358 the two separate areas 353 and 355 can be projected to the same spot in the projection image (projection 1) shown in FIG. 3B.

Figure 3C:
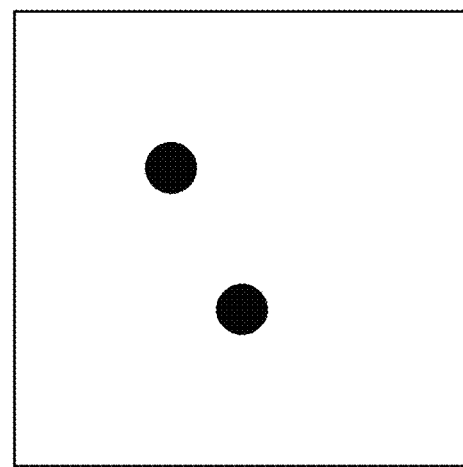
FIG. 3C shows the two areas in FIG. 3A projected to different spots in the projection Image, according to an embodiment of the invention.

In an embodiment of the present invention, this ambiguity can be resolved by making the projection dynamic. Instead of choosing a fixed viewing direction v, a dynamic viewing direction can be used. Using an alternative viewing direction (v2) 360, the two separate areas 353 and 355 project to different spots in the projection image, making it obvious that there are two areas of interest. FIG. 3C shows for the second viewing direction (v2) 360 the two separate areas 353 and 355 can be projected to different spots in the generated 2-D projection image (projection 2).

In an alternative embodiment of the invention, different dynamic functions can be used to generate dynamic projection viewing directions. Given the non-isotropy of the input data mentioned above, the most useful dynamic functions are continuous periodic functions around the z direction. Two non-limiting examples of dynamic functions include:

$$v(t) = \text{normalize}(\underline{z} + A \sin(\omega t)\underline{x}) \qquad \text{Equation 1}$$

$$v(t) = \text{normalize}(\underline{z} + A \sin(\omega t)\underline{x} + A \cos(\omega t)\underline{y}) \qquad \text{Equation 2}$$

where normalize($\underline{v}$)=$\underline{v}$/|v|; t: time; $\omega = 2\pi f$; f: frequency of the dynamic movement and A: Amplitude of the dynamic movement, e.g. A=0.05.

Figure 6:
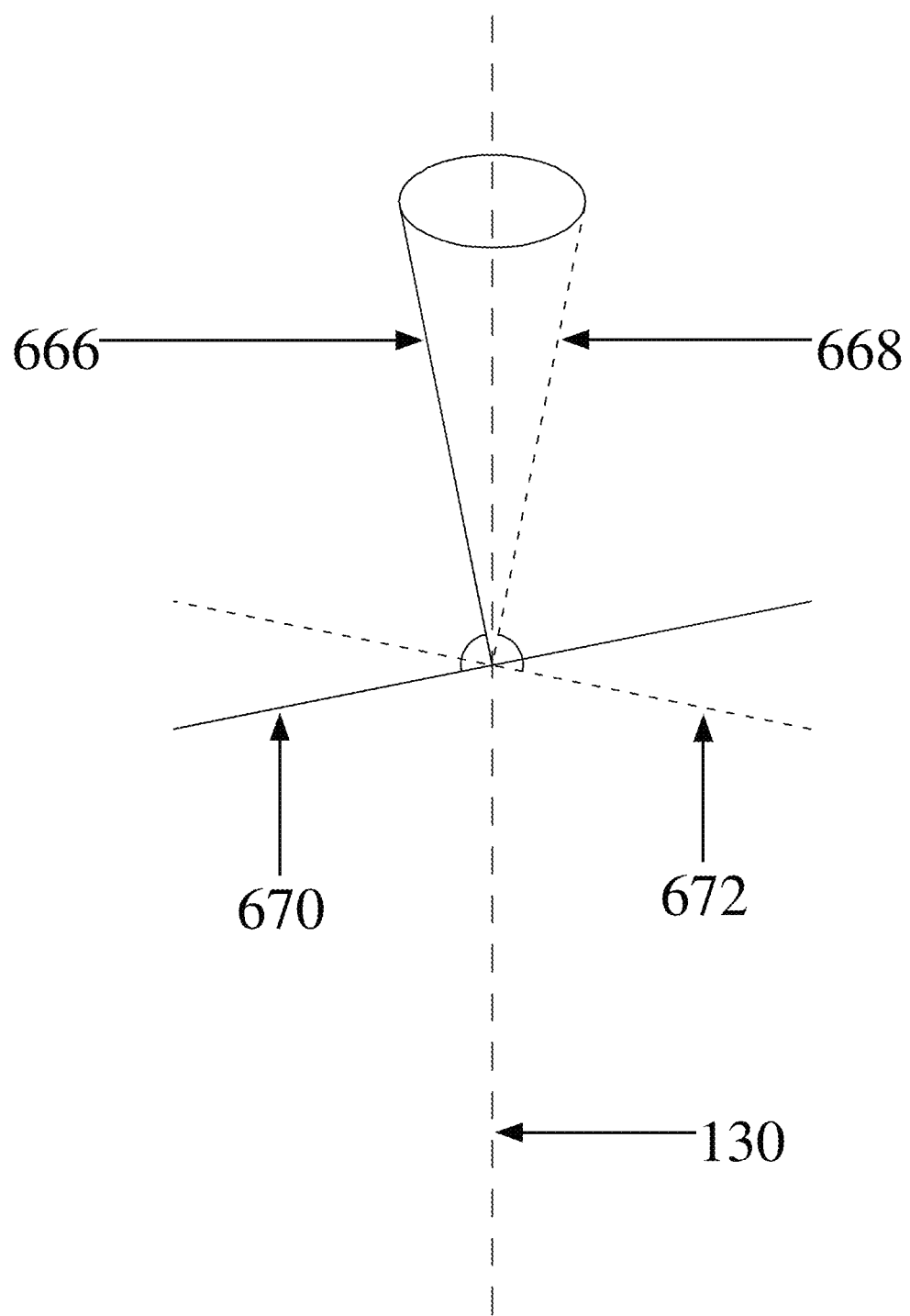
FIG. 6 illustrates the dynamic variation of the viewing direction v according to Equation 2, according to an embodiment of the invention.

In other embodiments of the invention, different alternative dynamic functions can be used to generate dynamic projection viewing directions. In an embodiment of the invention, a linear function can be used in which the angle can be changed linearly. In an alternative embodiment of the invention, a z direction can be chosen and either the x or the y direction can be incremented. FIG. 6 illustrates the dynamic variation of the viewing direction v according to Equation 2. The viewing direction at two different points $\underline{v}_{t1}$ 666 and $\underline{v}_{t2}$ 668 at time $t_1$ and $t_2$ is shown, as well as the corresponding projection planes projection plane ($t_1$) 670 and projection plane ($t_2$) 672. Over time the viewing direction $\underline{v}$ can be varied around the main acquisition direction $\underline{z}$ 130.

In another embodiment of the invention, the viewing direction can be determined by the user. In another alternative embodiment of the invention, the viewing direction can be determined by the user with an appropriate input device, such as a mouse. In an embodiment of the present invention, let ($m_{x1}$, $m_{y1}$) be the position of the mouse (or appropriate input device) at a starting time $t_1$. The starting time can then be defined by a mouse click (or appropriate input device). In an alternative embodiment of the present invention, the starting time can be triggered by the user entering a certain window with the mouse (or appropriate input device), or other graphical or non graphical criteria.

Assuming the user is moving the mouse, let ($m_{x2}$, $m_{y2}$) be the position of the mouse (or appropriate input device) at time $t_2$. Let $s_{width}$ and $s_{height}$ be the width and height of the screen.

Then v(t2)=normalize ($\underline{z}+2A\underline{x}$ ($m_{x2}-m_{x1}$)/$s_{width}$+2A $\underline{y}$ ($m_{y2}-m_{y1}$)/$s_{height}$) can be the interactively controlled viewing direction at time $t_2$. A person of ordinary skill in the art will appreciate that alternative mappings from the mouse coordinates to viewing directions can be used. In various embodiments of the present invention, alternative input methods or devices can be used including, a slider, a trackball, a head tracking device or an eye tracking device.

The above projection is a maximum intensity projection. In various other embodiments of the present invention, other projection functions can be used, including emission absorption models or minimum intensity projections. The above projection is equivalent to an orthographic projection, where a 3-D object is represented in two dimensions through parallel projection, where all the projection lines are orthogonal to the projection plane. A person of ordinary skill in the art will appreciate that alternative projections including perspective projections can be used.

In an embodiment of the invention, an optimal viewing direction can be selected by comparing the resulting projection images at a plurality of viewing directions. In an embodiment of the invention, the criterion used for determining the optimal viewing direction can be a viewing direction that identifies an unobserved obstruction. In an alternative embodiment of the invention, the criterion used for determining the optimal viewing direction can be a viewing direction that improves the visual clarity of an initial projection image. In another alternative embodiment of the invention, the criterion used for determining the optimal viewing direction can be a viewing direction that improves the visual clarity of an improved projection image compared with an initial projected image. In a different embodiment of the invention, the criterion used for determining the optimal viewing direction can be a viewing direction that improves the visual clarity of identification of an obstruction. In another different embodiment of the invention, the criterion used for determining the optimal viewing direction can be a viewing direction that identifies an obstruction using direct comparison. In another embodiment of the invention, the criterion used for determining the optimal viewing direction can be a viewing direction that improves the direct comparison clarity of an initial projection image. In an embodiment of the invention, the criterion used for determining the optimal viewing direction can be a viewing direction that improves the direct comparison clarity of an improved projection image compared with an initial projected image. In another embodiment of the invention, the criterion used for determining the optimal viewing direction can be a viewing direction that improves the direct comparison clarity of identification of an obstruction.

Figure 4:
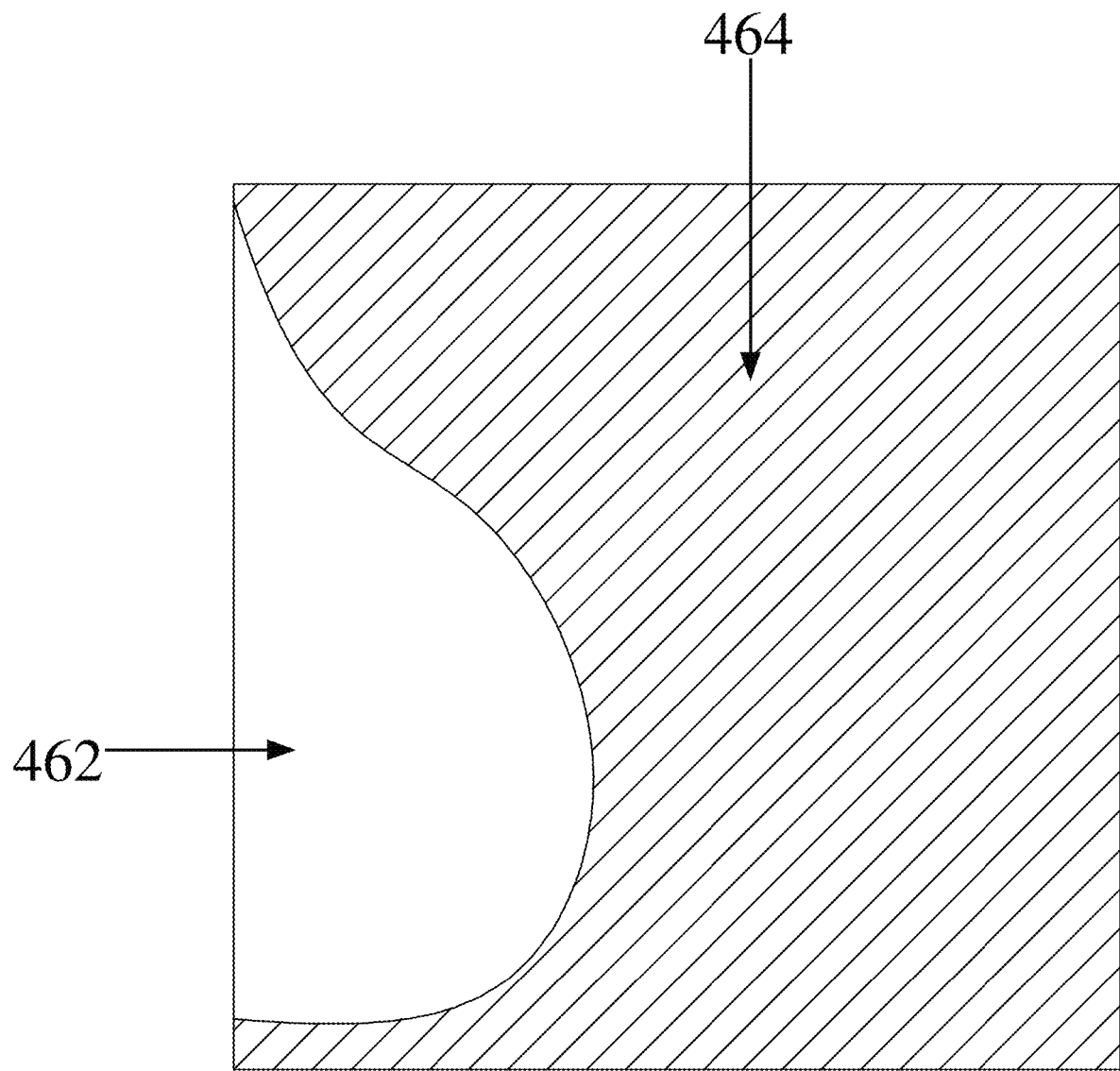
FIG. 4 shows how only a subset of the acquisition volume is covered by the specimen, while other areas (hatched) only contain background pixels, according to an embodiment of the invention.
Figure 5:
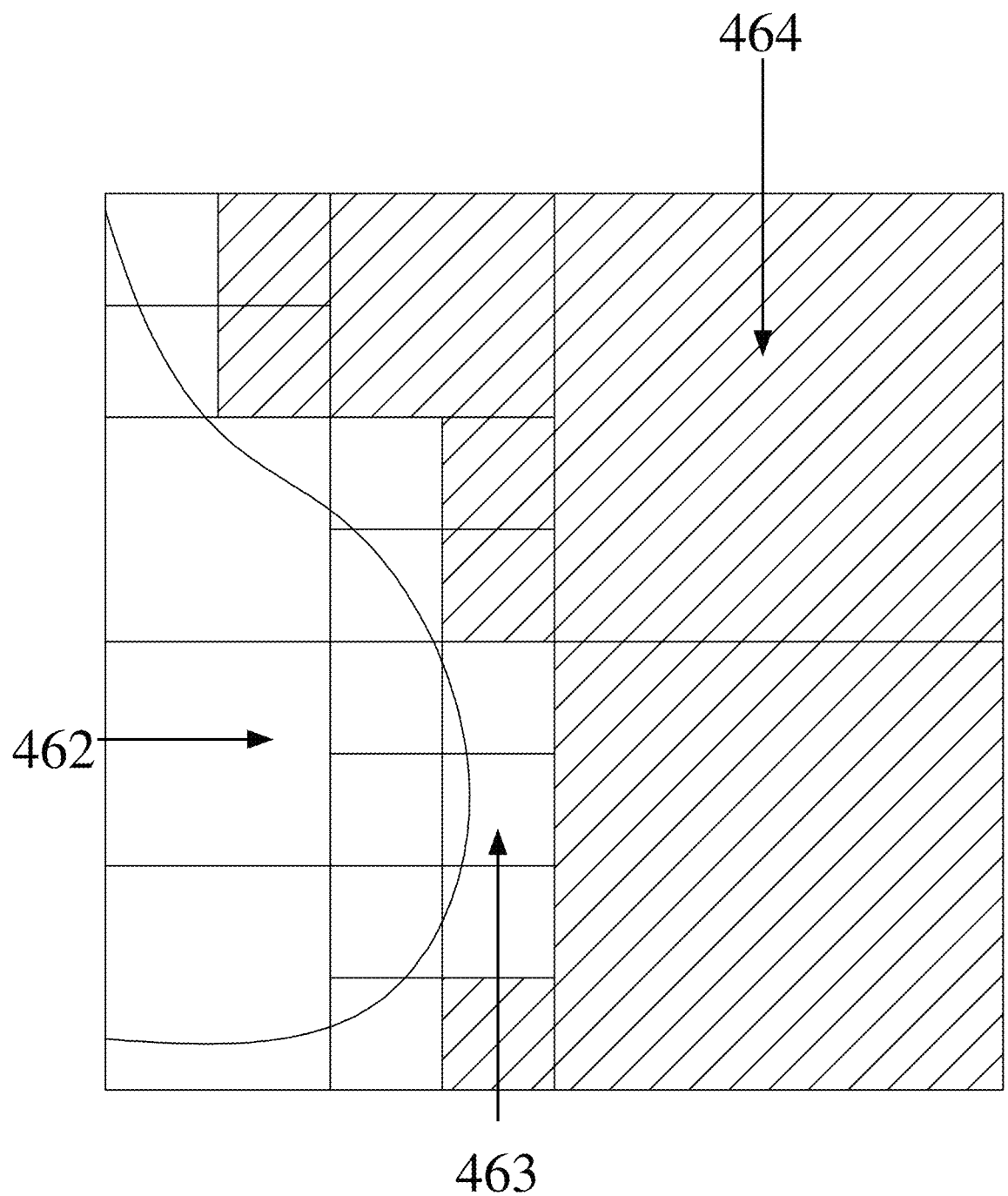
FIG. 5 shows the volume subdivided into sub-volumes, according to an embodiment of the invention.

Volumetric images in DBT are quite large data sets, as the xy-resolution is an order of magnitude larger than for example a standard CT scan. In order to render such large images at interactive speeds graphics processing units (GPU) can be utilized, see for example, U.S. Pat. No. 8,189,002, 'Methods and Apparatus for Visualizing Three-Dimensional and Higher-Dimensional Image Data Sets' May 29, 2012 and which is herein expressly incorporated by reference in its entirety. In typical DBT images, only a subset of the voxels of the volumetric image contain tissue, while other voxels are background pixels that are irrelevant for the diagnosis. In an embodiment of the present invention, by using a threshold segmentation these background pixels can be identified. FIG. 4 shows how only a subset of the acquisition volume is covered by the specimen 462, while other areas (hatched) 464 only contain background pixels. These background pixels can be identified using threshold segmentation. FIG. 5 shows the volume can be subdivided into sub-volumes. In one embodiment of the invention, an octree decomposition scheme can be used for this subdivision. In another embodiment of the invention, a binary space partitioning (BSP) scheme can be used for the subdivision. A person with ordinary skills in the art will appreciate that other subdivision schemes can be used. Sub-volumes that contain only background voxels (shown as hatched in FIG. 4 and FIG. 5) 464 can be skipped during the rendering process. Sub-volumes 463 that contain both, background voxels and tissue voxels can be further sub-divided until a configured minimum size containing specimen 462 or background 464 can be reached. In an embodiment of the invention, bricking can be used to display only those sub-volumes that are not background-only. The technique of bricking for GPU based rendering is described in U.S. Pat. No. 8,189,002.

In an embodiment of the present invention, for the effective use of dynamic projection images, a sufficiently high frame rate is required in order to allow for a smooth rendering that appears natural to the user. This can be achieved in many cases by using GPU hardware combined with the bricking technique.

In an alternative embodiment of the present invention, a periodic dynamic viewing direction function can be used, and a sequence of projections covering one full period (1/f) can be pre-rendered, and then be played back in a loop. In case of a client server visualization system, the pre-rendered images can be computed on the server side and cached on the client side thereby making optimal use of the bandwidth and allowing for smooth playback even on slow networks.

In radiological diagnostics, comparison to prior images is relevant to detect change, e.g. tumor growth. In an embodiment of the present invention, a projection of a current image and a projection of the corresponding prior image can be displayed side-by-side and used to determine the change in tumor characteristics. The comparison can include the user visually comparing with the naked eye. The comparison can also be undertaken by a direct comparison program where equivalent viewing directions are used for the direct comparison. In various embodiments of the present invention, the user can choose the same dynamic viewing direction function for both, the current and the prior image, thereby allowing for direct comparison.

Another aspect of the invention is to combine the projection display of the volumetric image with conventional 2D mammograms or other X-Ray or radiological images, by dividing the available computer screens into virtual view ports and using one or more of the virtual view ports to display the one or more projection images, and one or more of the virtual viewports to display the other radiological images.

A method for displaying one or more optimal projection images generated from a volumetric image comprising the steps of receiving the volumetric image, computing a plurality of projection images of the volumetric image using a plurality of viewing directions, where at least an initial projection image of the plurality of projection images is computed using a first viewing direction, where a second viewing direction of the plurality of viewing directions is not equal to the first viewing direction, one or more of time comparing, structurally comparing and dynamically comparing the plurality of projection images to determine one or more optimal projection images and displaying the optimal projection images.

A method for identifying one or more optimal projection images generated from a volumetric image comprising the steps of receiving the volumetric image, computing a plurality of projection images of the volumetric image using a plurality of viewing directions, where at least an initial projection image of the plurality of projection images is computed using a first viewing direction, where a second viewing direction of the plurality of viewing directions is not equal to the first viewing direction, and one or more of time comparing, structurally comparing and dynamically comparing the plurality of projection images to determine one or more optimal projection images.

A method for identifying one or more optimal projection images generated from a volumetric image comprising the steps of receiving the volumetric image, computing a plurality of projection images of the volumetric image using a plurality of viewing directions, where at least an initial projection image of the plurality of projection images is computed using a first viewing direction, where a second viewing direction of the plurality of viewing directions is not equal to the first viewing direction, and one or more of time comparing, structurally comparing and dynamically comparing the plurality of projection images to determine one or more optimal projection images, where the optimal viewing direction is selected from the group consisting of a viewing direction that identifies an unobserved obstruction, a viewing direction that improves the visual clarity of the first projection image, a viewing direction that improves the visual clarity of the second projection image, a viewing direction that improves the visual clarity of identification of an obstruction, a viewing direction that identifies an obstruction using direct comparison, a viewing direction that increases the differentiated intensity values of the first projection image, a viewing direction that increases the differentiated intensity values of the second projection image, a viewing direction that improves the direct comparison clarity of the first projection image, a viewing direction that improves the direct comparison clarity of the second projection image, and a viewing direction that improves the direct comparison clarity of identification of an obstruction.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where the optimal viewing direction is selected from the group consisting of a viewing direction that identifies an unobserved obstruction, a viewing direction that improves the visual clarity of the first projection image, a viewing direction that improves the visual clarity of the second projection image, a viewing direction that improves the visual clarity of identification of an obstruction, a viewing direction that identifies an obstruction using direct comparison, a viewing direction that improves the direct comparison clarity of the first projection image, a viewing direction that improves the direct comparison clarity of the second projection image, and a viewing direction that improves the direct comparison clarity of identification of an obstruction.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where the volumetric image is a 3D image.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where the plurality of projection images are 2D images.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where at least one of the plurality of viewing directions is determined using a periodic continuous mathematical function.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where at least one of the plurality of viewing directions is determined using a periodic continuous mathematical function, where the plurality of projection images is a sequence of projections images spanning one period of the periodic continuous mathematical function.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where at least one of the plurality of viewing directions is determined using a periodic continuous mathematical function, where the plurality of projection images is a sequence of projections images spanning one period of the periodic continuous mathematical function, further comprising rendering and caching a sequence of projection images.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where at least one of the plurality of viewing directions is determined using a periodic continuous mathematical function, where the plurality of projection images is a sequence of projections images spanning one period of the periodic continuous mathematical function, further comprising rendering and caching a sequence of projection images, where the rendered and cached sequence of projections are played back one or more times.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where at least one of the plurality of viewing directions is determined using a periodic continuous mathematical function, where the plurality of projection images is a sequence of projections images spanning one period of the periodic continuous mathematical function, further comprising rendering and caching a sequence of projection images, where the rendering is carried out on a server and one or both the caching and play back is carried out on a client computer.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where a graphics processing unit is used to compute one or more of the plurality of projection images.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where a graphics processing unit is used to compute one or more of the plurality of projection images, where bricking is used to accelerate computation of one or more of the plurality of projection images.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, where one or more of the plurality of viewing directions is based on user input.

A method to determine one or more optimal projection images from a volumetric image comprising the steps of receiving a volumetric image, computing a plurality of projection images based on the volumetric image using a plurality of viewing directions, one or more of time comparing, structurally comparing and dynamically comparing the plurality of projection images to determine one or more optimal viewing directions, and correlating the optimal viewing directions with one or more projection images of the plurality of projection images to determine one or more optimal projection images, further comprising visually comparing the plurality of projection images.

A system that displays a first projection image and a second projection image of a volumetric image comprising computing a first projection image of the volumetric image using a first viewing direction, computing a second projection image of the volumetric image using a second viewing direction, where the first viewing direction is not equal to the second viewing direction, and displaying the first projection image and the second projection image.

A system that displays a first projection image and a second projection image of a volumetric image comprising computing a first projection image of the volumetric image using a first viewing direction, computing a second projection image of the volumetric image using a second viewing direction, where the first viewing direction is not equal to the second viewing direction, and displaying the first projection image and the second projection image, further comprising computing a third projection image using a third viewing direction, and displaying one or both the first projection image and the second projection image with the third projection image.

A system that displays a first projection image and a second projection image of a volumetric image comprising computing a first projection image of the volumetric image using a first viewing direction, computing a second projection image of the volumetric image using a second viewing direction, where the first viewing direction is not equal to the second viewing direction, and displaying the first projection image and the second projection image, further comprising computing a third projection image using a third viewing direction, and displaying one or both the first projection image and the second projection image with the third projection image, where one or both the second viewing direction and the third viewing direction are determined using a periodic continuous mathematical function.

A system that compares a first projection image and a second projection image of a volumetric image comprising computing a first projection image of the volumetric image using a first viewing direction, computing a second projection image of the volumetric image using a second viewing direction, and one or more of time comparing, structurally comparing and dynamically comparing the first projection image and the second projection image.

A system that compares a first projection image and a second projection image of a volumetric image comprising computing a first projection image of the volumetric image using a first viewing direction, computing a second projection image of the volumetric image using a second viewing direction, and one or more of time comparing, structurally comparing and dynamically comparing the first projection image and the second projection image, further comprising computing a third projection image using a third viewing direction, and comparing one or both the first projection image and the second projection image with the third projection image.

A system that compares a first projection image and a second projection image of a volumetric image comprising computing a first projection image of the volumetric image using a first viewing direction, computing a second projection image of the volumetric image using a second viewing direction, and one or more of time comparing, structurally comparing and dynamically comparing the first projection image and the second projection image, further comprising computing a third projection image using a third viewing direction, and comparing one or both the first projection image and the second projection image with the third projection image, where one or both the second viewing direction and the third viewing direction are determined using a periodic continuous mathematical function.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function, further comprising rendering and caching a sequence of projection images.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function, further comprising rendering and caching a sequence of projection images, where the rendered and cached sequence of projection images are played back one or more times.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function, further comprising rendering and caching a sequence of projection images, where the rendering is carried out on a server.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function, further comprising rendering and caching a sequence of projection images, where the caching is carried out on a client computer.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where the plurality of projection images is a sequence of projection images spanning one period of the periodic continuous mathematical function, further comprising rendering and caching a sequence of projection images, where the rendering is carried out on a server, where the play back is carried out on a client computer.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where a graphics processing unit is used to compute one or more of the plurality of projection images.

A method for identifying an object in a projection image comprising the steps of receiving a three dimensional volumetric image of a tissue, computing a plurality of projection images of the three dimensional volumetric image of the tissue using a plurality of viewing directions, one or more of time comparing, structurally comparing and dynamically comparing the plurality of projection images, and identifying an object that is present in a projection image selected from the plurality of projection images that is not present in one or more of the one or more projection images selected from the plurality of projection images, where at least one of the plurality of viewing directions is determined using a periodic continuous mathematical function, where a graphics processing unit is used to compute one or more of the plurality of projection images, where bricking is used to accelerate computation of one or more of the plurality of projection images.

A method for identifying an optimal projection image comprising the steps of receiving a volumetric image, computing the plurality of projection images based on the volumetric image using a plurality of viewing directions, and comparing the plurality of projection images to determine an optimal viewing direction corresponding to an optimal projection image.

A method for identifying an optimal projection image comprising the steps of receiving a volumetric image, computing the plurality of projection images based on the volumetric image using a plurality of viewing directions, and comparing the plurality of projection images to determine an optimal viewing direction corresponding to an optimal projection image, where the optimal viewing direction is selected from the group consisting of a viewing direction that identifies an unobserved obstruction, a viewing direction that improves the visual clarity of the first projection image, a viewing direction that improves the visual clarity of the second projection image, a viewing direction that improves the visual clarity of identification of an obstruction, a viewing direction that identifies an obstruction using direct comparison, a viewing direction that improves the direct comparison clarity of the first projection image, a viewing direction that improves the direct comparison clarity of the second projection image, and a viewing direction that improves the direct comparison clarity of identification of an obstruction.

A method for displaying a plurality of projection images comprising the steps of receiving a volumetric image, computing the plurality of projection images based on the volumetric image using a plurality of viewing directions and displaying the plurality of projection images.

A method for comparing a first projection image and a second projection image comprising the steps of receiving a volumetric image, computing the first projection image based on the volumetric image using a first viewing direction, computing the second projection image based on the volumetric image using a second viewing direction, where the first viewing direction is not equal to the second viewing direction and one or more of time comparing, structurally comparing and dynamically comparing the first projection image and the second projection image.

A method for comparing a first projection image and a second projection image comprising the steps of receiving a volumetric image, computing the first projection image based on the volumetric image using a first viewing direction, computing the second projection image based on the volumetric image using a second viewing direction, where the first viewing direction is not equal to the second viewing direction and one or more of time comparing, structurally comparing and dynamically comparing the first projection image and the second projection image, further comprising one or more steps selected from the group consisting of identifying visually an obstruction, improving the visual clarity of the first projection image, improving the visual clarity of the second projection image, improving the visual clarity of identification of an obstruction, identifying an obstruction using direct comparison, improving the direct comparison clarity of the first projection image, improving the direct comparison clarity of the second projection image, and improving the direct comparison clarity of identification of an obstruction.

A method for displaying one or more unobstructed projection images comprising the steps of receiving a volumetric image, computing a plurality of projection images based on the volumetric image using a plurality of viewing directions, where at least a first projection image of the plurality of projection images is computed using a first viewing direction and at least a second projection image of the plurality of projection images is computed using a second viewing direction, where the first viewing direction is not equal to the second viewing direction, one or more of time comparing, structurally comparing and dynamically comparing the first projection image and the second projection image to determine if one or both of the first projection image and the second projection image are unobstructed, and displaying based on the comparison one or both the first projection image and the second projection image.

A method for displaying an unobstructed projection image of a breast comprising the steps of receiving a volumetric image of the breast, computing a first projection image of the breast based on the volumetric image using a first viewing direction and a second projection image of the breast based on the volumetric image using a second viewing direction, where the first viewing direction is not equal to the second viewing direction, one or more of time comparing, structurally comparing and dynamically comparing the second projection image of the breast with the first projection image of the breast to determine if one or both the first projection image of the breast and second projection image of the breast is unobstructed, and based on the comparison displaying one or both the first projection image of the breast and second projection image of the breast.

A system for displaying unobstructed breast projection images comprising receiving a plurality of volumetric images of a breast, where a first volumetric image of the plurality of projection images is measured at a first time and a second volumetric image of the plurality of projection images is measured at a second time, where the first time differs from the second time by a time interval, computing a first projection image from the first volumetric image measured at the first time using a first viewing direction, computing one or more projection images from the first volumetric image measured at the first time using one or more viewing directions, one or more of time comparing, structurally comparing and dynamically comparing the first projection image and the one or more projection images to determine an unobstructed viewing direction, where a second projection image corresponds with the one or more projection images at the unobstructed viewing direction, computing a third projection image from the second volumetric image measured at the second time using the unobstructed viewing direction, and displaying the second projection image and the third projection image.

A system for displaying unobstructed breast projection images comprising receiving a plurality of volumetric images of a breast, where a first volumetric image of the plurality of projection images is measured at a first time and a second volumetric image of the plurality of projection images is measured at a second time, where the first time differs from the second time by a time interval, computing a first projection image from the first volumetric image measured at the first time using a first viewing direction, computing one or more projection images from the first volumetric image measured at the first time using one or more viewing directions, one or more of time comparing, structurally comparing and dynamically comparing the first projection image and the one or more projection images to determine an unobstructed viewing direction, where a second projection image corresponds with the one or more projection images at the unobstructed viewing direction, computing a third projection image from the second volumetric image measured at the second time using the unobstructed viewing direction, and displaying the second projection image and the third projection image, further comprising computing a fourth projection image from the second volumetric image measured at the second time using the first viewing direction.

A method for identifying additional lesions in a tissue comprising the steps of computing a plurality of projection images of the tissue using a plurality of viewing directions, where a first projection image is computed using a first viewing direction and a second projection image is computed using a second viewing direction, displaying the first projection image and the second projection image, one or more of time comparing, structurally comparing and dynamically comparing the first projection image and the second projection image, visually identifying an intense spot that separates in the second projection image from the first projection image.

A system that displays a first projection image and a second projection image of a volumetric image comprising a processor responsive to a command to select a volumetric image one or more digital data processors capable of carrying out the steps including, computing a first projection image of the volumetric image using a first viewing direction, computing a second projection image of the volumetric image using a second viewing direction, and graphics resources for displaying the first projection image and the second projection image.

A system that compares a first projection image and a second projection image of a volumetric image comprising a processor responsive to a command to select a volumetric image, one or more digital data processors capable of carrying out the steps including computing a first projection image of the volumetric image using a first viewing direction, computing a second projection image of the volumetric image using a second viewing direction, and graphics resources for comparing the first projection image and the second projection image.

A method for displaying one or more unobstructed projection images comprising the steps of receiving a volumetric image, computing a plurality of projection images based on the volumetric image using a plurality of viewing directions, where at least a first projection image of the plurality of projection images is computed using a first viewing direction and at least a second projection image of the plurality of projection images is computed using a second viewing direction, where the first viewing direction is not equal to the second viewing direction, one or more of time comparing, structurally comparing and dynamically comparing the first projection image and the second projection image to determine if one or both of the first projection image and the second projection image are unobstructed, and displaying based on the comparison one or both the first projection image and the second projection image.

A method of visualizing a dynamic comparison of a volumetric image comprising the steps of receiving the volumetric image, computing a plurality of projection images of the volumetric image using a plurality of viewing directions between a smallest viewing direction and a largest viewing direction, and displaying a video showing the plurality of projection images, where the viewing direction changes with time.

Often, the traditional 'Hanging Protocol' is either not intuitive, cannot display the information in a manner in which it can be reviewed or is not the most efficient way to display images. Alternative ways of rendering the acquired images can be more efficient or more appropriate for displaying the information. Examples include Volume Rendering techniques or maximum intensity projections of stacks of cross-sectional images, rendering of oblique slices, rendering of thick slices or slabs, or rendering of fused images (e.g. in PET/CT). Specialized diagnostic workstations that are often specific to a clinical application area are used to provide appropriate rendering of the acquired images. As organizations and doctors require better and faster visualization methods that allow users to interact with the image data in real-time, the requirements and demands for displaying the data will increase.

Figure 11:
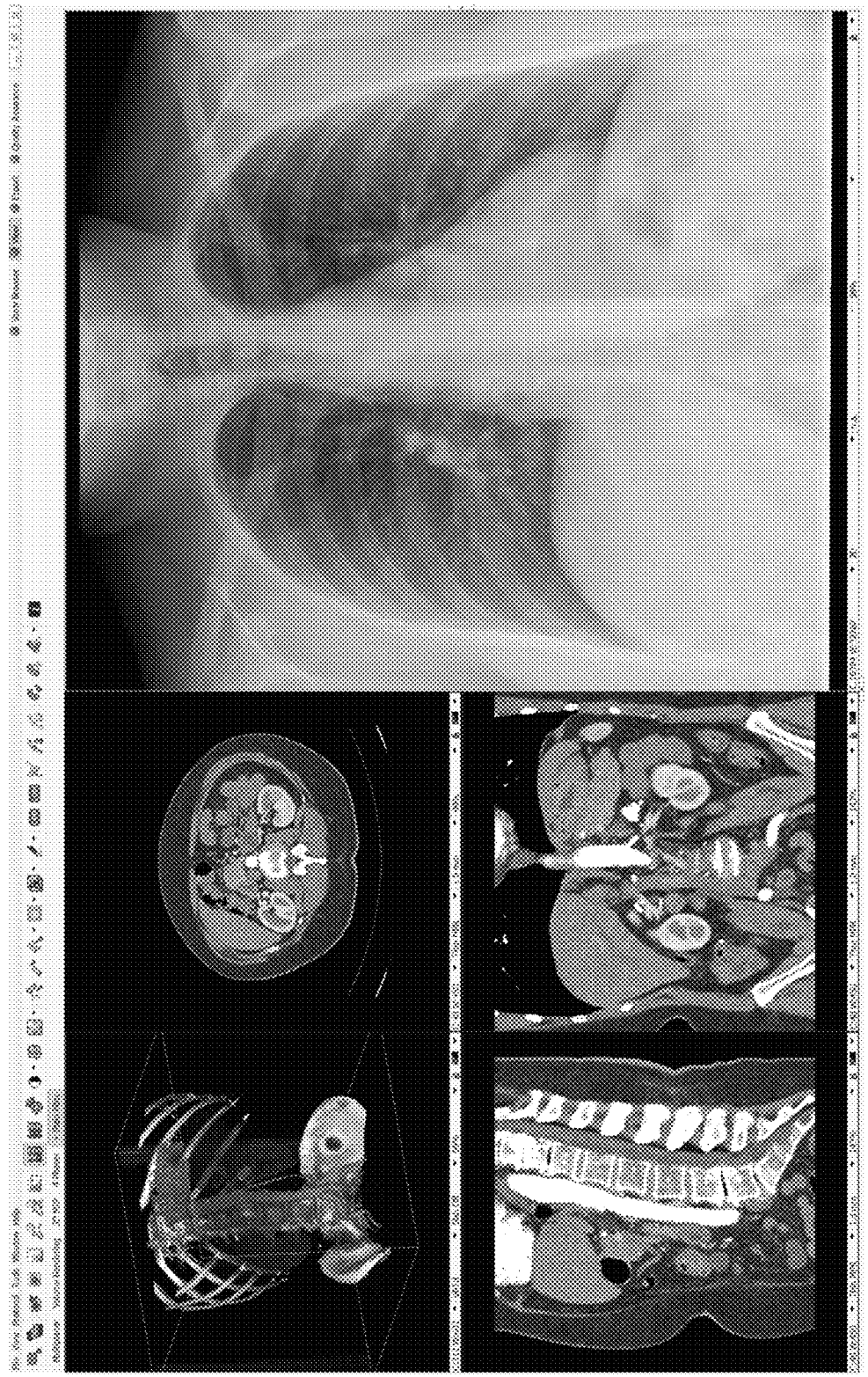
FIG. 11 depicts the resulting display for an example study, according to an embodiment of the invention.

FIG. 11 depicts an example study where the rules have created two Sets of Images. One Set of Images consists of a series of CT images forming a 3D volume, which is depicted in a volume rendered style in the Viewport 1160 in the upper left and in three orthogonal cross sections in the three other viewports in the left half of the screen. The second Set of Images consist of one chest X-Ray, assigned to a single Viewport 1160 covering the right half of the screen and rendering the X-Ray in 2D style. Appropriate data windows have been chosen by the rules to highlight the vasculature in the 3D rendering, as this is a study with contrast, as the rules can determine by the StudyDescription containing the word 'contrast'.

Figure 10:
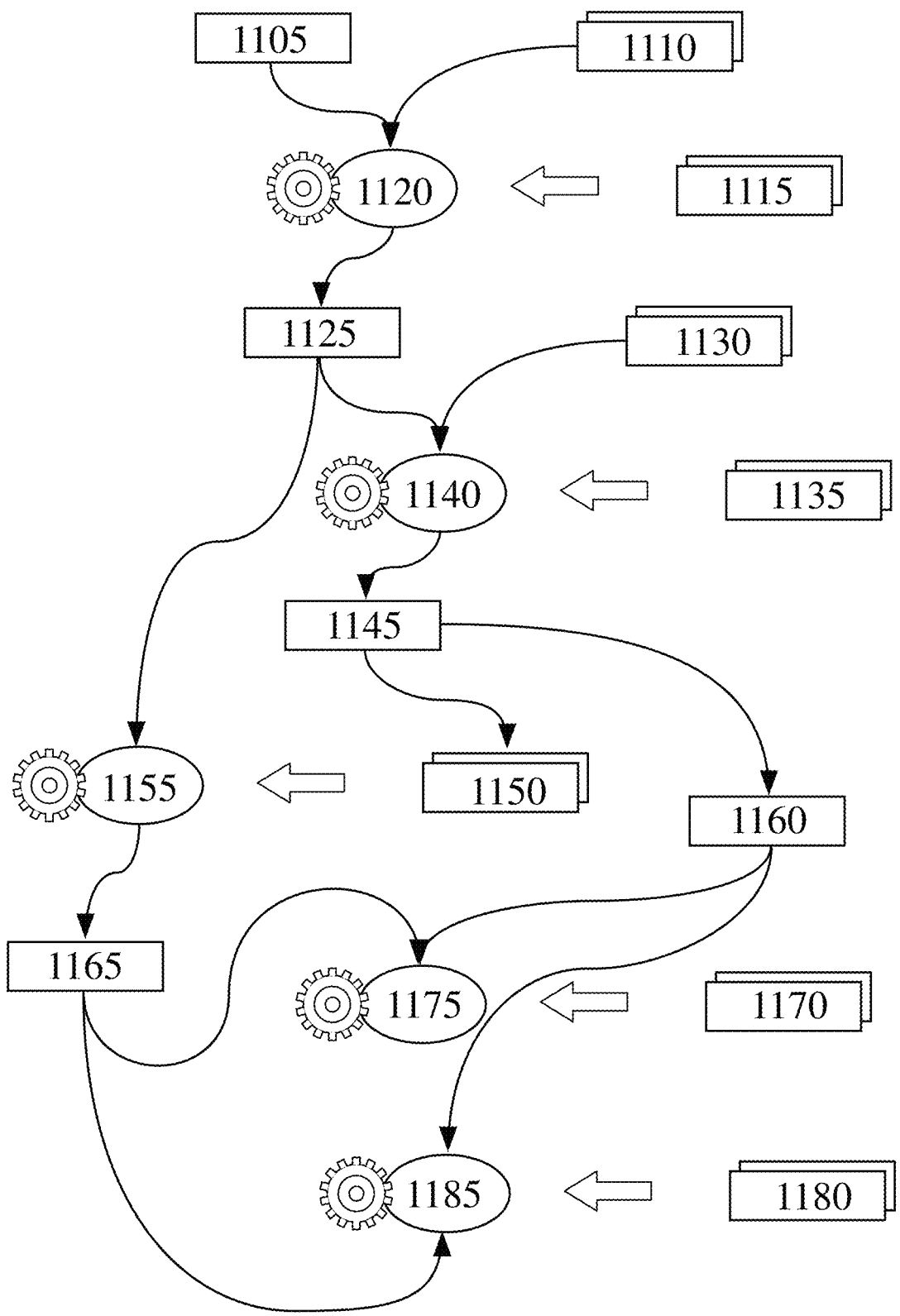
FIG. 10 depicts a flow chart showing the steps of applying various rules to the selected Study, according to an embodiment of the invention.
Figure 12A:
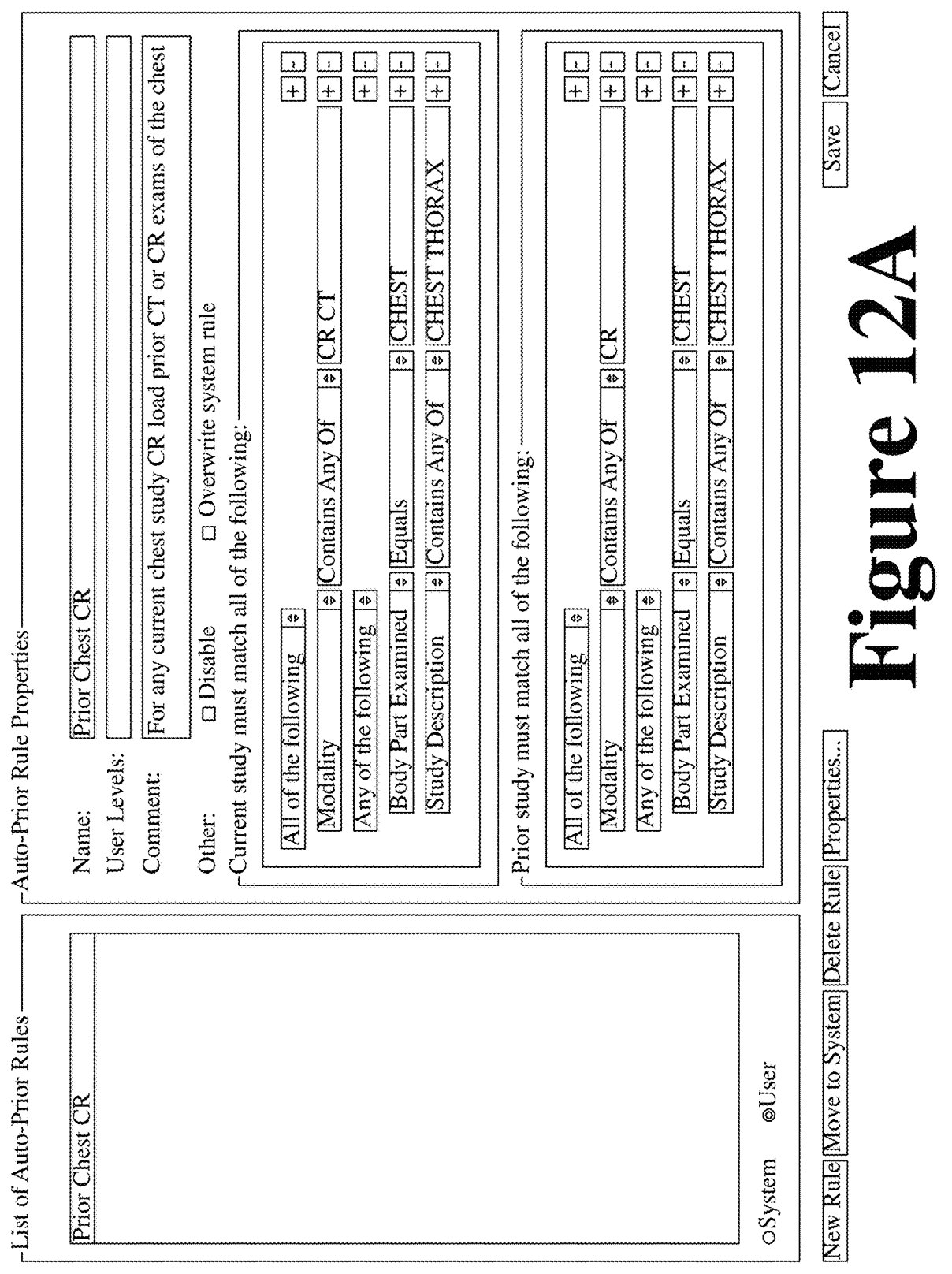
Figure 12B:
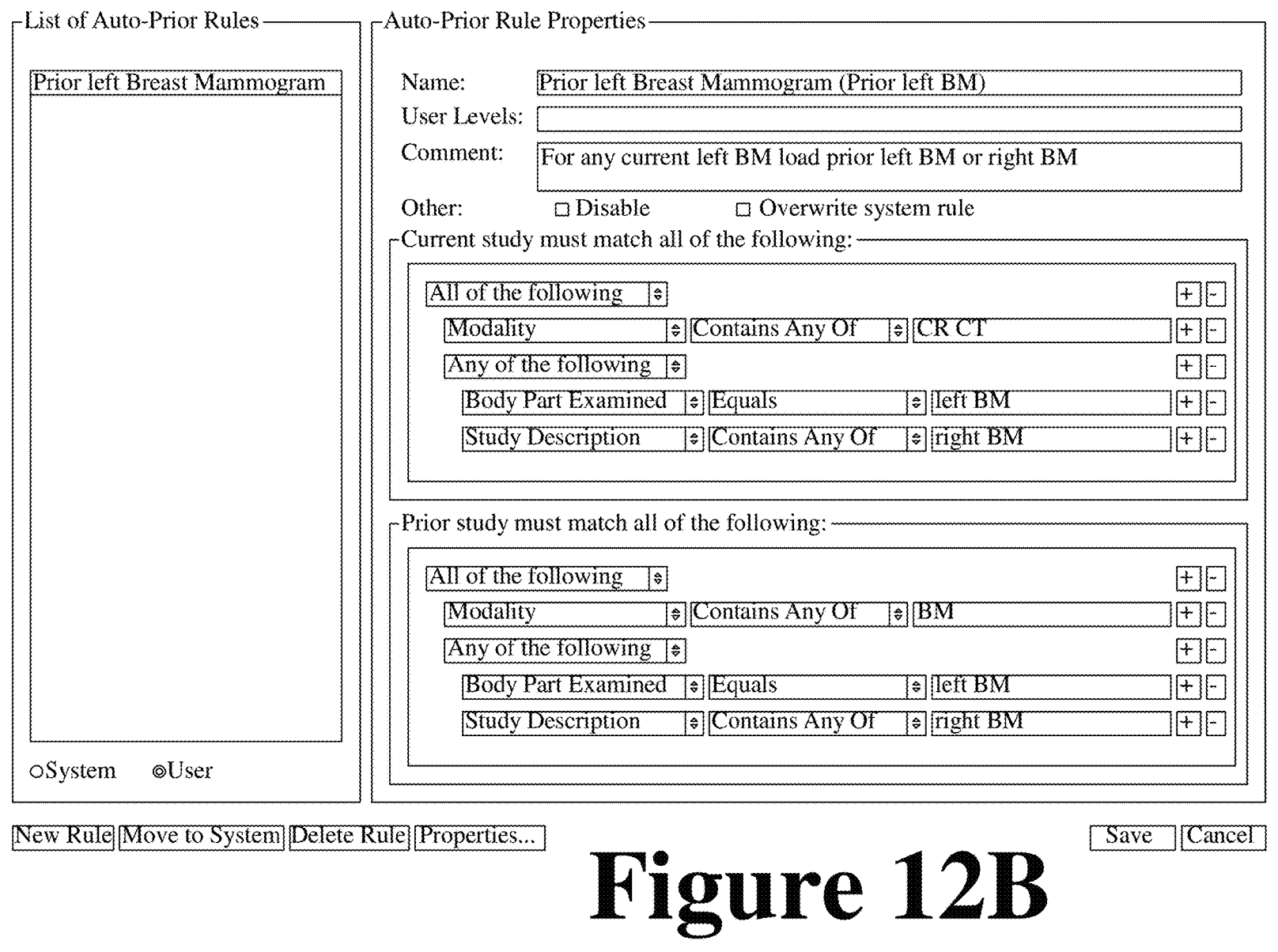

FIG. 10 is a flow chart showing how the rules are used to create the two Sets of Images shown in FIG. 11. As shown in FIG. 10, a primary Study 1105 which can be manually selected by a user. In step (i) 1120, based on Study Selection Rules 1115 which interrogate parameters in the primary Study 1105 such as DICOM Parameters and Abstract Tags of both the primary Study 1105 and the candidate studies 1110, the Study Selection Rules 1115 can identify additional candidate studies 1110. The second set of studies 1125 which includes the candidate studies 1110 and the primary Study 1105 are available to be loaded into Viewports 1160. In step (ii) 1140, the Protocol Selection Rules 1135 select a Display Protocol 1145 from the Available Display Protocols 1130 based on DICOM Parameters and Abstract Tags present in the second studies 1125. In step (iii) 1155, Image Set Rules 1150 are used to define a plurality of Image Sets 1165 from the second studies 1125. The one or more Viewports 1160 are defined in the Display Protocol 1145. In step (iv) 1175, Viewport Assignment Rules 1170 assign one or more Image Sets 1165 to one or more Viewports 1160. In step (v) 1185, Style Rules 1180 define a rendering style and rendering parameters. In an embodiment of the invention steps (i) through (v) are performed by a server processor running a render server program with an interface shown in FIG. 12A in which the rules (Study Selection Rules 1115, Protocol Selection Rules 1135, Image Set Rules 1150, Viewport Assignment Rules 1170, and the one or more Style Rules 1180) are used to automatically select and display the Image Sets 1165 in the Viewports 1160 for a prior chest CR analysis. In an embodiment of the invention steps (i) through (v) are performed by a server processor running a render server program with an interface shown in FIG. 12B in which the rules (Study Selection Rules 1115, Protocol Selection Rules 1135, Image Set Rules 1150, Viewport Assignment Rules 1170, and the one or more Style Rules 1180) are used to automatically select and display the Image Sets 1165 in the Viewports 1160 for a prior left breast mammogram analysis.

A render server program is described in U.S. application Ser. No. 13/831,967, entitled 'Multi-User Multi-GPU Render Server Apparatus and Methods', inventors M. Westerhoff et al., which was filed Mar. 15, 2013 is herein expressly incorporated by reference in its entirety. A rule based render server program is described in 'Method and System for Rule Based Display of Sets of Images', inventors M. Westerhoff et al., which issued as U.S. Pat. No. 8,976,190 on Mar. 10, 2015, and is herein incorporated by reference in its entirety. A program for improving data transfer is described in U.S. patent application Ser. No. 13/831,982 filed on Mar. 13, 2013, entitled 'Method and System for Transferring Data to Improve Responsiveness when Sending Large Data Sets', inventors D Stalling et al., which is herein incorporated by reference in its entirety.

Study Selection Rules 1115

In an embodiment of the present invention, based on the Study that the user selects for display (primary Study 1105), the system can first apply user defined rules to determine additional studies to be displayed together with the primary Study 1105. Such additional studies can be prior examinations that are relevant for the diagnosis of the current Study, or additional current studies. For example, a PET examination will often be looked at together with a CT examination acquired at the same time. The set of rules are constructed as follows:

Each rule consists of a matching criterion for the primary Study 1105 (primary condition), as well as matching criteria for additional studies (secondary condition). The matching criterion is an expression consisting of operators that allow evaluating the parameters of the Study and comparing them to defined values. The parameters of the Study are any parameters defined by the DICOM standard, such as Study Description, Study Date, Modality, Patient Age, as well as any other parameters that can be derived from the DICOM parameters or from the Study itself, such as number of images, or number of image series. The operators are numeric or string based operators, such as equals, greater than, less than, contains, etc. Expressions can be combined using Boolean operators such as AND, OR, NOT. Operators can also contain more complex expressions, including user defined functions defined in an appropriate programming language, such as JavaScript or VisualBasic.

Once a primary Study 1105 has been selected for display, the primary condition of each rule is evaluated. Those rules that match, i.e., evaluate to 'true' for the given primary Study 1105, will then be applied to all other studies that are available for the same patient. Those other studies for which the secondary condition matches will be added to the list of studies to be displayed.

The following rule illustrates the concept. This rule will automatically load prior Chest X-Rays or prior Chest CT if the primary Study 1105 is a Chest X-RAY.

Study Selection Rule 1:

IF (Primary.Dicom.BodyPartExamined='CHEST' and Primary.Dicom.Modality='CR') THEN SELECT other studies for loading WHERE (Other.Dicom.BodyPartExamined='CHEST' and (Other.Dicom.Modality='CR' or Other.Dicom.Modality='CT'))

The rule is expressed in pseudo-code with the primary condition specified in the IF-clause and the secondary condition expressed in the SELECT-clause.

Study Selection Rules: Normalization of DICOM Parameters

In an embodiment of the present invention, the rules can normalize DICOM parameters. As described above, a Study Selection Rule can contain arbitrary DICOM parameters. The DICOM standard specifies if a particular parameter is defined on a patient, Study, series, or image level. For example, a Study-level parameter should have the same value in all images of a Study, while a series-level parameter should have the same value in all images of a series. There are two problems related to assuming that this statement is always the case. Firstly, although a Study-level tag should have the same value for all images of a Study this is not always true. Secondly, some parameters are defined on a series- or image-level (e.g. modality is a series-level parameter) and therefore can be unavailable. In both cases it can be unclear what value is to be used when evaluating the rule. The invention described here provides different solutions to this problem.

In an embodiment of the present invention, a first approach is to choose a reference image and to read the value of a particular DICOM parameter from the reference image. The reference image can be: (i) the image that was inserted into the system first, (ii) the image with the oldest image content date, (iii) the image that was inserted into the system last, or (iv) the image with the earliest image content date. The choice of which image is to be chosen as the reference image can be configured for each parameter separately.

In an embodiment of the present invention, a second approach is to only allow original images to be chosen as the reference image. Non-viewable DICOM objects like structured reports, key objects, or presentation states are disregarded, as well as derived images such as secondary capture images or reformatted images.

In an embodiment of the present invention, a third approach is to provide a list of all distinct values that a particular DICOM parameter has in the images of a Study. In a Study Selection Rule one can then check if that list contains a particular value. The example above can then read as follows:

Study Selection Rule 2:

IF (Primary.Dicom.BodyPartExamined='CHEST' and Primary.DicomList.Modality contains 'CR') THEN SELECT other studies for loading WHERE (Other.Dicom.BodyPartExamined='CHEST' and (Other.DicomList.Modality contains 'CR' or Other.DicomList.Modality contains 'CT'))

Study Selection Rules: Abstract Tags

In an embodiment of the present invention, the Study Selection Rules 1115 contain other derived parameters such as Abstract Tags that characterize a Study in addition to or instead of DICOM parameters. Abstract tags that are useful within Study Selection Rules 1115 include the following:
(i) RelativeStudyAge indicates relative age of Study in days compared to primary Study 1105.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study.
(viii) HasThinSliceVolumes indicates whether the study has at least one set of images that form a true 3D volume, i.e. a sufficiently large number of equidistant slices (the exact number can be user configurable, e.g. 30 would be a common choice) and a sufficiently small spacing between two consecutive slices to guarantee an isotropic (or close to isotropic) (again, this parameter can be user defined, values between 1 mm and 3 mm are common thresholds for CT and MR examinations).

For example, a rule that applies to a Mammogram Study and that selects at maximum three prior Mammogram studies no older than five years can read as follows:
Study Selection Rule 3:
IF (Primary.Dicom.Modality='MG' THEN SELECT other studies for loading WHERE (Other.Dicom.Modality='MG' and Other.Abstract.Priorindex<=3 and Other.Abstract.RelativeStudyAge<5*365)
Protocol Selection Rules 1135

In an embodiment of the present invention, once the studies to be displayed are determined as described above, a suitable display protocol can be selected. This is done using matching rules. Each matching rule consists of conditions that are applied to the primary and other studies to be loaded. Like in Study Selection Rules 1115, protocol selection rules may contain DICOM parameters (either taken from a reference image or provided as a list of distinct values gathered from all images of a study), as well as abstract tags and user-defined functions. Each matching rule has a score and an associated display protocol.

In an embodiment of the present invention, all matching rules are evaluated and the display protocol of the matching rule that evaluates to true can be selected. If multiple matching rules evaluate to true, the one with the highest score can be selected.

The following example rule illustrates a matching rule that can apply for PET/CT studies of the abdomen to select a protocol named 'StandardPetCTProtocol1' with a score of 10.
Protocol Selection Rule 1:
IF (Primary.Dicom.BodyPartExamined='ABDOMEN' and Primary.Dicom.Modality='CT' and Exists(Other1) and Other1.Dicom.Modality='PET') THEN SELECT 'StandardPetCTProtocol1' with score=10

In an embodiment of the present invention, the rule is expressed in pseudo-code with the matching condition specified in the IF-clause and the chosen protocol specified by the SELECT.
Image Set Rules 1150

In an embodiment of the present invention, once a display protocol is selected, further rules defined within the protocol are evaluated. The next step comprises creation of so-called image sets. An image set consists of images that are logically grouped together. Usually, an image set is represented by a single preview icon in the application. It is an image set that is loaded into a viewer or tiled viewer. Note that DICOM series also represent a logical grouping of images. However, often DICOM series are not well suited for hanging of images and viewing. For example, in Mammography a single DICOM series may contain images of both left and right breast, in MRI it may contain both T1 and T2 images, or in CT it may contain both a localizer image (topogram) and a 3D image stack. In all these cases the DICOM series can be split into different logical image sets. On the other hand, multiple DICOM series may represent the phases of a single 4D cardiac data set. In this case all those series can be joined into a single logical image set.

Thus the creation of image sets based on rules is a key component of the rule-based display system, specifically for the more advanced rendering techniques. For example, the rules-based display system is used to create image sets that are very similar to the rules described above in Study Selection Rules 1115 and Protocol Selection Rules 1135 sections. A rule is a Boolean expression that can contain DICOM parameters, abstract tags, or used-defined functions that are based on the DICOM parameters, abstract tags, or used-defined functions. Image set rules however, are applied to all images of a study that was selected for loading (and not to the study itself). Image-level parameters thus represent no problem and do not need to be normalized or otherwise treated specially. All images that match an image-set rule are grouped into a respective image set.

In an embodiment of the present invention, the following rule (expressed in pseudo-code) collects all images of a current CT study:
Image Set Rule 1:
IF (Dicom.Modality='CT' and Abstract.Priorindex=0)
THEN CREATE image set with ID 1

In an embodiment of the present invention, the resulting image sets can be assigned IDs or names that allow for referencing the image sets later in layout and display set rules. In the above example an image set with ID 1 was defined. If no image matches an image set rule, no such corresponding image set will be created.
Image Set Rules: Sorting In an embodiment of the present invention, the order of images within an image set is an important aspect. It determines how images are shown when the user browses through the image set or how images are distributed into the tiles of a tiled viewer. In one embodiment of the present invention, in order to specify image sorting, the image set rules can contain an ordered list of sorting criteria. All images that are matched by a rule are sorted according to those criteria.

For example, the following rule collects all images of a current CT study and sorts them according to DICOM series number at first and DICOM instance/image number at second.
Image Set Rule 2:
IF (Dicom.Modality='CT' and Abstract.Priorindex=0)
THEN CREATE image set with ID 1
 SORTED BY Dicom.SeriesNumber ORDER:=ascending
 SORTED BY Dicom.InstanceNumber ORDER:=ascending
Image Set Rules: Splitting In an embodiment of the present invention, sorting criteria can be extended by a split flag. With the split flag it is possible to create multiple image sets from a single image set rule. When the value of a sorting criterion with split flag set to true changes, sub-sequent images are automatically inserted into a new image set. The resulting image sets are automatically enumerated by a sub-level ID.

For example, the following rule essentially creates image sets that correspond to DICOM series, because all images with different series number will be split into different sets:
Image Set Rule 3:
IF (Dicom.Modality='CT' and Abstract.Priorindex=0)
THEN CREATE image set with ID 1.x
    SORTED BY Dicom.SeriesNumber ORDER:=ascending SPLIT:=true
    SORTED BY Dicom.InstanceNumber ORDER:=ascending SPLIT:=false In applications where a CT has been measured, it can happen that a study contains both a soft-kernel series and a hard kernel series and both series have the same series number. In order to separate the images into different image sets the above rule can be extended by the following:
Image Set Rule 4:
IF (Dicom.Modality='CT' and Abstract.Priorindex=0)
THEN CREATE image set with ID 1.x
    SORTED BY Condition.CTSoftTisseKernel SPLIT:=true
    SORTED BY Dicom.SeriesNumber ORDER:=ascending SPLIT:=true
    SORTED BY Dicom.InstanceNumber ORDER:=ascending SPLIT:=false Here, Condition.CTSoftTissueKernel denotes a user-defined Boolean condition that tests whether an image has a CT soft-tissue kernel. The actual implementation of this condition can for example evaluate the manufacturer (which is encoded in a DICOM parameter). Depending on its value the rule can evaluate further parameters to find out if an image was reconstructed using a soft-tissue kernel or not. Since this Boolean condition was used as a sorting criterion with the split flag set to true, all non-soft-kernel images can be put into an image set with ID 1.1 and all soft-kernel images can be put into an image set with ID 1.2 (unless the image set is further split and IDs like 1.3 or 1.4 are created).

Image Set Rules: More Abstract Tags

In an embodiment of the present invention, additional abstract tags are used in image set rules. One example is a tag that identifies whether an image has already been put into an image set. In principle, a single image can be put into multiple image sets, but sometimes this should be avoided. This can be achieved by evaluating image set rules in a pre-defined order and introducing an abstract tag AlreadyReferenced.

For example, in CT study that has a localizer image and a 3D image stack both stored in one DICOM series, one may want to create an image set, one for the localizer and one for the 3D image stack. Accordingly, the image set rules are defined as follows:
Image Set Rule 5 (Localizer):
IF (Dicom.Modality='CT' and Condition.IsLocalizer=true)
THEN CREATE image set with ID 1
    SORTED BY Dicom.SeriesNumber ORDER:=ascending SPLIT:=true
    SORTED BY Dicom.InstanceNumber ORDER:=ascending SPLIT:=false
Image Set Rule 6 (Images):
IF (Dicom.Modality='CT' and Abstract.AlreadyReferenced=false)
THEN CREATE image set with ID 2
    SORTED BY Dicom.SeriesNumber ORDER:=ascending SPLIT:=true
    SORTED BY Dicom.InstanceNumber ORDER:=ascending SPLIT:=false Here Condition.IsLocalizer is a user-defined condition that returns true if an image is a localizer image, and false otherwise. In an embodiment of the present invention, Rule 1 is applied first. Therefore the localizer image is put into a separate image set with ID 1. Next rule 2 is applied. This rule can match for all CT images including the localizer image. However, because AlreadyReferenced=false is specified, the localizer image is skipped and not placed into image set 2.

In an embodiment of the present invention, the creation of the image sets based on rules is a key component of the efficient rules based display, specifically for the more advanced rendering techniques. For example rules can be used to identify sets of 2D images that together form a 3D volume.

Viewer Assignment Rules

In another embodiment of the present invention, a display protocol defines multiple viewers, each with one or more tiles, i.e., viewports. To each viewer one or more image sets can be assigned based on Viewer Assignment Rules that are similar to the protocol section rules described herein. Viewer Assignment Rules are defined in the display protocol. The rules determine which image set shall be initially shown in a viewer. In case multiple image sets are assigned to a viewer, the one with the highest score is chosen. Afterwards users may cycle quickly through the remaining image sets using dedicated tools (Previous/Next Image Set), or pick another image set from a special image set menu.

Like the other rule types Viewer Assignment Rules contain Boolean expressions of DICOM parameters, abstract tags, or user-defined conditions based on DICOM parameters, or abstract tags. In many cases it is sufficient to specify the image sets to be assigned to a viewer by their image set ID instead of evaluating the underlying DICOM parameters and abstract tags again. Therefore, the image set ID is simply set as a separate abstract tag. In the following example the two rules load image sets with the IDs 1 and 2 into a viewer, but assign ID 1 a higher score so that this image set is initially visible (provided such an image set exists):
Viewer Assignment Rule 1:
IF (EXISTS ImageSet[1])
THEN Viewport[0].AddImageSet(ID=1, score=10)
Viewer Assignment Rule 2:
IF (EXISTS ImageSet[2])
THEN
Viewport[0].AddImageSet(ID=2, score=5)

In an embodiment of the present invention, viewer assignment rules are applied to image sets. Thus there is a possible conflict regarding ambiguous image-level and series-level tags. This conflict is resolved in the same way as described herein in the Normalization of DICOM Parameters section. This means that values of DICOM parameters, but also abstract tags, are automatically taken from some reference image. Alternatively, for all DICOM parameters a list of distinct values occurring in all images of the image set can be used in an assignment rule.

Style Rules

In one embodiment of the present invention, there is a final set of rules that specify the rendering style and other rendering parameters to be used when showing a particular image set. For example, for a CT Angiogram study, often a volume rendering style display (VRT) is desired, whereas for a study looking for lung nodules a maximum intensity projection (MIP) of 20 mm slabs may be desired. Style rules, that can be user specific, allow driving that automatically. The rules can use the same parameters as discussed above, as well as the existence or absence of certain image sets.

In one embodiment of the present invention, the system uses a global, ordered list of style rules that is evaluated independently for each viewer and each image set loaded into a viewer. An abstract tag DisplaySetID is provided that allows formulating style rules for a specific viewer or group of viewers.

Parameters driven by Style Rules include the following:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

The following is an example of a style rule that activates inverse 3D MIP rendering in all viewers with a DisplaySetID between 101 and 104, provided a PET data set is loaded into those viewers (modality PT, i.e., positron emission tomography). Also, an automatic window/level setting is used that is computed from the histogram of the image set (the 2% lowest values are all mapped to white, and the 2% highest values are all mapped to black):

Style Rule 1:
IF (Abstract.DisplaySetID>100 and
   Abstract.DisplaySetID<105 and
   Dicom.Modality=TT')
THEN SET
   RenderingStyle:='3D MIP'
   Inverse:=true
   DataWindow:='2% 98%'

The following is another example of a different style rule that always causes the image set with image set ID 200 to be displayed in MPR mode using 20 mm thick slices, with a window/level as specified in the DICOM parameters, and with a zoom factor so that the whole viewer window is filled out. The rule is:

Style Rule 2:
IF (Abstract.ImageSetID=200)
THEN SET
   RenderingStyle:='MPR'
   SliceThickness:='20'
   DataWindow:='DICOM1'
   ZoomFactor:='FitToWindow'

Summary of Rule Types
Table I summarizes all types of rules that are applied in the rule-base display system:

TABLE I

| Rule Type | Applies to | Normalized Parameters | Defined where |
| --- | --- | --- | --- |
| Study Selection Rule | Studies | yes | globally |
| Protocol Selection Rule | Studies | yes | globally |
| Image Set Rule | Images | not required | protocol |
| Viewer Assignment Rule | Image Sets | yes | globally, protocol |
| Style Rule | Image Sets | yes | globally, protocol |

Example Shown in FIG. 11
An example of how these aspects can be combined is shown in FIG. 11. In the example the user has selected a CT examination of the abdomen. The following rules have been used to determine that a recent X-Ray of the chest is relevant and shall be displayed as well: IF (Primary.Dicom.BodyPartExamined='ABDOMEN' and Primary.Dicom.Modality='CT') THEN SELECT other studies for loading WHERE (Other.Dicom.BodyPartExamined='ABDOMEN' OR Other.Dicom.BodyPartExamined='CHEST') and (Other.Dicom.Modality='CR' or Other.Dicom.Modality='CT') AND Other.RelativeStudyAge<'90 days'

From this rule, a hanging protocol can be selected. In the example the protocol selection rules determine that the CT study is a thin slice CT study (i.e. that it has image series that form a 3D volume with sufficient resolution in all directions to display volume rendering or non-axial slices in a meaningful way). Furthermore the example rule determines that this is a study with enhanced vasculature, by looking for the key words 'contrast' or 'angio' in the study description. The display protocol selection rule that applies here and select the protocol CTThinSliceVesselWithPrior can read
IF (Primary.Dicom.BodyPartExamined='ABDOMEN' and Primary.Dicom.Modality='CT' and Primary.Abstract.HasThinSliceVolumes and (Primary.Dicom.StudyDescription containsAnyOf 'contrast, angio' and exists Other1 THEN SELECT 'CTThinSliceVesselWithPrior' with score=10

From this image sets are generated using Image Set Rules:
IF (Dicom.Modality='CT' and Abstract.Priorindex=0 and Condition.IsPartOfThinSliceVolume and Condition.CTSoftTisseKernel)
THEN CREATE image set with ID 1.x
   SORTED BY Abstract.NumberOfSlicesInVolume ORDER:=descending SPLIT:=true
   SORTED BY Dicom.SeriesNumber ORDER:=ascending SPLIT:=true
   SORTED BY Dicom.Abstract.VolumeIndex ORDER:=ascending SPLIT:=true
   SORTED BY Dicom.Abstract.SlicePosition ORDER:=ascending SPLIT:=false This rule will actually form sets from images that contain images that are part of a ThinSliceVolume and that have been reconstructed with a 'soft tissue' kernel. Given the protocol selection rule has specifically matched for just CT studies, the conditions Dicom.Modality='CT' and Abstract.Priorindex=0 are actually redundant, but could be useful if a different selection rule was used.

The images will first be sorted by the size of the volume of which they are part (Abstract.NumberOfSlicesInVolume), then by DICOM series. The split parameter in this case will ensure that an image set contains images from on series only. A DICOM series can sometimes contain multiple non-consecutive volumes. The abstract tag VolumeIndex will then indicate for each image, which of those volumes it is part of. If a series contains only one volume, then this will be '1' for all images in the series. The split=true in this part of the rule would result in a separate image set for each of those volumes. Finally, within each volume, the images are ordered by slice position, but not split. This way we end up with one image set for each soft kernel thin slice volume, the largest volume being the first image set (ID 1.1). This ID will be used further in subsequent rules.

The rule to form an image set from any CR prior study in this example is much simpler:
IF (Dicom.Modality='CR' and Abstract.Priorindex=1)
THEN CREATE image set with ID 10
   SORTED BY Dicom.SeriesNumber ORDER:=ascending SPLIT:=false
   SORTED BY Dicom.InstanceNumber ORDER:=ascending SPLIT:=false This creates one image set with ID=10 containing all images for the first prior study, if that is a CR.

In practice, additional rules, such as Image Set Rule 5 and 6 (see above) will be used to collect the remaining images of the primary Study 1105. The remaining images are not shown in the layout depicted in the example FIG. 11.

The Display Protocol 1145 contains multiple layouts. The one shown in FIG. 11 is defined as follows:

```
DEFINE Layout {
ID='Layout5';
NAME='+PlainFilm'
Viewports {
   { ID=50, Geometry='(0,0)-(0.25,0.5)'},
   { ID=51, Geometry='(0.25,0)-(0.5,0.5)'},
   { ID=52, Geometry='(0,0.5)-(0.25,1)'},
   { ID=53, Geometry='(0.25,0.5)-(0. 5,0.5)'},
   { ID=54, Geometry='(0.5,0)-(1,1)', Style='2D'}
   }
}
```

In this example the geometry is defined in a coordinate system having the origin in the upper left corner of the screen with the x axis pointing to the right and the y axis pointing down. Please note how parameters of the viewers can be set in the layout definition. Parameters can also be set or overridden in the assignment and style rules, as will be explained next.

In this example, viewer assignment and style rules are as follows:

```
IF ImageSetExists (1.1) and ImageSetExists(10) THEN
SHOW_LAYOUT Layout5 WITH
   Viewport[0].AddImageSet(1.1)
   Viewport [0].Style='VRT(diffuse)'
   Viewport [0].Colormap='CTAngioSoftTissue'
   Viewport [1,2,3].AddImageSet(1.1)
   Viewport [1,2,3].Style='MPR'
   Viewport [1,2,3].DataWindow='DICOM1'
   Viewport [1].orientation='axial'
   Viewport [2].orientation='sagittal'
   Viewport [3].orientation='coronal'
   Viewport [4].AddImageSet(10)
   IF (ImageSet[10].Dicom.Columns > 1024) THEN
   Viewport[4].Zoom='FitToWindow'
   ELSE
   Viewport[4].Zoom='1:1'
```

In this particular example, the rule to select the layout is rather simple: It is shown if the two image sets used exist. This is because the criteria to construct these images sets have been rather specific. As will be appreciated, the proposed system gives this type of flexibility.

ASPECTS OF THE INVENTION

Some aspects of this invention include methods of displaying one or more Sets of Images comprising the steps of: a. selecting a primary Study; b. selecting one or more Study Selection Parameters based on the primary Study; c. selecting one or more Study Selection Rules based on the one or more Study Selection Parameters; d. selecting one or more Sets of Images from a plurality of images based on the one or more Study Selection Rules; e. selecting one or more Display Protocol Selection Parameters based on the one or more Sets of Images selected; f. selecting one or more Display Protocol Selection Rules based on the one or more Display Protocol Selection Parameters; g. selecting one or more Display Parameters using the one or more Display Protocol Selection Rules; and h. displaying the one or more Sets of Images according to the Display Parameters.

Additional aspects include methods one or more Display Parameter are selected from the group consisting of Image Set Selection Parameters and View and Viewport Selection Parameters.

Further aspects include methods where the one or more Display Parameters are selected from the group consisting of Image Set Selection Rules, View and Viewport Selection Rules, and Display Protocol Selection Rules.

Yet further aspects include methods where the step of identifying one or more Image Set Selection Rules is based on the one or more Image Set Selection Parameters.

Still further aspects include methods where the step of selecting one or more Viewpoint Selection Rules is based on one or more View and Viewport Selection Parameters.

Other aspects include methods where the step of displaying the one or more Sets of Images is based on one or more Display Protocol Selection Rules, one or more Image Set Selection Rules, and one or more View and Viewport Selection Rules.

Still other aspects include methods where one or more of the Study Selection Parameters are selected from the group consisting of DICOM parameters and Abstract Tags.

Other aspects include methods where one or more of the Display Protocol Selection Parameters are selected from the group consisting of DICOM parameters and Abstract Tags.

Additional aspects include methods where one or more of the Image Set Selection Parameters are selected from the group consisting of DICOM parameters and Abstract Tags.

Further aspects include methods where one or more of the View and Viewport Selection Parameters are selected from the group consisting of DICOM parameters and Abstract Tags.

More aspects include methods where one or more Study Selection Parameters are derived from a single reference image.

Still more aspects include methods where one or more Study Selection Parameters are derived from a single reference image DICOM Parameters.

Yet other aspects include methods where one or more Display Protocol Selection Parameters are derived using a list of all values of a DICOM parameter occurring in any of the one or more Sets of Images.

Alternative aspects include methods where the one or more View and Viewport Selection Rules contain protocols for one or more Viewports displaying images as 2D.

Other alternative aspects include methods where the one or more View and Viewport Selection Rules contain protocols for one or more Viewports displaying images in a 3D rendering mode.

Further alternative aspects include methods where one or more Study Selection Parameters include one or more Abstract Tags selected from the group consisting of RelativeStudyAge, PriorIndex. NumImages, NumSeries, Num3DVolumes, Num4DSequences and HasReport.

In other aspects, this invention includes methods where one or more View and Viewport Selection Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In still other aspects, this invention comprises receiving one or more Sets of Images based on the Study Selection Rules, selecting one or more Image Set Selection Parameters, selecting one or more Image Set Selection Rules based on the one or more Image Set Selection Parameters and displaying the one or more Sets of Images based on the Display Protocol Selection Rules and the Image Set Selection Rules.

In another aspect, this invention comprises selecting one or more Study Selection Parameters, selecting or more Study Selection Rules based on the one or more Study Selection Parameters, receiving one or more Sets of Images based on the Study Selection Rules, selecting one or more Display Protocol Selection Parameters based on the one or more Sets of Images selected, selecting one or more Display Protocol Selection Rules based on the one or more Display Protocol Selection Parameters and displaying the one or more Sets of Images based on the Display Protocol Selection Rules.

Another aspect of this invention comprises selecting one or more Study Selection Parameters, selecting Study Selection Rules based on the one or more Study Selection Parameters, receiving one or more images based on the Study Selection Rules, selecting one or more Display Protocol Selection Parameters based on the one or more images selected, selecting Display Protocol Selection Rules based on the one or more Display Protocol Selection Parameters, selecting one or more Image Set Selection Parameters, selecting Image Set Selection Rules based on the one or more Image Set Selection Parameters, selecting one or more View and Viewport Selection Parameters, selecting View and Viewport Selection Rules based on the one or more View and Viewport Selection Parameters and displaying the one or more images based on the Display Protocol Selection Rules, the Image Set Selection Rules and the View and Viewport Selection Rules.

Other aspects of the invention include methods where the Study Selection Rule is: IF (Primary.Dicom.BodyPartExamined='CHEST' and Primary.Dicom.Modality='CR') THEN SELECT other studies for loading WHERE (Other.Dicom.BodyPartExamined='CHEST' and (Other.Dicom.Modality='CR' or Other.Dicom.Modality='CT')).

In another aspect, this invention includes methods where the Study Selection Rule is: IF (Primary.Dicom.BodyPartExamined='CHEST' and Primary.DicomList.Modality contains 'CR') THEN SELECT other studies for loading WHERE (Other.Dicom.BodyPartExamined='CHEST' and (Other.DicomList.Modality contains 'CR' or Other.DicomList.Modality contains 'CT')).

In other aspects, this invention includes methods where the Study Selection Rule is IF (Primary.Dicom.Modality='MG' THEN SELECT other studies for loading WHERE (Other.Dicom.Modality='MG' and Other.Abstract.Priorindex<=3 and Other.Abstract.RelativeStudyAge<5*365).

In yet another aspect, this invention includes methods where the Protocol Selection Rule is IF (Primary.Dicom.BodyPartExamined='ABDOMEN' and Primary.Dicom.Modality='CT' and Exists(Other1) and Other1.Dicom.Modality='PET') THEN SELECT 'StandardPetCTProtocol1' with score=10.

In aspects of the invention, methods include an Image Set Rule IF (Dicom.Modality='CT' and Abstract.Priorindex=0) THEN CREATE image set with ID 1.

Additionally, other aspects include methods where the Image Set Rule is: IF (Dicom.Modality='CT' and Abstract.Priorindex=0) THEN CREATE image set with ID 1, SORTED BY Dicom.SeriesNumber ORDER:=ascending, SORTED BY Dicom.InstanceNumber ORDER:=ascending.

Still other aspects include methods where the Image Set Rule is IF (Dicom.Modality='CT' and Abstract.Priorindex=0) THEN CREATE image set with ID 1.x, SORTED BY Dicom.SeriesNumber ORDER:=ascending SPLIT:=true, SORTED BY Dicom.InstanceNumber ORDER:=ascending SPLIT:=false.

Moreover, other aspects include methods where the Image Set Rule is IF (Dicom.Modality='CT' and Abstract.Priorindex=0) THEN CREATE image set with ID 1.x, SORTED BY Condition.CTSoftTisseKernel SPLIT:=true, SORTED BY Dicom.SeriesNumber ORDER:=ascending SPLIT:=true, SORTED BY Dicom.InstanceNumber ORDER:=ascending SPLIT:=false.

Yet other aspects include methods where the Image Set Rule (Localizer) is IF (Dicom.Modality='CT' and Condition.IsLocalizer=true) THEN CREATE image set with ID 1, SORTED BY Dicom.SeriesNumber ORDER:=ascending SPLIT:=true, SORTED BY Dicom.InstanceNumber ORDER:=ascending SPLIT:=false.

Other aspects of the methods of this invention include an Image Set Rule (Images) IF (Dicom.Modality='CT' and Abstract.AlreadyReferenced=false) THEN CREATE image set with ID 2, SORTED BY Dicom.SeriesNumber ORDER:=ascending SPLIT:=true, SORTED BY Dicom.InstanceNumber ORDER:=ascending SPLIT:=false.

Yet other aspects of the methods of this invention include using Image Set Rule (Images), IF (Dicom.Modality='CT' and Abstract.AlreadyReferenced=false) THEN CREATE image set with ID 2, SORTED BY Dicom.SeriesNumber ORDER:=ascending SPLIT:=true, SORTED BY Dicom.InstanceNumber ORDER:=ascending SPLIT:=false.

Additionally, other aspects include methods where the Display Parameters include Viewer Assignment Rule IF (Abstract.ImageSetID=1), THEN SELECT image set with score=10.

Yet further aspects include methods where the Display Parameters include a Viewer Assignment Rule IF (Abstract.ImageSetID=2) THEN SELECT image set with score=5.

Additional aspects include methods further comprising a Viewer Assignment Rule IF (Abstract.ImageSetID=2) THEN SELECT image set with score=5.

In other aspects of this invention, methods include one or more Study Selection Rules comprising one or more Abstract Tags selected from the group consisting of RelativeStudyAge indicates relative age of Study in days compared to primary Study 1105, PriorIndex indicates an index that enumerates all other studies from youngest to oldest, NumImages indicates number of images in Study, NumSeries indicated number of image series in Study, Num3DVolumes indicates number of 3D volumes in Study, Num4DSequences indicates number of 4D sequences in Study (e.g. Cardiac CT), and HasReport indicates a flag that indicates if a report is available for a Study, IsThinSliceVolume.

Aspects of methods also include a step of displaying including use of an Abstract Tag DisplaySetID.

Other aspects of methods include Abstract Tag DisplaySetID having a Style Rule selected from the group consisting of Rendering style (can be 2D, oblique, curved, MIP slab, 3D MIP, VRT, shaded VRT, etc.), Image alignment (left, right, top, bottom, centered), Inverse display (black on white versus white on black), Colormap or transfer function, Window/level (data window), Slice thickness, Zoom factor, Camera position and orientation; and Labels/OverlayDisplay of labels, annotations and other overlay elements.

Still other methods include steps where the Style Rule is IF (Abstract.DisplaySetID>100 and Abstract.DisplaySetID<105 and Dicom.Modality=TT') THEN SET RenderingStyle:='3D MIP', Inverse:=true, DataWindow:='2% 98%'.

Other aspects of methods include use of a Style Rule IF (Abstract.ImageSetID=200) THEN SET RenderingStyle:='MPR', SliceThickness:='20', DataWindow:='DICOM1', and ZoomFactor:='FitToWindow', Another aspect of the present invention is a method of displaying one or more Sets of Images comprises selecting one or more Study Selection Parameters, identifying one or more Study Selection Rules based on the one or more Study Selection Parameters, selecting one or more Sets of Images from a plurality of images based on the one or more Study Selection Rules, selecting one or more Display Protocol Selection Parameters based on the one or more Sets of Images selected, identifying one or more Display Protocol Selection Rules based on the one or more Display Protocol Selection Parameters, using the one or more Display Protocol Selection Rules to select one or more Display Parameters and displaying the one or more Sets of Images according to the Display Parameters.

Still other aspects of methods of displaying one or more Sets of Images comprising the steps of selecting one or more Study Selection Parameters, selecting Study Selection Rules based on the one or more Study Selection Parameters, selecting one or more Sets of Images based on the Study Selection Rules, selecting one or more Display Protocol Selection Parameters based on the one or more Sets of Images selected, selecting Display Protocol Selection Rules based on the one or more Display Protocol Selection Parameters, selecting one or more Image Set Selection Parameters, selecting Image Set Selection Rules based on the one or more Image Set Selection Parameters, selecting one or more View and Viewport Selection Parameters, selecting View and Viewport Selection Rules based on the one or more View and Viewport Selection Parameters and displaying the one or more Sets of Images based on the Display Protocol Selection Rules, the Image Set Selection Rules and the View and Viewport Selection Rules.

In systems of this invention, aspects include system for displaying one or more Sets of Images comprises selecting one or more Study Selection Parameters, selecting one or more Study Selection Rules based on the one or more Study Selection Parameters, receiving one or more Sets of Images based on the Study Selection Rules, selecting one or more Display Protocol Selection Parameters based on the one or more Sets of Images selected, selecting Display Protocol Selection Rules based on the one or more Display Protocol Selection Parameters, selecting one or more Image Set Selection Parameters, selecting one or more Image Set Selection Rules based on the one or more Image Set Selection Parameters, selecting one or more View and Viewport Selection Parameters, selecting View and Viewport Selection Rules based on the one or more View and Viewport Selection Parameters and graphics resources for displaying the one or more Sets of Images based on one or more of Display Protocol Selection Rules, Image Set Selection Rules, the View and Viewport Selection Rules, and Viewer Assignment Rules.

Additional system aspects include Sets of Images comprises one or more digital data processors for carrying out the steps according to any of the above described methods aspects and graphics resources for displaying the one or more Sets of Images.

In an embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In another embodiment of the invention, a method of displaying images comprises selecting one or more Study Selection Parameters, identifying a Study Selection Rule based on the one or more Study Selection Parameters, where the Study Selection Rule is: IF (Primary.Dicom.BodyPartExamined='CHEST' and Primary.Dicom.Modality='CR') THEN SELECT other studies for loading WHERE (Other.Dicom.BodyPartExamined='CHEST' and (Other.Dicom.Modality='CR' or Other.Dicom.Modality='CT')), receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters. selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In an alternative embodiment of the invention, a method of displaying images comprises selecting one or more Study Selection Parameters, identifying a Study Selection Rule based on the one or more Study Selection Parameters, where the Study Selection Rule is IF (Primary.Dicom.BodyPartExamined='CHEST' and Primary.DicomList.Modality contains 'CR') THEN SELECT other studies for loading WHERE (Other.Dicom.BodyPartExamined='CHEST' and (Other.DicomList.Modality contains 'CR' or Other.DicomList.Modality contains 'CT')), receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In another alternative embodiment of the invention, a method of displaying images comprises selecting one or more Study Selection Parameters, identifying a Study Selection Rule based on the one or more Study Selection Parameters, where the Study Selection Rule is IF (Primary.Dicom.Modality='MG' THEN SELECT other studies for loading WHERE (Other.Dicom.Modality='MG' and Other.Abstract.Priorindex<=3 and Other.Abstract.RelativeStudyAge<5*365), receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters; selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In an embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying a Display Protocol Selection Rule based on the one or more Display Protocol Selection Parameters, where the Display Protocol Selection Rule is IF (Primary.Dicom.BodyPartExamined='ABDOMEN' and Primary.Dicom.Modality='CT' and Exists(Other1) and Other1.Dicom.Modality='PET') THEN SELECT 'StandardPetCTProtocol1' with score=10, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In a further embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying an Image Set Selection Rule based on the one or more Image Set Selection Parameters, where the Image Set Selection Rule (Localizer) is IF (Dicom.Modality='CT' and Abstract.AlreadyReferenced=false) THEN CREATE image set with ID 2, SORTED BY Dicom.SeriesNumber ORDER:=ascending SPLIT:=true, SORTED BY Dicom.InstanceNumber ORDER:=ascending SPLIT:=false; selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In another embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, where the one or more Display Protocol Selection Parameters include Viewer Assignment Rule IF (Abstract.ImageSetID=1) THEN SELECT image set with score=10; identifying Display Protocol Selection Rules based on the one or more Display Protocol Selection Parameters, selecting one or more Image Set Selection Parameters;
identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In an additional embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, where the one or more Display Protocol Selection Parameters include Viewer Assignment Rule IF (Abstract.ImageSetID=1) THEN SELECT image set with score=10, identifying Display Protocol Selection Rules based on the one or more Display Protocol Selection Parameters, selecting one or more Image Set Selection Parameters; identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In a further embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, where the one or more Display Protocol Selection Parameters include Viewer Assignment Rule IF (Abstract.ImageSetID=2) THEN SELECT image set with score=5, identifying Display Protocol Selection Rules based on the one or more Display Protocol Selection Parameters, selecting one or more Image Set Selection Parameters, identifying Image Set Selection Rules based on the one or more Image Set Selection Parameters; selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In a still further embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters, displaying the one or more images based on the Display Protocol Selection Rules, the Image Set Selection Rules and the View and Viewport Selection Rules; and selecting Viewer Assignment Rule IF (Abstract.ImageSetID=2) THEN SELECT image set with score=5.

In an embodiment of the invention, a method of displaying images comprises selecting one or more Study Selection Parameters, identifying Study Selection Rules based on the one or more Study Selection Parameters, where the one or more Study Selection Rules comprise one or more Abstract Tags selected from the group consisting of RelativeStudy-Age indicates relative age of Study in days compared to primary Study, PriorIndex indicates an index that enumerates all other studies from youngest to oldest, NumImages indicates number of images in Study, NumSeries indicated number of image series in Study, Num3DVolumes indicates number of 3D volumes in Study, Num4DSequences indicates number of 4D sequences in Study (e.g. Cardiac CT) and HasReport indicates a flag that indicates if a report is available for a Study; receiving one or more images based on the Study Selection Rules, selecting one or more Display Protocol Selection Parameters based on the one or more images selected, identifying Display Protocol Selection Rules based on the one or more Display Protocol Selection Parameters selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules.

In another embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules, where the step of displaying includes an Abstract Tag DisplaySetID.

In another embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of Rendering style (can be 2D, oblique, curved, MIP slab, 3D MIP, VRT, shaded VRT, etc.), Image alignment (left, right, top, bottom, centered), Inverse display (black on white versus white on black), Colormap or transfer function, Window/level (data window), Slice thickness, Zoom factor, Camera position and orientation and Labels/OverlayDisplay of labels, annotations and other overlay elements.

In a further embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters an displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of Rendering style (can be 2D, oblique, curved, MIP slab, 3D MIP, VRT, shaded VRT, etc.), Image alignment (left, right, top, bottom, centered), Inverse display (black on white versus white on black), Colormap or transfer function, Window/level (data window), Slice thickness, Zoom factor, Camera position and orientation and Labels/OverlayDisplay of labels, annotations and other overlay elements; where the Style Rule is IF (Abstract.DisplaySetID>100 and Abstract.DisplaySetID<105 and Dicom.Modality='TT') THEN SET RenderingStyle:='3D MIP', Inverse:=true and DataWindow:='2% 98%'.

In a still further embodiment of the invention, a method of displaying images comprises selecting one or more Study Selection Parameters, identifying Study Selection Rules based on the one or more Study Selection Parameters, receiving one or more images based on the Study Selection Rules, selecting one or more Display Protocol Selection Parameters based on the one or more images selected, identifying Display Protocol Selection Rules based on the one or more Display Protocol Selection Parameters, selecting one or more Image Set Selection Parameters, identifying Image Set Selection Rules based on the one or more Image Set Selection Parameters, selecting one or more View and Viewport Selection Parameters, identifying View and Viewport Selection Rules based on the one or more View and Viewport Selection Parameters and displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of Rendering style (can be 2D, oblique, curved, MIP slab, 3D MIP, VRT, shaded VRT, etc.), Image alignment (left, right, top, bottom, centered), Inverse display (black on white versus white on black), Colormap or transfer function, Window/level (data window), Slice thickness, Zoom factor, Camera position and orientation and Labels/OverlayDisplay of labels, annotations and other overlay elements; where the Style Rule is IF (Abstract.ImageSetID=200) THEN SET RenderingStyle:='MPR', SliceThickness:='20', DataWindow:='DICOM1' and ZoomFactor:='FitToWindow'.

In an embodiment of the invention, a method of displaying one or more Sets of Images comprises selecting one or more Study Selection Parameters, selecting or more Study Selection Rules based on the one or more Study Selection Parameters, receiving one or more Sets of Images based on the Study Selection Rules, selecting one or more Display Protocol Selection Parameters based on the one or more Sets of Images selected, selecting one or more Display Protocol Selection Rules based on the one or more Display Protocol Selection Parameters and displaying the one or more Sets of Images based on the Display Protocol Selection Rules.

In a further embodiment of the invention, a method of displaying one or more Sets of Images comprises selecting a primary Study, selecting one or more Study Selection Parameters based on the primary Study, selecting one or more Study Selection Rules based on the one or more Study Selection Parameters, selecting one or more Sets of Images from a plurality of images based on the one or more Study Selection Rules, selecting one or more Display Protocol Selection Parameters based on the one or more Sets of Images selected, selecting one or more Display Protocol Selection Rules based on the one or more Display Protocol Selection Parameters, selecting one or more Display Parameters using the one or more Display Protocol Selection Rules, where the one or more Display Parameter are selected from the group consisting of Image Set Selection Parameters and View and Viewport Selection Parameters and displaying the one or more Sets of Images according to the Display Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a two dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a three dimensional (3D) image displayed with a 3D rendering style.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays an oblique cross section through a volumetric image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a maximum intensity projection of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a post processed rendering of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a thick slab image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a volume rendered image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a three dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where one or more Study Selection Rules used DICOM parameters and Abstract Tags derived from a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image, where one or more Study Selection Rules are derived from the single reference image DICOM Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules contain protocols for displaying two dimensional images in the one or more Viewports.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Abstract Tags are selected from the group consisting of RelativeStudyAge, PriorIndex. NumImages, NumSeries, Num3DVolumes, Num4DSequences and Has-Report.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Image Set Rules are selected from selection, sorting, and breaking rules, where the one or more Image Set Rules are Boolean expressions that contain parameters selected from the group consisting of DICOM parameters, abstract tags, and used-defined functions.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria, where a split flag is used in order to specify image splitting.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules, where an Abstract Tag identifies whether an image has already been placed into an Image Set.

In an alternative embodiment of the invention, a system of displaying one or more Sets of Images from a plurality of images comprises selecting one or more studies from a plurality of studies, one or more digital data processors for carrying out the steps including applying one or more Protocol Selection Rules to select a Display Protocol, where the one or more Protocol Selection Rules are based on one or more DICOM parameters and Abstract Tags from the plurality of studies, applying one or more Image Set Rules to define a plurality of Image Sets from the plurality of studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the one or more Image Sets based on one or more of the Protocol Selection Rules, the one or more Image Set Rules, the one or more Viewport Assignment Rules, and the one or more Style Rules, where at least one of the one or more Viewports displays a three dimensional image.

In another alternative embodiment of the invention, a method of displaying one or more Sets of Images from a plurality of images comprises selecting a primary Study from a plurality of studies, executing on a server digital data processor a render server program which applies one or more of one or more Study Selection Rules, one or more Protocol Selection Rule, one or more Image Set Rules, one or more Viewport Assignment Rules, and one or more Style Rules to display the one or more Sets of Images including the steps of applying the one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying the one or more Protocol Selection Rules to select a Display Protocol, where the one or more Protocol Selection Rules are based on one or more DICOM parameters and one or more Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the Protocol Selection Rule, the Image Set Rule, the one or more Viewport Assignment Rules, and the one or more Style Rules, where at least one of the one or more Viewports displays a volume rendered image.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set, where the step of displaying is carried out on a client display device.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports from the plurality of medical diagnostic reports, the server receiving a patient ID from a remote computer from the one or more remote computers, the server executing a render server program which applies one or more of one or more Study Selection Rules based on the patient ID to select a Study from the plurality of medical diagnostic reports, the render server program applying one or more Protocol Selection Rules and one or more Image Set Rules to generate a volumetric image reconstructed from the Study, the render server defining at least three viewing directions for the Study based on the one or more Protocol Selection Rules and the one or more Display Protocols, the render server generating at least three projection images from the volumetric image at the at least three viewing directions based on the one or more Protocol Selection Rules and the one or more Display Protocols, the server selecting three or more images of the Study from the at least three projection images and the server sending the three or more images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports from the plurality of medical diagnostic reports, the server receiving a patient ID from a remote computer from the one or more remote computers, the server executing a render server program which applies one or more of one or more Study Selection Rules based on the patient ID to select a Study from the plurality of medical diagnostic reports, the render server program applying one or more Protocol Selection Rules and one or more Image Set Rules to generate a volumetric image reconstructed from the Study, the render server defining at least three viewing directions for the Study based on the one or more Protocol Selection Rules and the one or more Display Protocols, the render server generating at least three projection images from the volumetric image at the at least three viewing directions based on the one or more Protocol Selection Rules and the one or more Display Protocols, the server selecting three or more images of the Study from the at least three projection images and the server sending the three or more images to the remote computer, further comprising displaying a video comprising the three or more images.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images where one or more Protocol Selection Rules are used to select a viewing direction that improves identification of a first projection image, identification of a microcalcification, identification of an obstruction, resolution of two microcalcifications, resolution of a microcalcification and an obstruction, resolution of two obstructions, direct comparison of a microcalcification and direct comparison of an obstruction, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports, where the first Study is a Digital Breast Tomosynthesis scan and one or more of one or more Study Selection Rules based on the first Study to select a second Study of the plurality of medical diagnostic reports, where the second Study is a Digital Breast Tomosynthesis scan corresponding to the first Study, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports, where the first Study is a first volumetric image reconstructed from a Digital Breast Tomosynthesis scan and one or more of one or more Study Selection Rules based on the first Study to one or both select and generate a second Study of the plurality of medical diagnostic reports, where the second Study is a second volumetric image reconstructed Digital Breast Tomosynthesis scan, where the second Study is a corresponding tissue to the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer, where the first Set of Images are displayed as a video.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer, where the first Set of Images are displayed as a video, where the video displays a dynamic comparison.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, where the viewing directions are selected according to a periodic continuous mathematical function, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, where the viewing directions are selected according to a periodic continuous mathematical function, where the at least three projection images are generated from viewing directions spanning one period of the periodic continuous mathematical function, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images to the remote computer, where the remote computer stores the first Set of Images.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, and one or both the render and the render program sending the first Set of Images and instructions to display the first Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where one or more Protocol Selection Rules are used to select a viewing direction that identifies a microcalcification, an obstruction, that a microcalcification includes two or more microcalcifications, that an obstruction includes a microcalcification and an obstruction, that an obstruction includes two or more obstructions, a microcalcification using direct comparison and an obstruction using direct comparison, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where one or more Protocol Selection Rules are used to select a viewing direction selected from the first Set of Images that improves identification of an initial projection image, a viewing direction selected from the first Set of Images that improves comparison of an initial projection image and a subsequent projection image, a viewing direction selected from the first Set of Images that improves identification of a microcalcification, a viewing direction selected from the first Set of Images that improves identification of an obstruction, a viewing direction selected from the first Set of Images that improves resolution of two microcalcifications, a viewing direction selected from the first Set of Images that improves resolution of a microcalcification and an obstruction, a viewing direction selected from the first Set of Images that improves resolution of two obstructions, a viewing direction selected from the first Set of Images that improves direct comparison with an initial projection image and a subsequent projection image, a viewing direction selected from the first Set of Images that improves direct comparison of a microcalcification and a viewing direction selected from the first Set of Images that improves direct comparison of an obstruction, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports, where the first Study Study is a Digital Breast Tomosynthesis scan and one or more of one or more Study Selection Rules based on the first Study to select a second Study of the plurality of medical diagnostic reports, where the second Study Study is a complementary Digital Breast Tomosynthesis scan of the first Study, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where one or both the first Set of Images and the second Set of Images are displayed as a video.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where one or both the first Set of Images and the second Set of Images are displayed as a video, where the video displays a dynamic comparison.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, where the at least three viewing directions are selected according to a periodic continuous mathematical function, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, where the at least three viewing directions are selected according to a periodic continuous mathematical function, where the at least three viewing directions span one period of the periodic continuous mathematical function, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where the remote computer stores one or both the first Set of Images and the second Set of Images.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images and instructions to one or both display the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, where the first Study is a first reconstructed volumetric image, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to one or both select and generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where the first Set of Images is displayed as a first video and the second Set of Images is displayed as a second video.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where the first Set of Images is displayed as a first video and the second Set of Images is displayed as a second video, where the first video and the second video display a time comparison.

In an embodiment of the invention, a method comprises providing a server computer in communication with one or more remote computers, where the server computer includes one or more processors and an associated memory, where a plurality of medical diagnostic reports are stored on the memory, where the plurality of medical diagnostic reports can be accessed by the one or more processors based on a plurality of patient IDs, where a patient ID corresponds with one or more medical diagnostic reports selected from the plurality of medical diagnostic reports, the server receiving a patient ID from a remote computer from the one or more remote computers, the server executing a render server program which applies one or more of one or more Study Selection Rules based on the patient ID to select a first Study of the plurality of medical diagnostic reports and one or more of one or more Study Selection Rules based on the first Study to select a second Study of the plurality of medical diagnostic reports, the render server program applying one or more Protocol Selection Rules and one or more Image Set Rules to generate a first volumetric image reconstructed from the first Study, the render server program defining at least three viewing directions for the first Study based on the one or more Protocol Selection Rules and the one or more Display Protocols, the render server program generating at least three first projection images from the first volumetric image at the at least three viewing directions based on the one or more Protocol Selection Rules and the one or more Display Protocols, the render server program selecting three or more images from the at least three first projection images which correspond with three or more viewing directions to form a first Set of Images, the render server program applying one or more Protocol Selection Rules and one or more Image Set Rules to generate a second volumetric image reconstructed from the second Study, the render server program using the three or more viewing directions to generate three or more second projection images from the second volumetric image, where the three or more second projection images form a second Set of Images and the render program sending the first Set of Images and the second Set of Images to the remote computer, where the first Set of Images is displayed as a first video and the second Set of Images is displayed as a second video, where the first video and the second video display a structural comparison.

In an embodiment of the invention, a method comprises providing a remote computer, the remote computer selecting a Study including a plurality of measured projection images, sending instructions to a host computer based on one or more Protocol Selection Rules and one or more Image Set Rules to generate a volumetric image reconstructed from the plurality of measured projection images, instructing the host computer to compute three or more projection images of the volumetric image using three or more viewing directions defined based on the one or more Protocol Selection Rules and the one or more Display Protocols, where the three or more viewing directions change with time, instructing the host computer to send the three or more projection images to the remote computer, applying one or more Protocol Selection Rules with the Set of Images to generate a Set of Images and displaying on the remote display the Set of Images.

In an embodiment of the invention, a method comprises for a first tissue, selecting a first Study including a plurality of measured projection images, generating a primary volumetric image reconstructed from the first Study based on one or more Protocol Selection Rules and one or more Image Set Rules, defining three or more viewing directions for the first Study based on one or more Protocol Selection Rules and one or more Display Protocols, generating three or more primary projection images from a volumetric image based on the three or more viewing directions, where the three or more primary projection images form a first Set of Images, applying the one or more Protocol Selection Rules with the first Set of Images to generate a first video of the first Study, for a second tissue, applying one or more Study Selection Rules to generate a second Study based on one or more DICOM parameters and one or more Abstract Tags of the first Study and one or more DICOM parameters and one or more Abstract Tags of the second Study, generating a volumetric image reconstructed from the second Study based on the one or more Protocol Selection Rules and one or more Image Set Rules, defining three or more equivalent viewing directions for the second Study based on one or more of the three or more viewing directions, the one or more Protocol Selection Rules and the one or more Display Protocols, generating three or more second projection images from the second volumetric image based on the three or more equivalent viewing directions, where the three or more second projection images form a second Set of Images, applying the one or more Protocol Selection Rules with the second Set of Images to generate a second video of the second Study and displaying the first video and the second video.

Described above are methods and systems for implementing a rule derived basis to display three or more 2-D projections of volumetric image sets including DBT volume sets. The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A method to display a video comprising:
providing a server computer in communication with a remote computer, where the server computer:
a) receives a patient ID from the remote computer, where the patient ID corresponds with one or more medical diagnostic reports of a patient selected from a plurality of medical diagnostic reports;
b) executes a render server program comprising:
i) a step for applying one or more Study Selection Rules based on the patient ID to select a Study from the plurality of medical diagnostic reports;
ii) a step for constructing from the Study a volumetric image of an anatomical region of the patient;
iii) a step for defining at least three viewing directions; and
iv) a step for generating at least three projection images at the at least three viewing directions from the volumetric image; and
c) sends a video comprising the at least three projection images to the remote computer.

2. The method of claim 1, where the Study is a Digital Breast Tomosynthesis scan.

3. The method of claim 1, where one or more Protocol Selection Rules are used to select a viewing direction that identifies one or both a microcalcification and an obstruction.

4. The method of claim 1, where one or more Protocol Selection Rules are used to select a viewing direction that improves: identification of a projection image; comparison of a projection image; identification of a microcalcification; identification of an obstruction;
resolution of two microcalcifications; resolution of a microcalcification and an obstruction; resolution of two obstructions; direct comparison with a first projection image and a second projection image; direct comparison of a microcalcification; and direct comparison of an obstruction.

5. The method of claim 1, where the video displays a dynamic comparison.

6. The method of claim 1, where the video displays a direct comparison.

7. The method of claim 1, where the at least three viewing directions are selected according to a periodic continuous mathematical function.

8. The method of claim 7, where the three or more images are generated from viewing directions spanning one period of the periodic continuous mathematical function.

9. The method of claim 1, further comprising storing the video in a cache.

10. A method comprising:
(A) receiving at a server from a client computer a primary study of a patient;
(B) executing on the server a server program, where the server program carries out:
(i) a step for constructing a volumetric image of an anatomical region of the patient from the primary study;
(ii) a step for defining at least three viewing directions;
(iii) a step for generating at least three projection images using the at least three viewing directions; and
(iv) a step for generating a video comprising the at least three projection images; and (C) sending the video from the server to the client computer.

11. The method of claim 10, where the primary study is a Digital Breast Tomosynthesis scan.

12. The method of claim 10, where one or more Protocol Selection Rules are used to select a viewing direction that identifies: a microcalcification; an obstruction; a microcalcification that includes two or more microcalcifications; an obstruction that includes a microcalcification and an obstruction; an obstruction that includes two or more obstructions; a microcalcification using direct comparison; and an obstruction using direct comparison.

13. The method of claim 10, where one or more Protocol Selection Rules are used to select a viewing direction that improves: identification of a projection image; comparison of a projection image; identification of a microcalcification; identification of an obstruction; resolution of two microcalcifications; resolution of a microcalcification and an obstruction; resolution of two obstructions; direct comparison with a first projection image and a second projection image; direct comparison of a microcalcification; and direct comparison of an obstruction.

14. The method of claim 10, where the video displays a dynamic comparison.

15. The method of claim 10, where the video displays a direct comparison.

16. The method of claim 10, where the at least three viewing directions are selected according to a periodic continuous mathematical function.

17. The method of claim 16, where the three or more images are generated from viewing directions spanning one period of the periodic continuous mathematical function.

18. The method of claim 16, further comprising storing the video.

19. A method comprising:
(A) receiving at a server from a client computer a patient ID corresponding to a patient, the server comprising a server digital data processor, and the client computer comprising a client digital data processor;
(B) executing on the server a render server program comprising:
  (i) a step for applying one or more Study Selection Rules based on the patient ID to select a Study of the patient;
  (ii) a step for constructing a volumetric image of an anatomical region of the Study;
  (iii) a step for defining at least three viewing directions;
  (iv) a step for generating at least three projection images at the at least three viewing directions from the volumetric image;
  (v) a step for constructing a video comprising the at least three projection images; and
(C) sending the video from the server to the client computer.

20. The method of claim 19, where one or more Protocol Selection Rules are used to select a viewing direction that identifies: a microcalcification; an obstruction; a microcalcification that includes two or more microcalcifications; an obstruction that includes a microcalcification and an obstruction; an obstruction that includes two or more obstructions; a microcalcification using direct comparison; and an obstruction using direct comparison.

* * * * *